US012564440B2

(12) United States Patent
Turovskiy et al.

(10) Patent No.: US 12,564,440 B2
(45) Date of Patent: *Mar. 3, 2026

(54) MULTI-STRUT ABLATION AND SENSING CATHETER DEVICES AND METHODS

(71) Applicant: Pulse Biosciences, Inc., Hayward, CA (US)

(72) Inventors: Roman Turovskiy, San Francisco, CA (US); David R. Kirkland, Hayward, CA (US); David J. Danitz, San Jose, CA (US); David Moosavi, Hayward, CA (US); Rodel Quintos, Cupertino, CA (US); Ryan C. Bradway, Murrieta, CA (US); Andy E. Denison, Temecula, CA (US); Dylan R. Montgomery, Murrieta, CA (US); Peter J. D'Aquanni, Murrieta, CA (US)

(73) Assignee: Pulse Biosciences, Inc., Hayward, CA (US)

( * ) Notice: Subject to any disclaimer, the term of this patent is extended or adjusted under 35 U.S.C. 154(b) by 294 days.

This patent is subject to a terminal disclaimer.

(21) Appl. No.: 18/353,867

(22) Filed: Jul. 17, 2023

(65) Prior Publication Data

US 2023/0372009 A1 Nov. 23, 2023

Related U.S. Application Data

(63) Continuation-in-part of application No. 18/046,784, filed on Oct. 14, 2022, now Pat. No. 12,408,976, and
(Continued)

(51) Int. Cl.
*A61B 18/14* (2006.01)
*A61B 17/00* (2006.01)
*A61B 18/00* (2006.01)

(52) U.S. Cl.
CPC .............................. *A61B 18/1492* (2013.01); *A61B 2017/00154* (2013.01); *A61B 2018/00267* (2013.01);
(Continued)

(58) Field of Classification Search
CPC ................ A61B 18/00; A61B 18/1492; A61B 2018/00577; A61B 2018/00839;
(Continued)

(56) References Cited

U.S. PATENT DOCUMENTS 4,060,087 A 11/1977 Hiltebrandt et al.
5,526,810 A 6/1996 Wang
(Continued)

FOREIGN PATENT DOCUMENTS

CN 115137475 A 10/2022
EP 1210023 B1 1/2012
(Continued)

OTHER PUBLICATIONS

Turovskiy et al.; U.S. Appl. No. 19/192,289 entitled "Mapping and ablation applicators for treating cardiac tissues," filed Apr. 28, 2025.
(Continued)

*Primary Examiner* — Michael F Peffley
(74) *Attorney, Agent, or Firm* — Shay Glenn LLP

(57) ABSTRACT

Methods and apparatuses are disclosed for providing pulsed electrical treatment (including high voltage, sub-microsecond pulsed electric energy) to tissue, including cardiac tissue. The apparatus may include deployable electrodes that conform to transitional surfaces. These apparatuses may include single or multiple tiers of wire loops forming petal-like electrodes.

30 Claims, 39 Drawing Sheets

Related U.S. Application Data a continuation-in-part of application No. PCT/US2022/020887, filed on Mar. 18, 2022.

(60) Provisional application No. 63/253,119, filed on Oct. 6, 2021, provisional application No. 63/180,022, filed on Apr. 26, 2021.

(52) U.S. Cl.
CPC .............. *A61B 2018/00577* (2013.01); *A61B 2018/00839* (2013.01); *A61B 2018/1467* (2013.01)

(58) Field of Classification Search
CPC .. A61B 2018/00214; A61B 2018/0022; A61B 2018/00267; A61B 2018/00285; A61B 2018/00375; A61B 2018/00613; A61B 2018/1467; A61B 2018/00083; A61B 2018/00184; A61B 2018/00351; A61B 2017/00154; A61B 2090/3966; A61B 90/39
USPC ......................................................... 606/46
See application file for complete search history.

(56) References Cited

U.S. PATENT DOCUMENTS

| | | | |
|---|---|---|---|
| 5,658,280 A | | 8/1997 | Issa |
| 5,782,239 A * | | 7/1998 | Webster, Jr. ........... A61B 5/287 |
| | | | 600/374 |
| 5,991,650 A | | 11/1999 | Swanson et al. |
| 6,033,397 A | | 3/2000 | Laufer et al. |
| 6,267,781 B1 | | 7/2001 | Tu |
| 6,326,177 B1 | | 12/2001 | Schoenbach et al. |
| 6,527,769 B2 | | 3/2003 | Langberg et al. |
| 6,628,976 B1 | | 9/2003 | Fuimaono et al. |
| 6,660,003 B1 | | 12/2003 | DeVore et al. |
| 6,771,996 B2 | | 8/2004 | Bowe et al. |
| 6,987,995 B2 | | 1/2006 | Drysen |
| 7,118,569 B2 | | 10/2006 | Snay et al. |
| 7,142,903 B2 | | 11/2006 | Rodriguez et al. |
| 7,704,249 B2 | | 4/2010 | Woloszko et al. |
| 7,717,910 B2 | | 5/2010 | Goble |
| 7,850,685 B2 | | 12/2010 | Kunis et al. |
| 7,996,085 B2 | | 8/2011 | Levin |
| 8,000,813 B2 | | 8/2011 | Schoenbach et al. |
| 8,086,293 B2 | | 12/2011 | Boseck et al. |
| 8,224,416 B2 * | | 7/2012 | de la Rama ........... A61B 5/287 |
| | | | 606/41 |
| 8,273,084 B2 | | 9/2012 | Kunis et al. |
| 8,280,477 B2 | | 10/2012 | Lau et al. |
| 8,308,720 B2 | | 11/2012 | Davies |
| 8,337,492 B2 | | 12/2012 | Kunis et al. |
| 8,406,875 B2 | | 3/2013 | Levin et al. |
| 8,475,449 B2 | | 7/2013 | Werneth et al. |
| 8,486,063 B2 * | | 7/2013 | Werneth ............. A61B 18/1492 |
| | | | 606/41 |
| 8,512,334 B2 | | 8/2013 | Nuccitelli et al. |
| 8,562,600 B2 | | 10/2013 | Kirkpatrick et al. |
| 8,571,626 B2 | | 10/2013 | Lau et al. |
| 8,617,145 B2 | | 12/2013 | Longoria |
| 8,617,152 B2 | | 12/2013 | Werneth et al. |
| 8,617,156 B2 | | 12/2013 | Werneth et al. |
| 8,641,704 B2 | | 2/2014 | Werneth et al. |
| 8,682,410 B2 | | 3/2014 | Wemeth et al. |
| 8,706,260 B2 | | 4/2014 | Stewart et al. |
| 8,805,466 B2 | | 8/2014 | Salahich et al. |
| 8,822,222 B2 | | 9/2014 | Beebe et al. |
| 8,834,464 B2 | | 9/2014 | Stewart et al. |
| 8,929,969 B2 | | 1/2015 | Gillis et al. |
| 9,005,194 B2 | | 4/2015 | Oral et al. |
| 9,101,764 B2 | | 8/2015 | Nuccitelli et al. |
| 9,149,198 B2 | | 10/2015 | Werneth et al. |
| 9,211,132 B2 | | 12/2015 | Bowman |
| 9,220,555 B2 | | 12/2015 | Asconeguy et al. |
| 9,308,040 B2 | | 4/2016 | Longoria |
| 9,345,540 B2 | | 5/2016 | Mallin et al. |
| 9,351,789 B2 * | | 5/2016 | Novichenok ...... A61B 18/1492 |
| 9,370,311 B2 * | | 6/2016 | Stewart .................. A61B 5/297 |
| 9,387,031 B2 | | 7/2016 | Stewart et al. |
| 9,387,035 B2 | | 7/2016 | Werneth et al. |
| 9,439,721 B2 | | 9/2016 | Werneth et al. |
| 9,554,848 B2 | | 1/2017 | Stewart et al. |
| 9,566,113 B2 | | 2/2017 | Werneth et al. |
| 9,636,093 B2 | | 5/2017 | Longoria |
| 9,655,677 B2 | | 5/2017 | Salahieh et al. |
| 9,713,730 B2 | | 7/2017 | Mathur et al. |
| 9,724,155 B2 | | 8/2017 | Nuccitelli et al. |
| 9,757,182 B2 | | 9/2017 | Bustan et al. |
| 9,757,194 B2 | | 9/2017 | Werneth et al. |
| 9,801,681 B2 | | 10/2017 | Laske et al. |
| 9,848,833 B2 | | 12/2017 | Govari et al. |
| 9,877,780 B2 | | 1/2018 | Longoria |
| 10,064,678 B2 | | 9/2018 | Corvi et al. |
| 10,080,602 B2 | | 9/2018 | Wittkampf |
| 10,130,423 B1 | | 11/2018 | Viswanathan et al. |
| 10,154,888 B2 | | 12/2018 | Sagon et al. |
| 10,213,248 B2 | | 2/2019 | Bar-Tal et al. |
| 10,271,893 B2 | | 4/2019 | Stewart et al. |
| 10,433,904 B2 | | 10/2019 | Werneth et al. |
| 10,433,908 B2 | | 10/2019 | Viswanathan et al. |
| 10,485,609 B2 | | 11/2019 | Palushi et al. |
| 10,531,810 B2 | | 1/2020 | Srivathsan |
| 10,568,679 B2 | | 2/2020 | Bustan et al. |
| 10,603,503 B2 | | 3/2020 | Pakhomov et al. |
| 10,695,557 B1 | | 6/2020 | Townley et al. |
| 10,722,302 B2 | | 7/2020 | Sherman et al. |
| 10,792,097 B2 | | 10/2020 | Ziv-Ari et al. |
| 10,842,401 B2 | | 11/2020 | Trayanova et al. |
| 10,842,561 B2 | | 11/2020 | Viswanathan et al. |
| 10,850,095 B2 | | 12/2020 | Ebbers et al. |
| 10,973,429 B2 | | 4/2021 | Cheng et al. |
| 11,020,179 B2 | | 6/2021 | Viswanathan et al. |
| 11,020,589 B2 | | 6/2021 | Syed et al. |
| 11,065,047 B2 | | 7/2021 | Pare et al. |
| 11,103,299 B2 | | 8/2021 | Bar-Tal et al. |
| 11,167,125 B2 | | 11/2021 | Moss et al. |
| 11,278,349 B2 | | 3/2022 | Stewart et al. |
| 11,295,835 B2 | | 4/2022 | Ingel et al. |
| 11,446,082 B2 | | 9/2022 | Blanck et al. |
| 11,471,208 B2 | | 10/2022 | Waldstreicher et al. |
| 11,497,541 B2 | | 11/2022 | Pare et al. |
| 11,504,184 B2 | | 11/2022 | Cadouri |
| 11,547,851 B2 | | 1/2023 | Krimsky et al. |
| 11,553,962 B2 | | 1/2023 | Harlev et al. |
| 11,633,230 B2 | | 4/2023 | Stewart et al. |
| 11,642,064 B2 | | 5/2023 | Sterrett et al. |
| 11,779,397 B2 | | 10/2023 | Korett et al. |
| 2001/0025177 A1 | | 9/2001 | Woloszko et al. |
| 2004/0181252 A1 | | 9/2004 | Boyle et al. |
| 2005/0261672 A1 | | 11/2005 | Deem et al. |
| 2010/0057072 A1 | | 3/2010 | Roman et al. |
| 2011/0028962 A1 | | 2/2011 | Werneth et al. |
| 2011/0092973 A1 | | 4/2011 | Nuccitelli et al. |
| 2013/0012866 A1 | | 1/2013 | Deem et al. |
| 2013/0030430 A1 | | 1/2013 | Stewart et al. |
| 2014/0142564 A1 | | 5/2014 | Werneth et al. |
| 2014/0364797 A1 | | 12/2014 | Schoenbach et al. |
| 2015/0201991 A1 | | 7/2015 | Zemlin |
| 2016/0058459 A1 | | 3/2016 | Bowman |
| 2016/0354146 A1 | | 12/2016 | Werneth et al. |
| 2017/0027640 A1 | | 2/2017 | Kunis et al. |
| 2017/0065339 A1 | | 3/2017 | Mickelsen |
| 2017/0095362 A1 | | 4/2017 | Boyle et al. |
| 2017/0151014 A1 | | 6/2017 | Perfler |
| 2017/0245928 A1 | | 8/2017 | Xiao et al. |
| 2018/0078755 A1 | | 3/2018 | Kreis et al. |
| 2018/0116539 A1 * | | 5/2018 | Olson .................... A61B 5/287 |
| 2018/0140314 A1 | | 5/2018 | Goyal et al. |
| 2018/0140315 A1 | | 5/2018 | Bowman et al. |
| 2018/0193045 A1 | | 7/2018 | Bowman |
| 2018/0228537 A1 | | 8/2018 | Dong et al. |
| 2019/0201089 A1 | | 7/2019 | Waldstreicher et al. |

(56) References Cited

U.S. PATENT DOCUMENTS

| | | |
|---|---|---|
| 2019/0282116 A1 | 9/2019 | Olson et al. |
| 2019/0336757 A1 | 11/2019 | Rodriguez et al. |
| 2020/0008870 A1 | 1/2020 | Gruba et al. |
| 2020/0129230 A1 | 4/2020 | Forsyth et al. |
| 2020/0155227 A1 | 5/2020 | Cao et al. |
| 2020/0214635 A1 | 7/2020 | Dahlen et al. |
| 2020/0289185 A1 | 9/2020 | Forsyth et al. |
| 2020/0316376 A1 | 10/2020 | Rodriguez et al. |
| 2020/0345262 A1 | 11/2020 | Selkee et al. |
| 2020/0360084 A1 | 11/2020 | Corvi et al. |
| 2021/0007794 A1 | 1/2021 | Martin et al. |
| 2021/0161582 A1 | 6/2021 | Byrd et al. |
| 2021/0236815 A1 | 8/2021 | Waldstreicher et al. |
| 2021/0236816 A1 | 8/2021 | Waldstreicher et al. |
| 2021/0251681 A1 | 8/2021 | Salahieh et al. |
| 2021/0259765 A1 | 8/2021 | Narayan |
| 2021/0267677 A1 | 9/2021 | Stewart et al. |
| 2021/0290941 A1 | 9/2021 | Fischer et al. |
| 2021/0315639 A1 | 10/2021 | Manucherhabadi et al. |
| 2021/0353938 A1 | 11/2021 | Rodriguez et al. |
| 2021/0361341 A1 | 11/2021 | Neal et al. |
| 2021/0393312 A1 | 12/2021 | Davalos et al. |
| 2022/0000548 A1 | 1/2022 | Mickelsen et al. |
| 2022/0080192 A1 | 3/2022 | Sano et al. |
| 2022/0104875 A1 | 4/2022 | Gleiman et al. |
| 2022/0133401 A1 | 5/2022 | O'Brien et al. |
| 2022/0151688 A1 | 5/2022 | Garcia et al. |
| 2022/0168043 A1 | 6/2022 | Stewart et al. |
| 2022/0211426 A1 | 7/2022 | Oklu |
| 2022/0249151 A1 | 8/2022 | Forrest et al. |
| 2022/0280228 A1 | 9/2022 | Forstyn et al. |
| 2022/0323739 A1 | 10/2022 | Mickelsen |
| 2022/0362549 A1 | 11/2022 | Sano et al. |
| 2022/0370125 A1 | 11/2022 | Schweitzer et al. |
| 2022/0370792 A1 | 11/2022 | de la Rama et al. |
| 2022/0387095 A1 | 12/2022 | Neal et al. |
| 2022/0395323 A1 | 12/2022 | Waldstreicher et al. |
| 2023/0026265 A1 | 1/2023 | Shuros et al. |
| 2023/0034970 A1 | 2/2023 | Cheng et al. |
| 2023/0035917 A1 | 2/2023 | Gutbord et al. |
| 2023/0068059 A1 | 3/2023 | Turovskiy et al. |
| 2023/0075838 A1 | 3/2023 | Govari et al. |
| 2023/0087254 A1 | 3/2023 | Seith et al. |
| 2023/0105390 A1 | 4/2023 | Gutbrod et al. |
| 2023/0105973 A1 | 4/2023 | Gutbrod et al. |
| 2023/0172659 A1 | 6/2023 | Olson et al. |
| 2023/0240745 A1 | 8/2023 | van Schelven et al. |
| 2023/0241100 A1 | 8/2023 | Werneth et al. |
| 2023/0310069 A1 | 10/2023 | Stewart et al. |
| 2023/0310072 A1 | 10/2023 | Stewart et al. |
| 2023/0340453 A1 | 10/2023 | Amorese et al. |
| 2024/0065755 A1 | 2/2024 | Ebrahimi et al. |
| 2024/0215893 A1 | 7/2024 | Van Niekerk et al. |

FOREIGN PATENT DOCUMENTS

| | | |
|---|---|---|
| JP | 2017012750 A | 1/2017 |
| JP | 2019513032 A | 5/2019 |
| JP | 2019516455 A | 6/2019 |
| WO | WO2006/041881 A2 | 4/2006 |
| WO | WO2006/078863 A2 | 7/2006 |
| WO | WO2008/009972 A2 | 1/2008 |
| WO | WO2018/201037 A1 | 11/2018 |
| WO | WO2020/014182 A1 | 1/2020 |
| WO | WO2020/121053 A1 | 6/2020 |
| WO | WO2022/040292 A1 | 2/2022 |
| WO | WO2022/066768 A1 | 3/2022 |
| WO | WO2022/109431 A1 | 5/2022 |
| WO | WO2022/171142 A1 | 8/2022 |
| WO | WO2022/192522 A1 | 9/2022 |
| WO | WO2022/231726 A1 | 11/2022 |
| WO | WO2022/260723 A1 | 12/2022 |
| WO | WO2023/009586 A1 | 2/2023 |
| WO | WO2023/017443 A2 | 2/2023 |
| WO | WO2023/026106 A1 | 3/2023 |
| WO | WO2023/044124 A1 | 3/2023 |
| WO | WO2023/114588 A1 | 6/2023 |
| WO | WO2023/172555 A1 | 9/2023 |
| WO | WO2023/172773 A1 | 9/2023 |
| WO | WO2023/192056 A1 | 10/2023 |
| WO | WO2023/192822 A1 | 10/2023 |
| WO | WO2023/192858 A1 | 10/2023 |
| WO | WO2023/192863 A1 | 10/2023 |
| WO | WO2024/081897 A1 | 4/2024 |

OTHER PUBLICATIONS

Aryana et al.; Preclinical Evaluation of a Novel Single-Shot Pulsed Field Ablation System for Pulmonary Vein and Atrial Ablation; medRxiv; J. Cardiovasc. Electrophysiol; 2023;34; pp. 2203-2212; DOI: 10.1111/jce.16010; Jul. 2023.

Ahlberg; Stretchable balloon electronics get to the heart of cardiac medicine; Illinois News Bureau; 4 pages; retrieved from the internet (https://news.illinois.edu/view/6367/205392) on Jan. 19, 2023.

Dicardiology>Com; Flexible Electronics Mounted on Balloons May Improve Cardiac Catheter Ablation Procedures; 3 pages; retrieved from the internet (https://www.dicardiology.com/content/flexible-electronics-mounted-balloons-may-improve-cardiac-catheter-ablation-procedures) on Jan. 19, 2023.

Intellamap Orion; Mapping Catheter; Boston Scientific; 3 pages; retrieved from the interent (https://www.bostonscientific.com/en-US/products/catheters--mapping/orion.html) on Jan. 19, 2023.

International Search Report and Written Opinion mailed Sep. 8, 2022 for PCT/US2022/020887; 17 pages.

Invitation to Pay Additional Fees And, Where Applicable, Protest Fee mailed Jul. 18, 2022 for PCT/US2022/020887; 14 pages.

Lee et al.; Catheter-based systems with integrated stretchable sensors and conductors in cardiac electrophysiology; Proceedings of the IEEE; 103(4); pp. 682-689; May 19, 2015.

Liu et al.; Electronic skin from high-throughput fabrication of intrinsically stretchable lead zirconate titanate elastomer; Research; vol. 2020; 11 pages; Oct. 17, 2020.

Stern; Electronic skin: from flexibility to a sense of touch; Nature; vol. 591; pp. 685-687; Mar. 25, 2021.

Thakur et al.; Flexible Electronic Skin; International Journal of Current Engineering and Technology; 4(6); pp. 4041-4046; Dec. 2021.

Yang et al.; Electronic skin: recent progress and future prospects for skin?attachable devices for health monitoring, robotics, and pros-thetics; Advanced Materials; 31(48); 1904765; Nov. 2019.

Berte et al.; Impact of micro-, mini-and multi-electrode mapping on ventricular substrate characterisation; Arrhythmia & electrophysiology review; 9(3); pp. 128-135; Nov. 2020 (14 pages).

Conti et al.; Comparison between standard and high-definition multi-electrode mapping catheter in ventricular tachycardia ablation; Journal of Cardiovascular Development and Disease; 9(8); pp. 232; Jul. 22, 2022 (15 pages).

International Search Report and Written Opinion mailed Feb. 26, 2024 for PCT/US2023/076866; 18 pages.

Turovskiy et al.; U.S. Appl. No. 18/423,280 entitled "Multi-strut ablation and sensing catheter devices and methods," filed Jan. 25, 2024.

Turovskiy et al.; U.S. Appl. No. 19/298,163 entitled "Circumfer-ential ablation devices and methods," filed Aug. 12, 2025.

Turovskiy et al.; U.S. Appl. No. 19/310,721 entitled "Mapping and ablation applicators and methods of their use" filed Aug. 26, 2025.

* cited by examiner

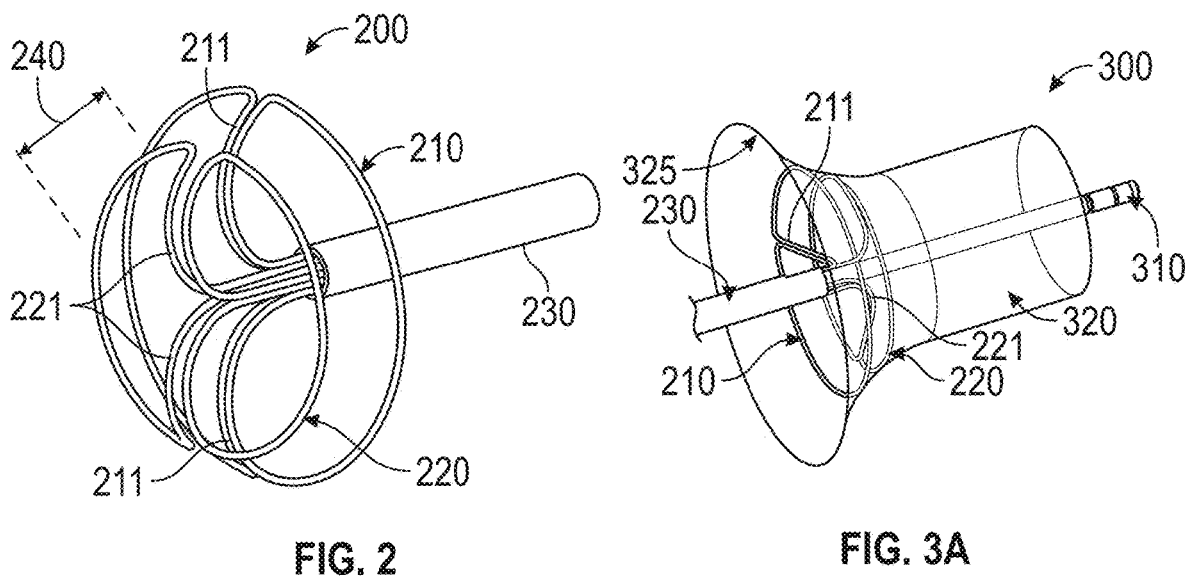
FIG. 2                                      FIG. 3A
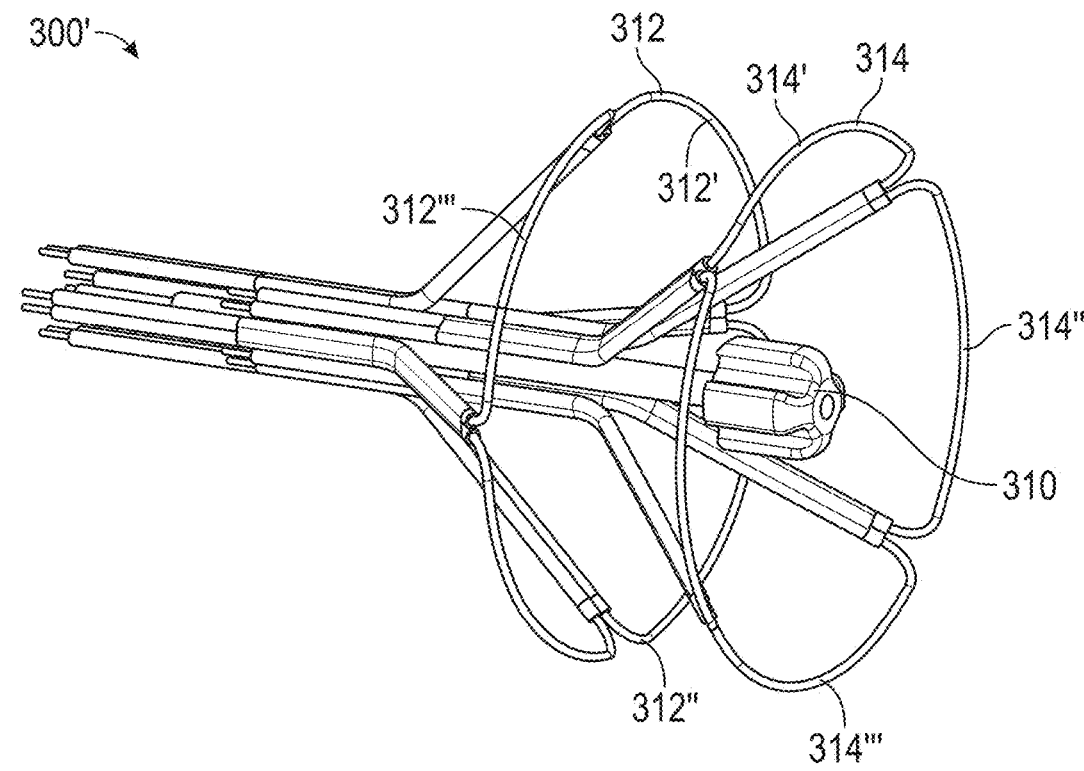
FIG. 3B

460

461

463

465

480

481

483

485

487

491

493

495

500

510

400

410

420

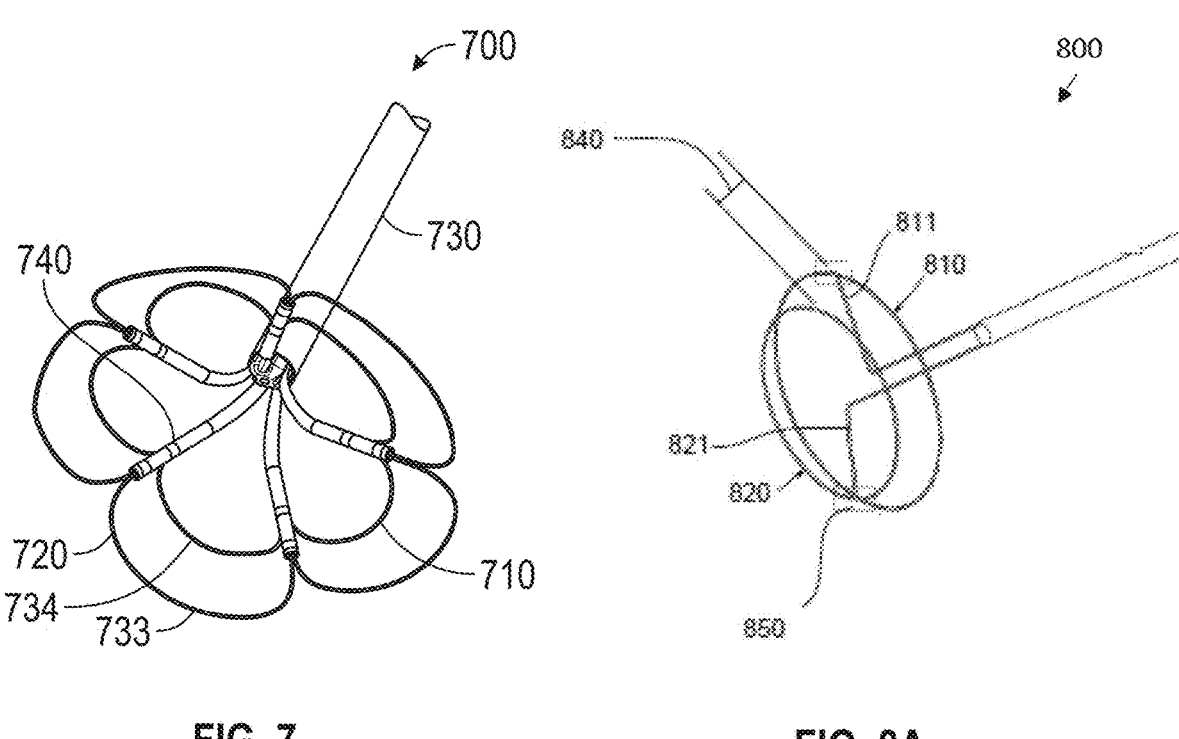
FIG. 7                    FIG. 8A
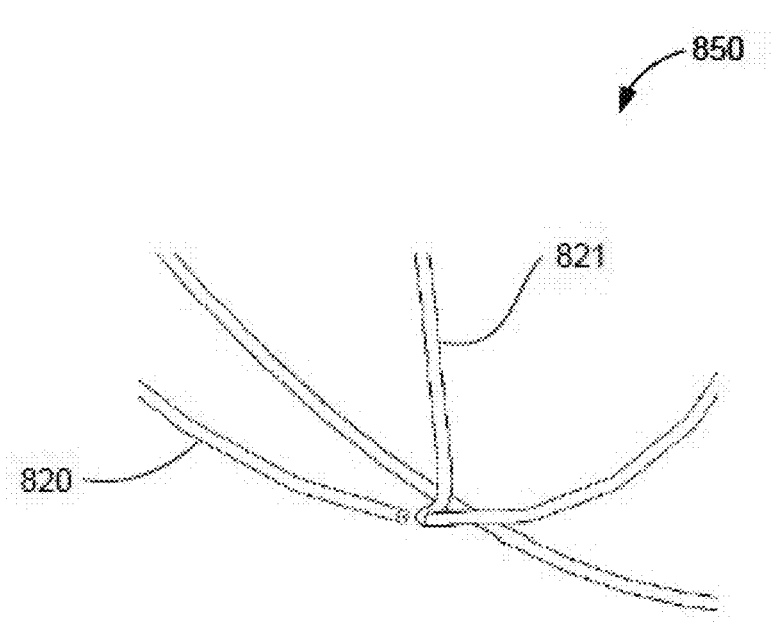
FIG. 8B

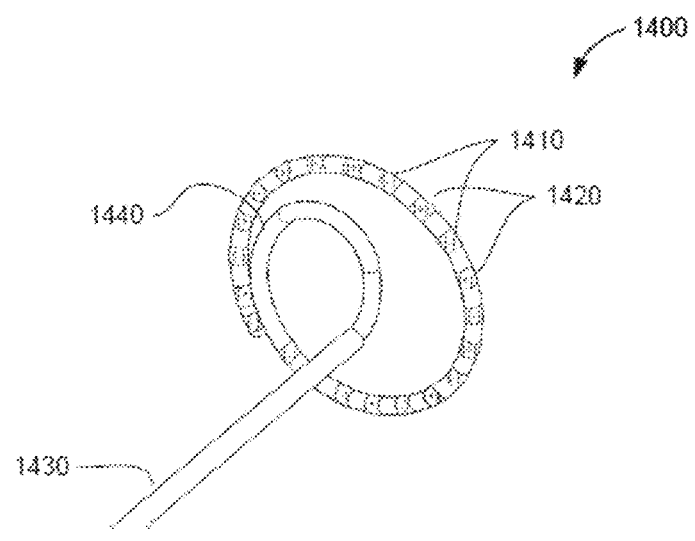
Fig. 14
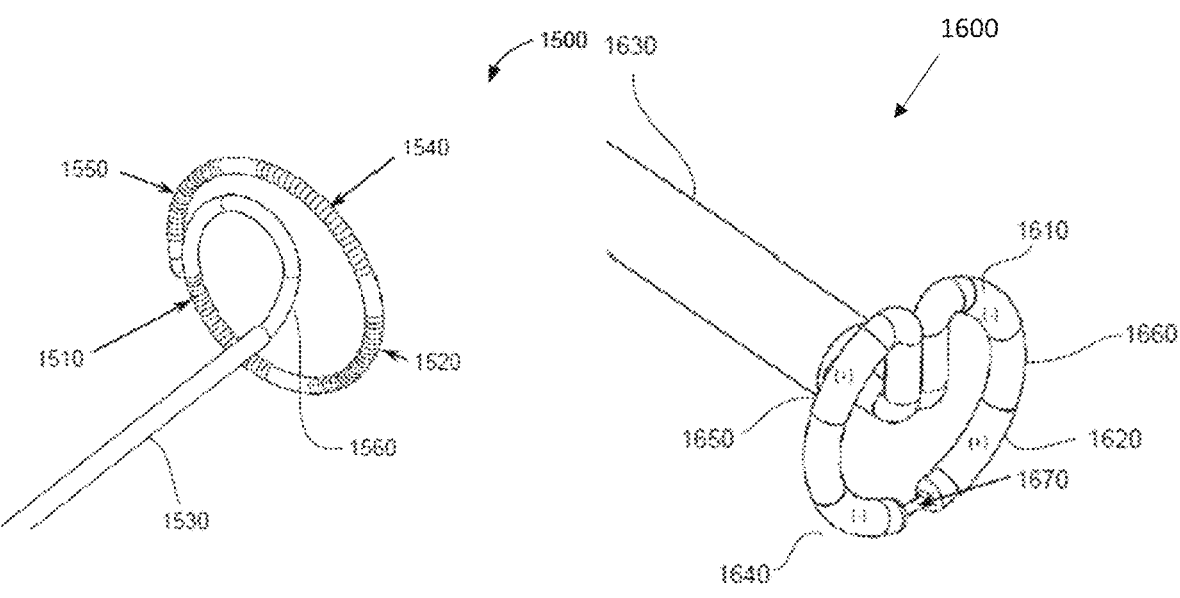
Fig. 15             Fig. 16

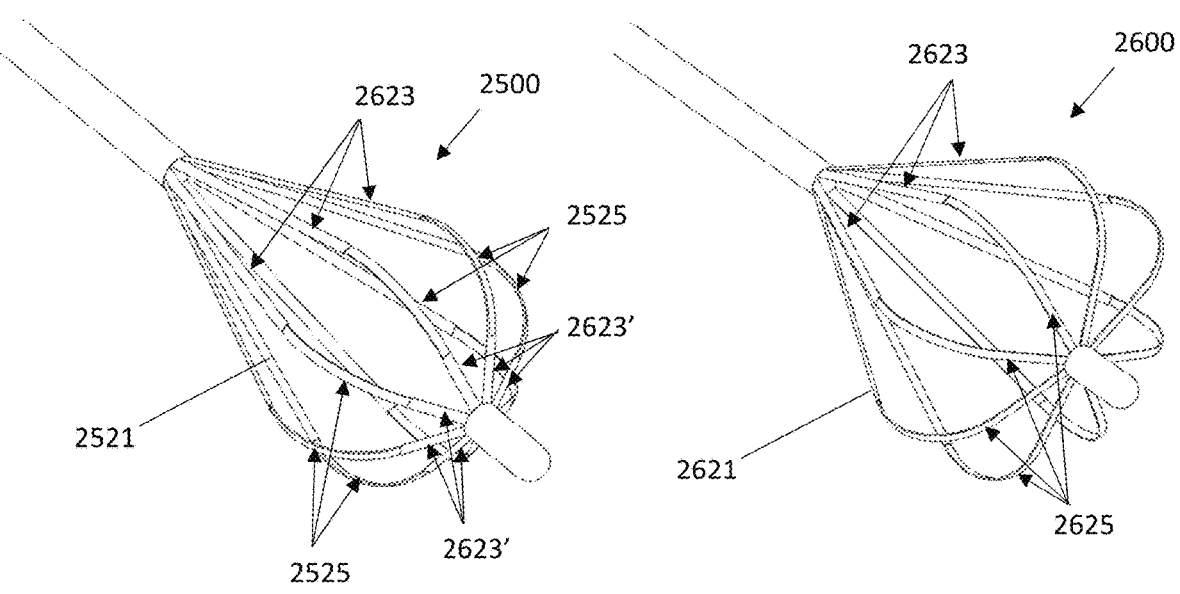
FIG. 25                    FIG. 26
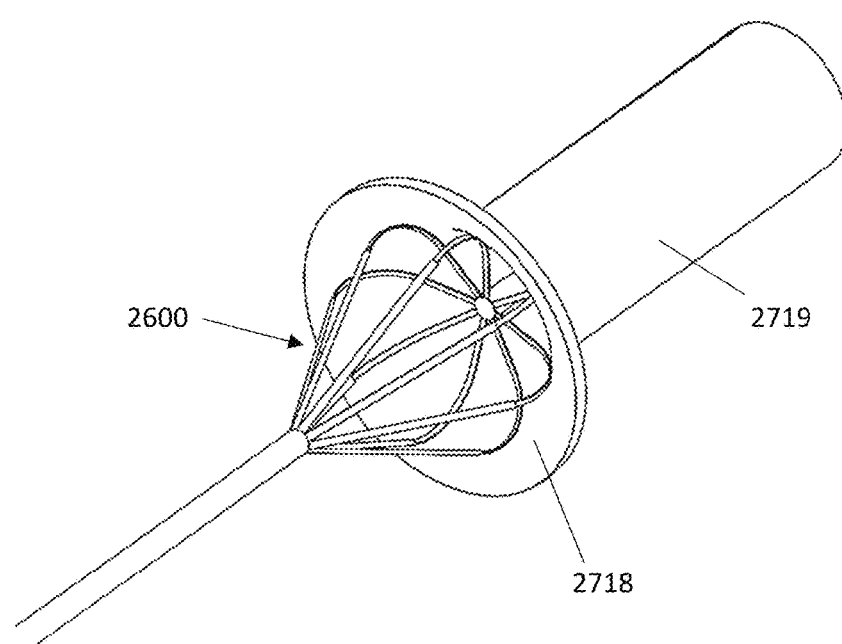
FIG. 27

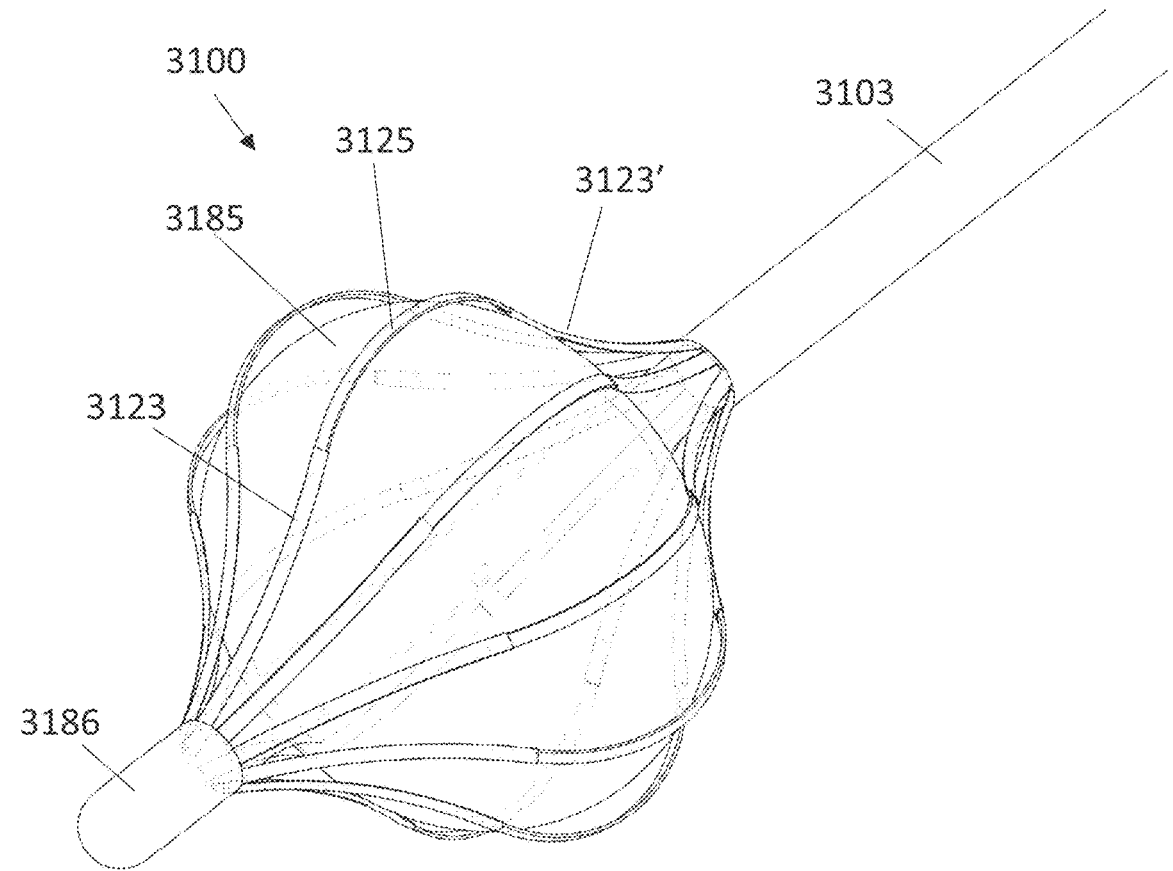
FIG. 31
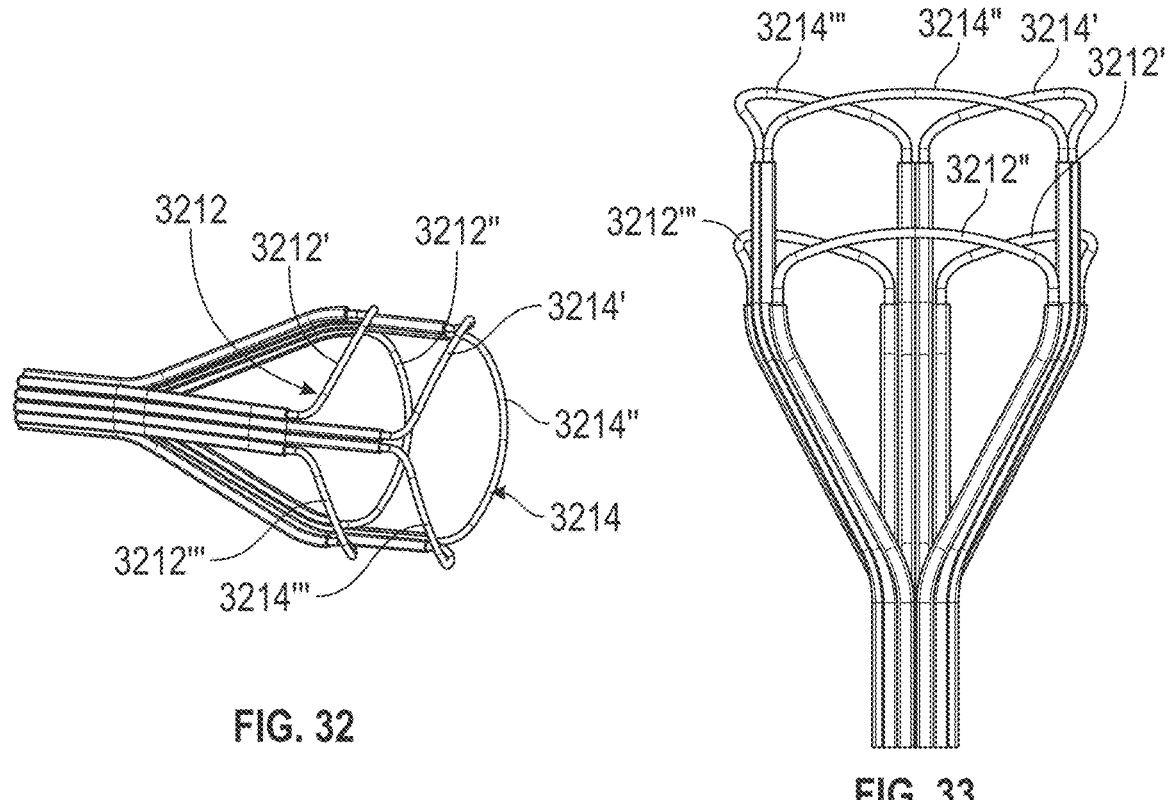
FIG. 32
FIG. 33

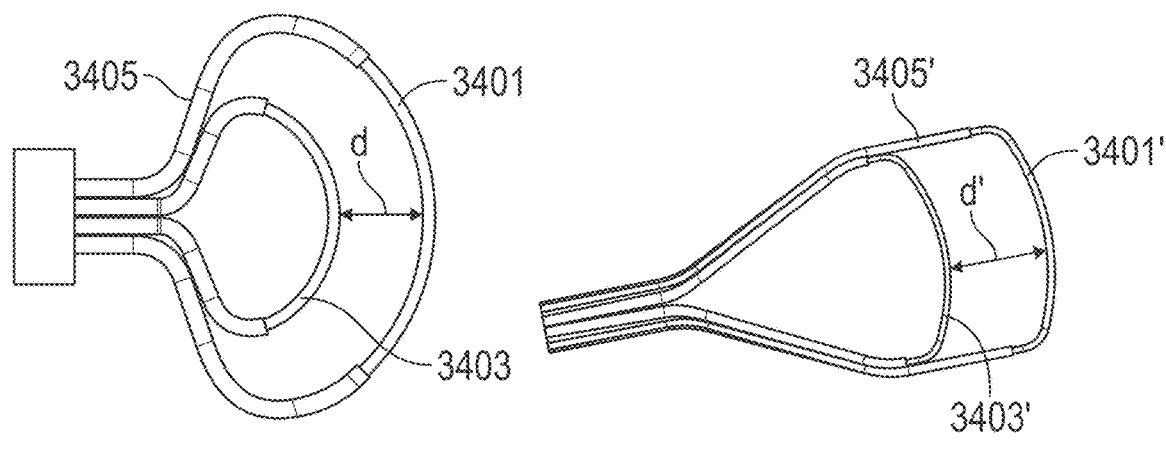
FIG. 34A
FIG. 34B
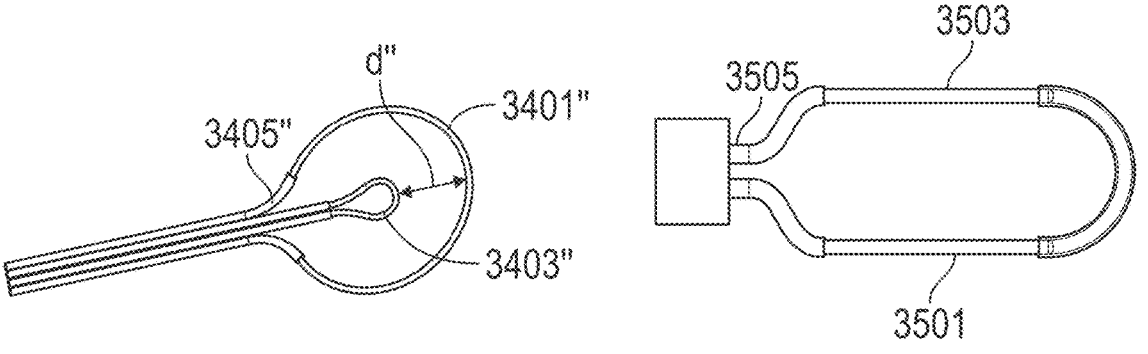
FIG. 34C
FIG. 35
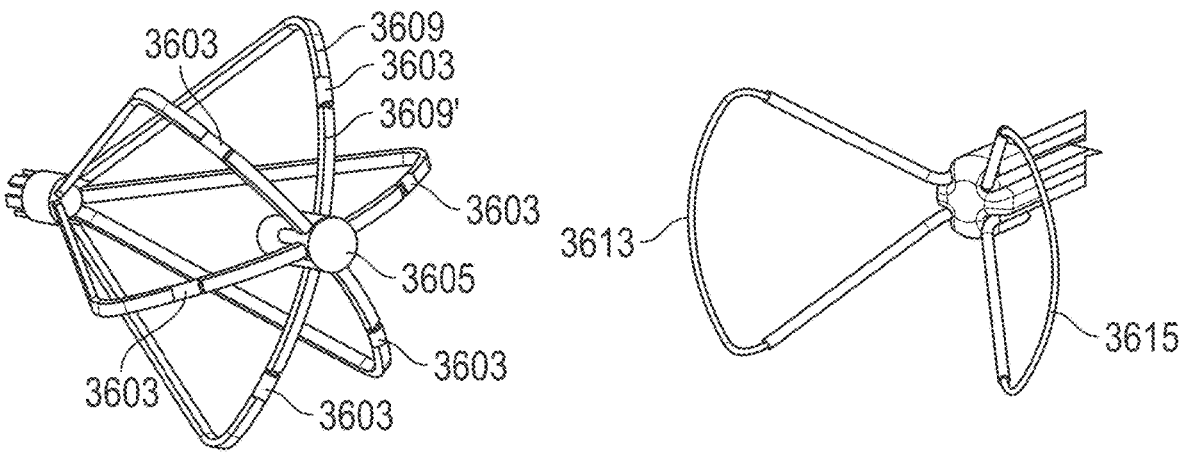
FIG. 36A
FIG. 36B

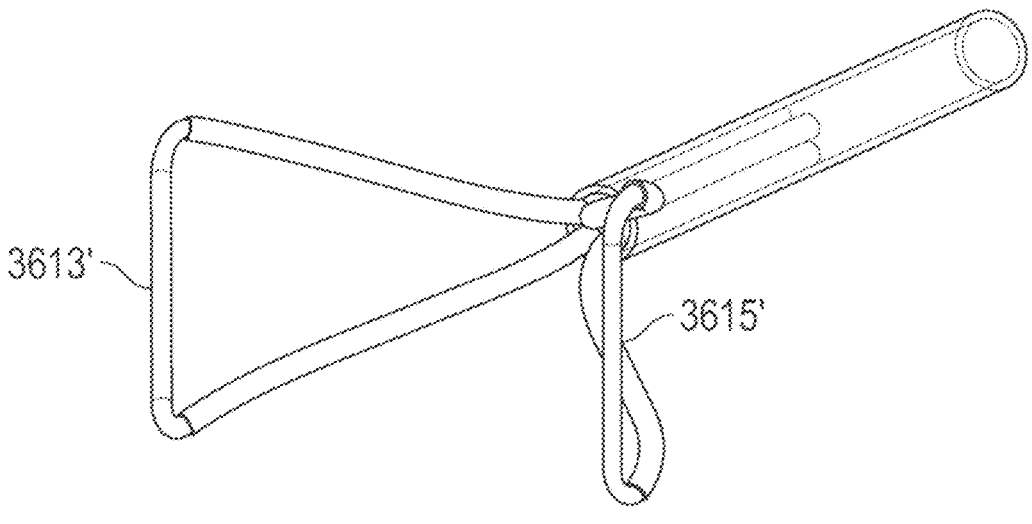
FIG. 36C
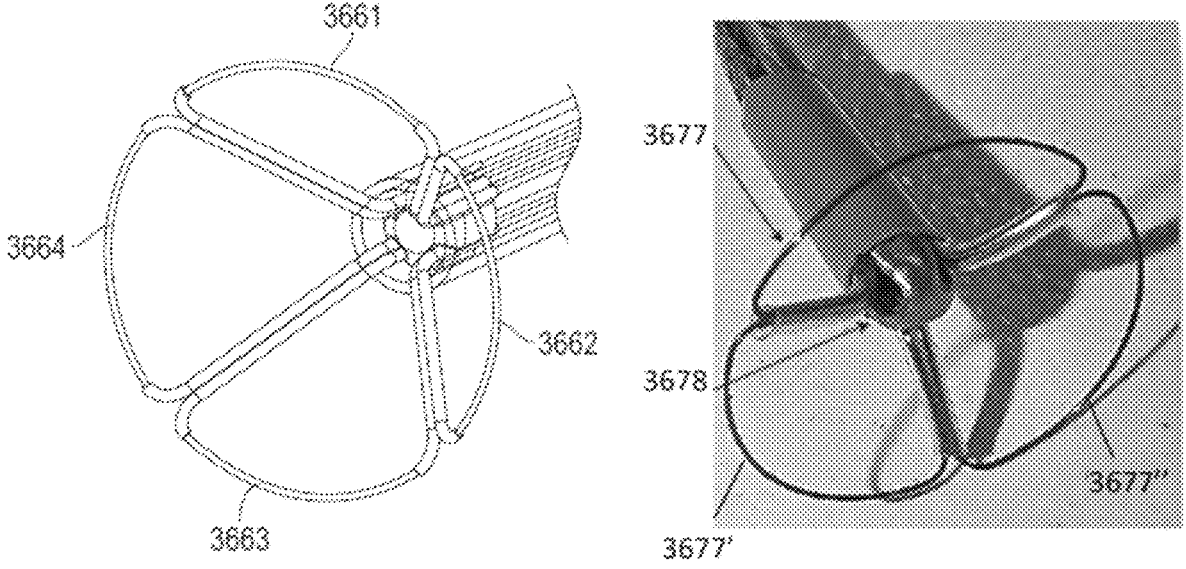
FIG. 36D
FIG. 36E

3708

3700

3706

3840

3800

3803

3814

3812

4200

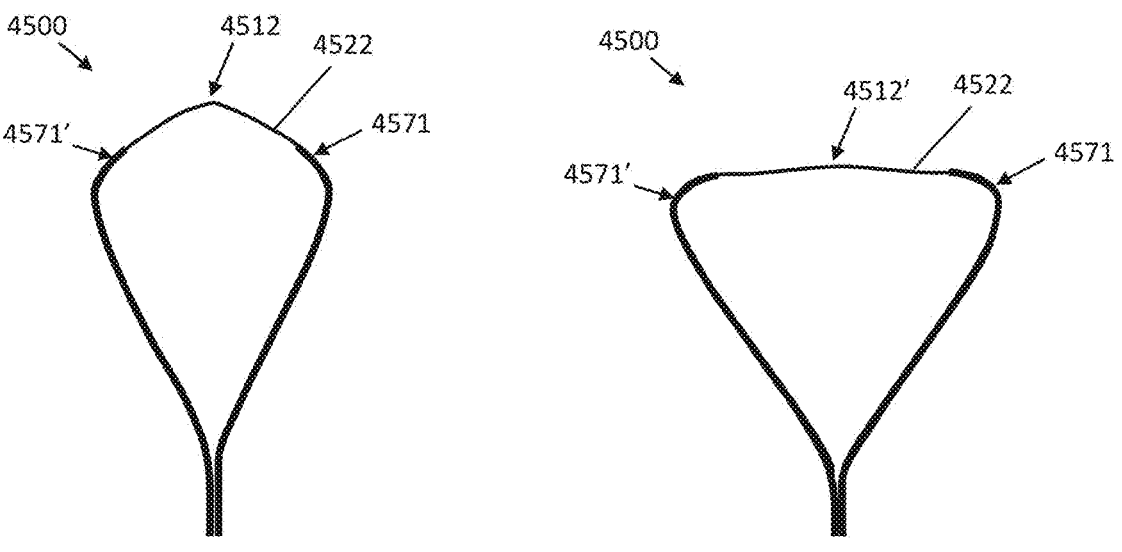
FIG. 45A                    FIG. 45B
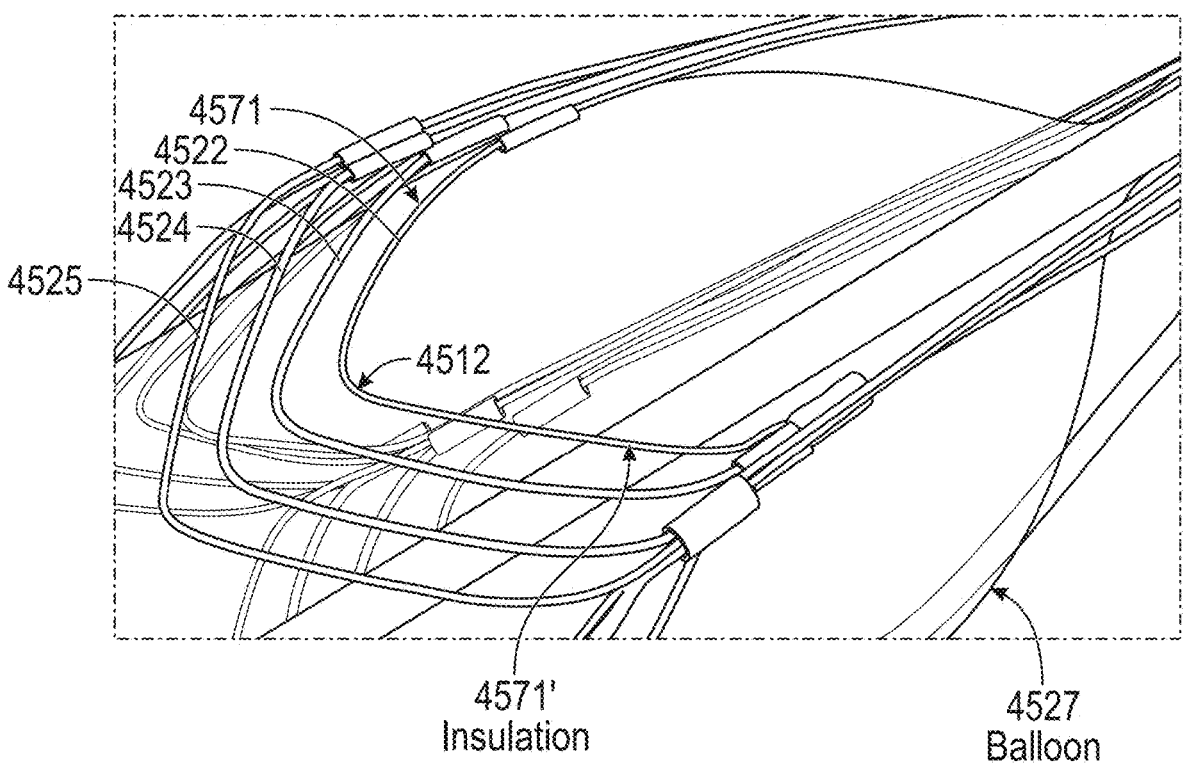
FIG. 45C

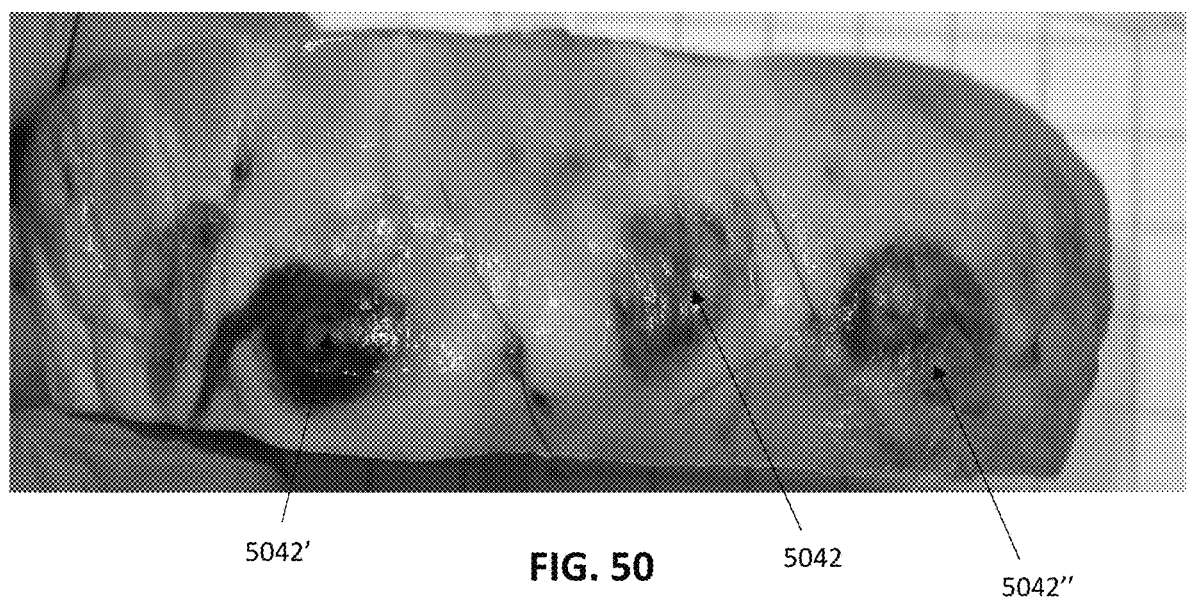
5042'    FIG. 50    5042
                              5042''

MULTI-STRUT ABLATION AND SENSING CATHETER DEVICES AND METHODS

CLAIM OF PRIORITY

This patent application claims priority as a continuation-in-part of PCT Application No. PCT/US2022/020887, filed Mar. 18, 2022, titled "CIRCUMFERENTIAL ABLATION DEVICES AND METHODS," now International Publication No. WO 2022/231726, which claims priority to U.S. Provisional Patent Applications No. 63/180,022, titled "CIRCUMFERENTIAL ABLATION CATHETER DEVICES AND METHODS," filed on Apr. 26, 2021 and No. 63/253,119, titled "CIRCUMFERENTIAL ABLATION CATHETER DEVICES AND METHODS," filed on Oct. 6, 2021; this patent application also claims priority as a continuation-in-part of U.S. patent application Ser. No. 18/046,784, titled "CIRCUMFERENTIAL ABLATION DEVICES AND METHODS," filed on Oct. 14, 2022, now U.S. Patent Application Publication No. US 2023/0068059, each of these patent applications is herein incorporated by reference in its entirety.

BACKGROUND

Short, high-field strength electric pulses have been described for electromanipulation of biological cells. For example, electric pulses may be used in treatment of human cells and tissue. The voltage induced across a cell membrane may depend on the pulse length and pulse amplitude. Pulses longer than about 1 microsecond may charge the outer cell membrane and may lead to permanent opening of pores. Permanent openings may result in instant or near instant cell death. Pulses shorter than about 1 microsecond may affect the cell interior without adversely or permanently affecting the outer cell membrane and result in a delayed cell death with intact cell membranes. Such shorter pulses with a field strength varying in the range, for example, of 10 kV/cm to 100 kV/cm may trigger apoptosis (i.e. programmed cell death) in some or all of the cells exposed to the described field strength and pulse duration. These higher electric field strengths and shorter electric pulses may be useful in manipulating intracellular structures, such as nuclei, endoplasmic reticulum and mitochondria. For example, such sub-microsecond (e.g., nanosecond) high voltage pulse generators have been proposed for biological and medical applications.

In some cases, two or more electrodes are used to deliver electric pulses, including high-field strength electric pulses to a selected treatment area. The two electrodes may be configured for bipolar operation. The electrodes are placed in contact with tissue in the area to receive treatment. In some cases, the treatment area may have a varying or irregular shape. For example, the treatment area may transition from a first diameter to a second diameter. The varying diameters and/or irregular shapes may make it difficult for the electrodes to maintain constant and uniform contact.

Thus, it may be beneficial to provide electrodes that may conform to varying and/or irregularly shaped treatment areas.

SUMMARY OF THE DISCLOSURE

Described herein are medical apparatuses (e.g., devices, systems, etc.) and methods that may be used to perform medical operations to treat patients. Specifically, the apparatuses and methods described herein may be used to deliver short, high-field electric pulses to perform ablation, for example, circumferential ablation on body vessels including blood vessels and other lumina.

For example, described herein are apparatuses and methods for treating the walls of an anatomical structure, such as a body passage, cavity or vessel (e.g., a vein, artery, vessel, heart, trachea, pharynx, larynx, bronchi, ureter, urethra, fallopian tubes, cervix, uterus, intestine (large and/or small), gallbladder, pancreas, rectum, liver, esophagus, stomach, nasal cavity, seminal vesicles, vas deference, etc.) using pulsed electrical fields, including (but not limited to) nanosecond pulsed electrical fields, microsecond pulsed electrical fields, etc. For convenience of the description, all such anatomical structures, cavities, tubes, lumens, passages or vessels will be referred here as a body vessel. In some examples the body vessels may include pulmonary veins, antrums and other appropriate lumina. In particular, the methods and apparatuses described herein may be configured to selectively treat body vessels with varying, transitioning, and/or irregular surfaces. Electrodes that may conform to the body vessels may include a first electrode and a second electrode configured to deploy from a catheter and conform, for example, to a portion of a wall of a body vessel and provide sub-microsecond (e.g., nanosecond) pulsed electrical fields in a localized manner that limits or prevents damage to deeper, non-targeted regions. In general, the electrodes described herein may be equivalently referred to as electrode assemblies; these electrodes (e.g., electrode assemblies) may include one or more active regions configured to apply energy to a tissue and one or more insulated regions.

The methods and apparatuses described herein are not limited to vascular treatments, such as vascular angioplasty treatments, but may be used to treat other body lumen in which lumen narrowing may be a problem. For example, lungs (airways), gastric chambers, ducts, or the like may be treated as described herein. In some examples, the instruments and methods described herein are configured for otolaryngological use, e.g., for insertion and treatment by applying sub-microsecond (e.g., nanosecond) pulsed electrical fields within a lumen or other otolaryngological structure, such as an ear, nose, or throat, including anatomical structures, such as turbinates, tonsils, tongue, soft palate, parotid glands, as well as those structures that connect throat (pharynx) to the stomach. These instruments and devices may be configured for insertion into these structures, for example, they may be configured as an elongate applicator tool, including catheters, tube, etc. sized and shaped to fit within an ear, nose, throat, and/or to treat an associated anatomical structure (e.g., turbinates, tonsils, tongue, soft palate, parotid gland, etc.). For example, described herein are methods and apparatuses configured for the delivery of sub-microsecond (e.g., nanosecond) pulsed electrical fields to a portion of the gastrointestinal tract, e.g., stomach, small intestine, large intestine, duodenum, colon, etc., including, but not limited to the esophagus. Also described herein are methods and apparatuses configured for the delivery of sub-microsecond (e.g., nanosecond) pulsed electrical fields to a portion of the respiratory tract, including the trachea, pharynx, larynx, bronchi and bronchioles. The methods and apparatuses described herein are also especially useful, among other things, in cardiac applications, including but not limited to treatment of atrial fibrillation.

The apparatuses described herein may include elongate applicator tools (e.g., catheters) that may be inserted into a body vessel or lumen, including but not limited to a blood vessel (an artery, a vein, etc.) an esophagus, ear, nose, throat, trachea, pharynx, larynx, small intestine, large intestine, duodenum, colon, etc. These applicator tools may include an elongate, flexible body extending in a proximal-to-distal direction. One or more (e.g., a plurality) of electrodes configured for the delivery of electrical pulses (e.g., nanosecond pulses) to a target tissue may be present at an end region of the flexible body.

The applicator ("applicator tool") may be configured to removably couple to a pulse generator configured to generate, for example, the sub-microsecond (e.g., nanosecond) pulsed energy, such coupling may be through a handle that is proximal to the distal end region including the electrodes. The electrodes may be deployable and may be on an expanding member that expands to contact the vessel wall. The handle may control the deployment. Alternatively, in some cases the applicator tool (also referred herein as apparatus or device) may be configured to couple to the pulse generator directly, without the need for a handle. According to one example, apparatuses described herein comprise medical devices and instruments for use in procedures inserting the applicator tools into a lumen. These apparatuses may be introduced, for example, through an outer delivery catheter or a guiding sheath into a blood vessel.

Any of the apparatuses described herein may be configured to function within a region of the body having diameter that changes (e.g., from wider to narrower, or from narrower to wider), including regions that have a tapering or funnel shape. For example, some of the apparatuses described herein may include at least two ring-shaped (oval, circular, etc.) electrodes having different diameters. In some examples these ring-shaped electrodes may be adjustable in diameter and/or in lateral position relative to each other.

In some examples, the applicator may include one or more contact projections (e.g., ribs, wires, springs, contact plates, contact posts, balloons, etc.) that may be manipulated to extend from the proximal end of the applicator by operation, for example, of the proximal handle to which the applicator tool is coupled. The contact projection may typically contact the wall of the lumen into which the applicator tool is inserted to enhance access and contact with the tissue against the electrodes. For example, the contact projection may be an inflatable element (e.g., balloon) or a mechanical element (e.g., a pair of plates or arms). In some examples multiple contact projections may be positioned along the length of the applicator and may be moved closer or farther apart along the length of the applicator distal end region. In some examples the contact projection(s) flank the electrodes; in some examples the contact projection(s) include the electrodes. The contact projections may be retractable/removable into the applicator tool, or simply relative to the applicator tool.

In one example, the applicator may include an elongate body, such as an elongate catheter body, a first electrode formed of one or more loops and having a first diameter flexibly coupled to the elongate catheter body, and a second electrode formed of one or more different flexible loop having a second diameter flexibly coupled to the elongate catheter body. The first and second electrodes may contact a body vessel, particularly body vessels with irregular, varying, or transitioning surfaces.

In some examples, the first and second electrodes may be divided into lobes, where each lobe is coupled to an elongate body (e.g., the elongate catheter body) with the arms. In some examples, the first and second electrodes may include two or more lobes.

In some examples, the first and second electrodes are coupled to a distal end region of the elongate body (which may be referred to as an elongate catheter body). In further examples, the first and second electrodes may be movable within the elongate catheter body and may be configured to extend out of the elongate catheter body and to collapse when withdrawn into the elongate catheter body. In some other examples, one of the first diameter and the second diameter is smaller than the other. In still other examples, the first electrode is positioned distally with respect to an end of the elongate catheter body (e.g., a distal end of the elongate catheter body) and the second electrode is disposed between the first electrode and the distal end of the elongate catheter body.

In some examples, the first electrode and the second electrodes are configured to flexibly contact an antrum associated with a pulmonary vein. In some other examples, the first conductor and the second conductor are configured to deliver a pulsed electrical treatment, where pulse energy is transferred between the first conductor and the second conductor. In another example, the first conductor and the second conductor are configured to deliver a pulsed electrical treatment, where energy is transferred between the first conductor and a third conductor or between the second conductor and the third conductor.

In some examples, the first conductor and the second conductor are configured to vary a distance therebetween.

In another example, the apparatus for delivering nanosecond pulsed electric fields may include an elongate catheter body, a shape support member coupled to the elongate catheter body configured to form a shape, a conductive braid configured to circumferentially surround the shape support member and form a first electrode, and one or more conductive bands configured to circumferentially surround a portion of the conductive braid and the shape support member and form a second electrode. The apparatus may further comprise a tubular insulative member disposed between the shape support and the conductive braid.

In some examples, the apparatus may further comprise one or more band insulators disposed between the conductive braid and the one or more conductive bands configured to electrically insulate the one or more conductive bands from the conductive braid. Furthermore, the position of the conductive bands may be configured to determine, at least in part, a density of an electric field.

In some other examples, the shape support member may be nickel titanium alloy. Furthermore, the shape support member may conform to a shape of an antrum of a pulmonary vein. In some examples, the conductive braid and the one or more conductive bands may be configured to deliver a bipolar nanosecond pulsed electrical treatment. In another example, the conductive braid and the one or more conductive bands may be configured to deliver a monopolar nanosecond pulsed electrical treatment.

A method for delivering a sub-microsecond pulsed electric field to a body vessel may include positioning an applicator including two or more electrodes within an identified treatment area, placing the two or more electrodes in contact with tissue within the identified treatment area, and applying pulsed electrical treatment via the two or more electrodes. In some examples, placing the two or more electrodes in contract with tissue may include deploying the two or more electrodes from an elongate catheter body. In some other examples, the two or more electrodes may include a first shaped electrode and a second shaped electrode. The first shaped electrode may have a first diameter and the second shaped electrode may have a second diameter, where the first diameter is different than the second diameter.

In some examples, the first shaped electrode may be disposed on a different plane than the second shaped electrode. In some other examples, the first shaped electrode may be coplanar with the second shaped electrode.

In some examples, the pulsed electrical treatment may include an electric field between the two or more electrodes. In another example, the pulsed electrical treatment may include an electric field between at least one of the two or more electrodes and a third electrode.

The apparatuses described herein may generally be configured to safely and reliably deliver microsecond, nanosecond, picosecond, etc. pulses, and may include an electric field with a pulse width of between 0.1 nanoseconds (ns) and less than 1000 nanoseconds, or shorter, such as 1 picosecond, which may be referred to as sub-microsecond pulsed electric field. This pulsed energy may have high peak voltages, such as 1 to 5 kilovolts per centimeter (kV/cm), 10 kV/cm, 20 kV/cm, 100 kV/cm or higher. In some applications, the pulsed energy may be less than 1 kV/cm. Treatment of biological cells may use a multitude of periodic pulses at a frequency ranging from 0.1 per second (Hz) to 100,000 Hz, and may trigger apoptosis, for example, in the in-growing tissue causing restenosis. Selective treatment of vessel walls with high voltage, sub-microsecond pulsed energy can induce apoptosis within the cells that are causing restenosis without substantially affecting normal cells in the surrounding tissue due to its non-thermal nature. A subject may be a patient (human or non-human, including animals). A user may operate the apparatuses described herein on a subject. The user may be a physician (doctor, surgeon, etc.), medical technician, nurse, or other care provider.

Thus, the application of high voltage, fast (e.g., microsecond or sub-microsecond) electrical pulses may include applying a train of electrical pulses having a pulse width, for example, of between 0.1 nanoseconds (ns) and 1000 nanoseconds. Applying high voltage, fast electrical pulses may include applying a train of sub-microsecond electrical pulses having peak voltages of between, for example, 1 kilovolt per centimeter (kV/cm) and 500 kV/cm. Applying high voltage, fast electrical pulses may include applying a train of sub-microsecond electrical pulses at a frequency, for example, of between 0.1 per second (Hz) to 100,000 Hz.

Any of these apparatuses may be used with a pulse generator. For example, described herein are systems for treating tissue that may include: an elongate applicator (e.g. applicator tool) as described herein, a connector, e.g., a high voltage connector adapted to couple the elongate applicator tool to a pulse generator; and a pulse generator configured to generate a plurality of electrical pulses having amplitude of at least 0.1 kV and a duration of less than 1000 nanoseconds, the pulse generator comprising a port configured to connect to the high voltage connector. In some examples the applicator tool includes an elongate body having a distal end region from which one or more electrodes are configured to extend. The distal end may be steerable (e.g., may articulate) in some examples. The apparatuses described herein include devices that may be referred to as applicator tools, and typically include an applicator (or applicator region) at or near a distal end region for applying energy.

As mentioned, any of these apparatuses may be configured so that the proximal end of the applicator tool is adapted to be coupled to a robotic or movable arm, for example, for computer-controlled activation of the set of electrodes. Alternatively, or additionally the proximal end of the applicator tool may be adapted to couple to a handle of the pulse generator which may in turn be adapted for connection to a robotic arm.

In some examples, as described above, the apparatus may be configured to adjust the distance between electrodes for applying the therapy at the distal end region of the applicator. In some examples the applicator includes at least two circumferentially arranged electrodes in which each electrode is circumferentially arranged around a support. The longitudinal position of one or both of the circumferentially arranged electrodes may be adjustable so that the distance between the circumferentially arranged electrodes may be increased or decreased. In some cases, the applicator may be adjustable to adjust the separation between the circumferentially arranged electrodes to be, for example, between 5 mm and 40 mm (e.g., between 10 mm and 20 mm, etc.). The circumferentially arranged electrodes may be an electrode ring (extending fully circumferentially around, or partially circumferentially around) or it may be a plurality of separate electrodes arranged circumferentially around the applicator. Adjusting the spacing between the electrodes may allow the user to adjust and/or correct the placement and fit within the inner wall or antrum, especially when the diameter/size of the vessel changes (including changes rapidly) depending on the longitudinal position. One electrode ring may fit one circumference while the other electrode ring may fit a larger or smaller circumference and the spacing between them may be adjusted in some examples.

In use, any of the apparatuses described herein may be used for applying energy in, including in particular, sub-microsecond (e.g., nanosecond) pulsed fields. Sub-microsecond pulsed electromagnetic fields may induce apoptosis in cellular structures.

For example, described herein are apparatuses (e.g., devices, systems, etc., including electrode applicators) for delivering pulsed electric fields within a body lumen. These apparatuses may include: an elongate body (having an elongate, flexible body); a first electrode comprising a first one or more loops, having a first active region formed on the first one or more loops, wherein the first active region is arranged to circumscribe the body lumen, further wherein the first one or more loops are flexibly coupled to a distal end region of the elongate body; and a second electrode comprising a second one or more loops having a second active region formed from the second one or more loops, wherein the second active region is arranged to circumscribe the body lumen, wherein the second one or more loops are flexibly coupled to a distal end region of the elongate body, further wherein the first electrode is laterally offset from the second electrode along the distal end region of the elongate body.

In any of the apparatuses described herein each electrode of the apparatus may include an elongate active region, from which electrical energy is applied. For example, the active region may be conductive (uninsulated) region of electrically conductive material (e.g., conductive wire, etc.) that is configured to emit electrical energy. In general, the apparatuses described herein may include a first electrode with a first electrically conductive region that is extended across multiple lengths of the different loops forming the first electrode (or in some examples, second). All of the loops (and therefore all of the sub-regions of the loops forming the active region) of the first electrode may be electrically coupled together to form a single anode or a single cathode; and all of the loops forming the second electrode (and therefore all of the sub-regions of the loops) are electrically coupled together as a single anode or single cathode.

In some examples the first electrode includes a single loop; in other examples the first electrode includes a plurality of loops forming the first electrode, that are in electrical communication. Similarly the second electrode may be a single loop or a plurality of different loops.

In any of these apparatuses the first electrode and/or the second electrode may be transverse to the distal end region of the elongate body and/or the second electrode may be transverse to the distal end region of the elongate body. In any of these apparatuses the first electrode and/or the second electrode may include a first plurality of loops arranged as petals around the distal end region of the elongate body. The outer portion of each petal may form the active region for a single electrode. This configuration may allow more robust treatment around the entire periphery of a vessel without requiring multiple reposition steps of electrode pairs to cover the same larger region around the circumference of the vessel.

In general, the first active region of the first electrode may have a diameter that is less than the diameter of the second active region (e.g., the diameter of the loop(s) forming the first electrode and the second active region of the second electrode may have a diameter that are different). In some examples, the diameters of the loops forming the first electrode and the second electrode may be approximately the same.

Any of these apparatuses may include an expandable frame. The expandible frame may be a balloon, a strut assembly, a mesh (e.g., an expandable wire mesh), or the like. In general, the first electrode and the second electrode may be coupled to an outer perimeter of the expandable member so that they may circumscribe, at least partially around the perimeter of the vessel. The expandible frame may support the first active electrode and the second active electrode. Thus, the first electrode and the second electrode may be arranged on the expandable frame. For example, the first electrode and the second electrode may be arranged on expandable balloon.

In any of these examples the first electrode and the second electrode may each be formed of a wire, e.g., a wire having a diameter of less than about 0.2 mm (less than about 0.19 mm, less than about 0.18 mm, less than about 0.17 mm, less than about 0.16 mm, less than about 0.15 mm, etc.).

In general, the first and second electrodes are configured to flexibly conform to body lumen, so that the active regions may extend circumferentially around the perimeter of the lumen. As used herein "arranged or configured to circumscribe the body lumen" may refer to at least partially extending around the circumference of a body lumen (e.g., traveling in an arc of less than 360 degrees, e.g., between about 270 degrees or more, e.g., 300 degrees or more, 320 degrees or more, 330 degrees or more, 340 degrees or more, 340 degrees or more, about 360 degrees). Thus a first active region that is arranged to circumscribe the body lumen may include an active region that extends completely or almost completely around the circumference of the lumen (about 270 degrees around the circumference of the lumen or more, about 300 degrees or more, about 320 degrees or more, about 330 degrees or more, about 340 degrees or more, about 340 degrees or more, about 360 degrees, etc.). In some examples, the first active region is configured to circumscribe the body lumen in a nearly complete circle.

Any of these apparatuses may include an outer catheter or a guiding sheath (e.g., delivery catheter), wherein the elongate body forming or holding the first and second electrodes may be slidably disposed within the outer catheter. The first electrode and the second electrode are configured to collapse when withdrawn or introduced into the outer catheter and/or to expand radially outward when extended out of the distal end of the delivery (outer) catheter.

The first electrode may be positioned distally with respect to the end region of the elongate body and the second electrode is positioned proximal of the first electrode. In some examples the longitudinal positions of the first and second electrodes may be fixed. In some examples the longitudinal positions of the electrodes may be adjustable (e.g., may vary). For example, the first electrode may be configured to slide axially proximally or distally relative to the second electrode.

In some examples the first electrode may comprise an anode and the second electrode may comprise a cathode. The apparatus may be configured to deliver a pulse energy between the first electrode (anode) and the second electrode (cathode).

In any of the examples described herein the first active region and the second active region may each be longer than 5 cm in length. The first active region and the second active region may each have a diameter of less than 0.2 mm.

Also described herein are apparatus for delivering pulsed electric fields comprising: an elongate catheter body; a first electrode comprising as a first wire loop, wherein the first wire loop flexibly extends from the elongate catheter body, further wherein the first electrode has a first active region including at least a portion of the first wire loop and extends greater than 5 cm in length; and a second electrode comprising a second wire loop, wherein the second wire loop flexibly extends from the elongate catheter body, further wherein the second electrode has a second active region including at least a portion of the second wire loop and extends greater than 5 cm in length.

The first active region and the second active region may be spaced apart from each other by a fixed distance in a direction of a long axis of the elongate catheter body. The first and second electrodes may be configured to flexibly conform to body vessels. The first loop may be smaller than the second loop. Alternatively in some examples the first loop is the same size as the second loop.

The first electrode may be positioned distally with respect to a distal end of the elongate catheter body and the second electrode may be positioned between the first electrode and the distal end of the elongate catheter body.

In general, the apparatuses described herein are configured to advantageously apply energy between a first electrode and a second electrode around a circumferential region of a vessel within the body without requiring multiple repositioning steps to treat the entire (or the majority of) the circumference. This solves a problem of many other electrical delivery systems, which rely on multiple discrete active regions that may leave gaps. The apparatuses described herein are particularly well suited, though not limited to such use, for applying nanosecond pulses. Nanosecond pulse energy may act by non-thermally entering cells and altering function of the internal cellular organelles, including the mitochondria and endoplasmic reticulum. For example, nanosecond pulsed electrical fields cause intracellular disruption that leads to regulated cell death. In examples in which the applied energy is nanosecond (or faster) pulsed electrical fields, the active region of each electrode may be long and thin, e.g., formed of a wire, the applied field may result in very littler thermal energy applied, preventing damage to non-cellular tissue.

For example, also described herein are methods for delivering a pulsed electric field to a wall of a body vessel within a subject's body, the method comprising: positioning a first electrode comprising a first one or more wire loops and a second electrode comprising a second one or more wire loops within a body vessel, so that a first active region of the first one or more wire loops is in electrical communication with a first circumference of the wall, and so that the second active region of the second one or more wire loops is in electrical communication with a second circumference of the wall that is longitudinally separated from the first circumference of the wall; and applying a pulsed electrical treatment between the first active region and the second active region.

Positioning the first and the second electrode may comprise deploying the first electrode and the second electrode from a delivery catheter by moving the delivery catheter relative to an elongate body coupled to the first and the second electrodes to expand at least one of the first electrode and the second electrode from a delivery configuration (e.g., an un-deployed state) to a deployed configuration (or deployed state). In some examples deploying the first electrode comprises contacting the wall with a plurality of electrically continuous wire lengths of the first one or more wire loops. In some examples, deploying the second electrode comprises contacting the wall with a plurality of electrically continuous wire lengths of the second one or more wire loops. Deploying the first electrode may include expanding the first electrode to have a larger diameter than the second electrode. In some examples, deploying comprises deploying in the antrum of a pulmonary vein. For example, deploying may comprise deploying the first electrode so that the first electrode is coplanar with the second electrode.

As mentioned, applying the pulsed electrical treatment may include applying an electric field between the first active region and the second active region. In particular, applying the pulsed electrical treatment may comprise applying pulses having a nanosecond duration (less than 1000 ns duration).

Also described herein are apparatuses comprising: an elongate body extending proximally to distally, wherein the elongate body is configured to be inserted into a body vessel; an applicator region at a distal end region of the elongate body comprising a plurality of expandable ribs configured to expand outwards within the body vessel from a collapsed configuration; wherein each rib comprises an un-insulated active region; and further wherein a first subset of the plurality of expandable ribs is configured to have a first polarity and a second subset of the plurality of expandable ribs is configured to have a second polarity.

For example, the un-insulated active region on each of the plurality of ribs may be configured to be substantially straight and parallel to a long axis of a portion of the applicator region. In some implementations the un-insulated active flat region of each rib is also configured to remain the same length during the rib expansion regardless of how much each rib is being expanded. Each of the plurality of ribs may comprise a hinge region on each side of the un-insulated active region. The hinge region may be covered by a flexible insulator.

In some examples, the elongate body may comprise a first elongate member coupled to a proximal end of each rib and a second elongate member coupled to a distal end of each rib, wherein the first elongate member and the second elongate member are configured to slide axially relative to each other to transform the applicator region between the collapsed configuration and an expanded configuration in which the plurality of expandable ribs is expanded outwards.

In any of these apparatuses, each of the expandable ribs may be biased to expand outwards. In any of these apparatuses, the elongate body may be a flexible elongate body; the plurality of expandable ribs may be substantially flat.

Any of these apparatuses may include an inflatable member within the applicator region and configured to expand outwards to drive expansion of the plurality of ribs.

In some examples, the applicator region is configured to expand outwards into a shape having a larger cross-sectional area, relative to a long axis of the applicator region, that is larger, for example, distally than proximally, or in some examples, larger proximally than distally. For example, the applicator region may comprise a teardrop shape.

The un-insulated active region of each rib may be within a distal portion of the applicator region so that the un-insulated active region faces distally in the expanded configuration.

Any of these apparatuses of the present disclosure may include a centering guide extending distally from the applicator region. In some examples, the centering guide may be configured and used as one of the electrodes.

In some examples described herein an apparatus may comprise: an elongate body extending proximally to distally, wherein the elongate body is configured to be inserted into a body vessel; an applicator region at a distal end region of the elongate body comprising a first wire extending distally from the elongate body, the first wire having a first active region that is adjacent to a first insulated region of the first wire, and a second wire extending distally from the elongate body, the second wire having a second active region adjacent to a second insulated region of the second wire; wherein the first active region is separated from the second active region by a minimum distance, d, that is substantially constant along the length of the first active region; and further wherein a first active region is configured to have a first polarity and the second active region is configured to have a second polarity. The first wire may comprise a first loop and the second wire may comprise a second loop that is positioned concentrically relative to or within the first loop. In any of these apparatuses the first wire and the second wire may extend from the elongate body in a plane. In some examples, the insulated region and/or the elongate body may comprise a bend so that the first and second wires extend at an angle to the long axis of the elongate body.

Also described herein are apparatus (e.g. devices, systems, etc.) for delivering pulsed energy either as a point-by-point treatment or as a single shot treatment. Point-by-point treatment generally includes applying area between two smaller electrically active regions, while single shot treatments generally treat larger areas with multiple, electrically coupled active regions. For example, the apparatus may include: an elongate body; a plurality of loops or ribs extending radially outward from the elongate body at a first circumferential position, wherein each loop or rib comprises an uninsulated electrically active region facing radially outward so that the uninsulated electrically active regions encircle the first circumferential position of the elongate body; and an electrical connector configured to switch between a first configuration in which a plurality of the uninsulated electrically active regions are electrically coupled together to apply energy at a first polarity and a second configuration in which the uninsulated electrically active regions are separately activated.

In some examples the electrical connector may electrically couple all of the uninsulated electrically active regions loops or ribs of the plurality of loops or ribs in the first configuration. The electrical connector may be configured so that in the first configuration the connector electrically couples a first subset of the uninsulated electrically active regions loops or ribs of the plurality of loops or ribs to apply energy at a first polarity and a second plurality of loops or ribs that alternate with the loops or ribs of the first plurality of loops or ribs apply energy at a second polarity.

In some examples the apparatus for delivering pulsed energy as either point-by-point or as a single shot may include: an elongate body; a plurality of loops or ribs extending radially outward from the elongate body at a first circumferential position, wherein each loop or rib comprises an uninsulated electrically active region facing radially outward so that the uninsulated electrically active regions encircle the first circumferential position of the elongate body; a second electrically active region that is circumferentially offset from the first circumferential position; and an electrical connector configured to switch between a first configuration in which all of the uninsulated electrically active regions are electrically coupled together and a second configuration in which the uninsulated electrically active regions are separately activated. The second electrically active region may comprise a second plurality of loops or ribs that extend radially outward from the elongate body at a second circumferential position, wherein each loop or rib of the second plurality of loops or ribs comprises an uninsulated electrically active region facing radially outward so that the uninsulated electrically active regions encircle the second circumferential position of the elongate body. The same electrical connector or a separate electrical connector may be configured to switch between a first configuration in which all of the uninsulated electrically active regions of the second plurality of loops or ribs are electrically coupled together and a second configuration in which the uninsulated electrically active regions of the second plurality of loops or ribs are separately activated. In some examples the second electrically active region is a distal-facing electrode extending from a distal end of the elongate body.

For example, described herein are apparatuses for delivering pulsed electric fields to a wall of an anatomical structure, the apparatus comprising: an elongate body; a first electrode comprising a first one or more loops, having a first active region formed on the first one or more loops, wherein the first active region is configured to circumscribe a first region of the wall of the anatomical structure, further wherein the first one or more loops are flexibly coupled to a distal end region of the elongate body; and a second electrode comprising a second one or more loops having a second active region formed from the second one or more loops, wherein the second active region is configured to circumscribe a second region of the wall of the anatomical structure, wherein the second one or more loops are flexibly coupled to the distal end region of the elongate body, further wherein the first electrode is either radially offset, laterally offset or both radially and laterally offset from the second electrode.

Any of the apparatuses described herein may be configured so that the at least one of the first active region and the second active region is configured to circumscribe the wall of the anatomical structure in a partial, nearly complete or complete circle.

Any of these apparatuses may include a plurality of mapping and/or sensing electrodes on a portion of the first and/or second electrode. For example, the sensing and/or mapping electrodes may be radially inward of the first active region and/or the second active region. The sensing and/or mapping electrodes may have a smaller total surface area (e.g., 80% or less, 70% or less, 60% or less, 50% or less, 40% or less, 30% or less, 20% or less, 10% or less, 5% or less, etc.) than the surface area of the electrically active region of either the first and/or second electrically active regions. The sensing and/or mapping electrodes may be electrically isolated from the electrically active regions and may each be connected or connectable via one or more lines (e.g., wires, traces, etc.) to the mapping system and/or sub-system.

Also described herein are apparatus for delivering pulsed electric fields comprising: an elongate body; a first electrode comprising a first wire loop, wherein the first wire loop flexibly extends from the elongate body, the first electrode has a first active region extending along the length of the first wire loop; and a second electrode comprising a second wire loop, wherein the second wire loop flexibly extends from the elongate body, the second electrode has a second active region extending along the length of the second wire loop, wherein the first electrode is either radially offset, laterally offset or both radially and laterally offset from the second electrode. As mentioned above, any of these apparatuses may include a plurality of mapping and/or electrodes on the first electrode outside of the first active region and/or on the second electrode outside the second active region.

Also described herein are methods for delivering a pulsed electric field to a wall of an anatomical structure within a subject's body using an applicator, the method comprising: positioning a first electrode of the applicator comprising a first one or more loops and a second electrode of the applicator comprising a second one or more loops within the subject's body, so that a first active region of the first one or more loops forms a first contact loop in electrical communication with a first region of the wall of the anatomical structure, and so that the second active region of the second one or more loops forms a second contact loop in electrical communication with a second region of the wall of the anatomical structure, the second contact loop is radially and/or longitudinally separated from the first region of the wall of the anatomical structure; and applying a pulsed electrical treatment between the first active region and the second active region. Any of these methods may include mapping a location of the applicator relative to the wall of the anatomical structure using one or more mapping sensors on the applicator. Any of these methods may include sensing one or more electrical properties of the wall of the anatomical structure using one or more sensors on the applicator prior to applying the pulsed electrical treatment and/or in between the application of pulses of the pulsed electrical treatment, and/or after applying the pulsed electrical treatment.

Any of these methods may be methods of treating cardiac tissue, including ablating cardiac tissue. For example, described herein are methods for delivering a pulsed electric field to a wall of a heart within a subject's body using an applicator, the method comprising: positioning a first electrode of the applicator comprising a first one or more loops and a second electrode of the applicator comprising a second one or more loops within the subject's body, so that a first active region of the first one or more loops forms a first contact loop in electrical communication with a first region of the wall of the heart (e.g., a pulmonary vein antrums, pulmonary vein ostiums, and/or other heart wall muscle/ tissue), and so that the second active region of the second one or more loops forms a second contact loop in electrical communication with a second region of the wall of the heart, the second contact loop is radially and/or longitudinally separated from the first region of the wall of the heart; and applying a pulsed electrical treatment between the first active region and the second active region. Any of these methods may include mapping a location of the applicator relative to the wall of the heart using one or more mapping sensors on the applicator. In some examples the method may include sensing one or more electrical properties of the wall of the heart using one or more sensors on the applicator prior to applying the pulsed electrical treatment and/or in between the application of pulses of the pulsed electrical treatment, and/or after applying the pulsed electrical treatment. In any of these methods, the method may include mapping the tissue (e.g., the heart) using, e.g., 3D electro-anatomical mapping; in some examples the method may include mapping or otherwise locating the applicator on the map of the tissue.

Also described herein are apparatuses comprising: an elongate body extending proximally to distally; an applicator region at a distal end region of the elongate body, the applicator region comprising: a first wire extending distally from the elongate body, the first wire having a first active region that is adjacent to a first insulated region of the first wire, and a second wire extending distally from the elongate body, the second wire having a second active region adjacent to a second insulated region of the second wire; wherein the first active region is separated from the second active region by a minimum distance, d, that is substantially constant along the length of the first active region, and further wherein the first active region is configured to have a first polarity and the second active region is configured to have a second polarity.

An apparatus may include: an elongate body extending proximally to distally; and an applicator region at a distal end region of the elongate body, the applicator region comprising: an expandable member configured to radially expand relative to the elongate body; a first wire on the expandable member, the first wire having a first active region that is adjacent to a first insulated region of the first wire; and a second wire on the expandable member, the second wire having a second active region adjacent to a second insulated region of the second wire, wherein the first active region is separated from the second active region by a minimum distance, d, that is substantially constant along the length of the first active region, wherein the first wire and the second wire have a thickness that is 0.38 mm or less, and further wherein the first active region is configured to have a first polarity and the second active region is configured to have a second polarity.

Further, for example, described herein are apparatuses for delivering pulsed electric fields. These apparatuses may include: an elongate body; an expandable member (e.g., balloon), which may be at a distal end region of the elongate body; a first electrode assembly comprising a first plurality of wire loops, each wire loop of the first plurality of wire loops forms a petal having a first active region, wherein the first active regions of each of the first plurality of wire loops are arranged around the expandable member and extend around all or at least a portion of a circumference of the expandable member; and a second electrode assembly comprising a second plurality of wire loops, each wire loop of the second plurality of wire loops forms a petal having a second active region, wherein the second active regions of each of the second plurality of wire loops are arranged around the expandable member and extend around all or at least a portion of a circumference of the expandable member, wherein the first electrode assembly is laterally offset from the second electrode assembly along a length of the expandable member, and wherein the first electrode assembly and the second electrode assembly are configured to expand radially outward when the expandable member is expanded.

For example, an apparatus for delivering pulsed electric fields may include: an elongate body; a balloon on the elongate body; a first electrode assembly comprising a first plurality of wire loops, each wire loop of the first plurality of wire loops forms a petal having a first active region arranged on the balloon; and a second electrode assembly comprising a second plurality of wire loops, each wire loop of the second plurality of wire loops forms a petal having a second active region arranged on the balloon, wherein each of the first active regions and each of the second active regions comprises a flexible bend, an angle of the flexible bend is configured to expand as the balloon is expanded so that the first electrode assembly and the second electrode assembly expands radially outward when the balloon is expanded, further wherein the first electrode assembly is laterally offset from the second electrode assembly along a length of the balloon. In some examples, the first electrode assembly and the second electrode assembly may be shape-set to return to a radially collapsed or constricted configuration when the balloon is contracted.

In any of these apparatuses, the expandable member may comprise an expandable balloon. The first electrode assembly and the second electrode assembly may extend from the elongate body over the expandable member.

The first plurality of wire loops may comprise any number of loops (e.g., between 2 and 10 loops, between 2 and 8 loops, between 2 and 5 loops, between 2 and 4 loops, etc.) and the second plurality of wire loops may comprise any number of loops (which may be equal to the number of loops in the first plurality of loops, e.g., between 2 and 10 loops, between 2 and 8 loops, between 2 and 5 loops, between 2-4 loops, etc.).

Each of the first active regions and each of the second active regions may comprise one or more flexible bend; in some examples the angle of the flexible bend may be configured to expand as the balloon is expanded.

Each wire loop of the first plurality of wire loops and each wire loop of the second plurality of wire loops may each be coupled to an outer surface of the expandable balloon at one or more spots. For example, each wire loop of the first plurality of wire loops and each wire loop of the second plurality of wire loops may each be slidably coupled to an outer surface of the expandable balloon. In some examples each of the first active regions and each of the second active regions may be bounded on either side by insulated regions. In some examples the first and second electrode assemblies are not attached to the expandable member (e.g., balloon) but may reside adjacent to the expandable member. In any of these examples the first and second electrode assemblies may be shape set into a radially collapsed or constricted configuration so that expanding the expandable member (e.g., balloon) radially expands the electrode assemblies and contraction of the expandable member allows the first and second electrode assemblies to return to the radially collapsed (or constricted) configuration.

The first active region of each wire loop of the first plurality of wire loops may be spaced apart from the second active region of a wire loop of the second plurality of wire loops by a fixed distance. The first electrode assembly and the second electrode assembly may be configured to flexibly conform to a wall of an anatomical structure.

As mentioned above, in any of these apparatuses, the first electrode assembly and the second electrode assembly may each be formed of a wire having a diameter, for example, of less than 0.2 mm. The first electrode assembly may be configured to have a first polarity and the second electrode assembly may be configured to have a second polarity.

Further described herein are apparatuses for delivering pulsed electric fields that may include: an elongate body; a plurality of arms configured to extend from the elongate body at an angle (e.g., in a deployed state); a first plurality of electrode lengths extending between the plurality of arms and forming a first treatment electrode; a second plurality of electrode lengths extending between the plurality of arms and forming a second treatment electrode that is radially outward of the first treatment electrode (e.g., in a deployed state); and one or more mapping and/or sensing electrodes on the plurality of arms. In should be understood that in some examples the apparatus is configured to convert from an undeployed state (e.g., unexpanded configuration) to a deployed state (e.g., expanded or treatment configuration), while in other examples the apparatus is configured to already be in the deployed state (e.g., treatment configuration) and does not convert into an undeployed state. The mapping and/or sensing electrodes may be positioned radially outwardly of the first treatment electrode; in some examples, at least some of the mapping and/or sensing electrodes are positioned radially outwardly from the second treatment electrode. The structure including the plurality of arms, the treatment electrodes and the mapping and/or sensing electrodes may be referred to herein as an applicator of the apparatus.

Any of these apparatuses may include an extension region on the arm(s). The extension region may extend radially outward of all of the treatment electrodes when apparatus is in a deployed state. In some examples the arms of the plurality of arms may be insulated hollow members within or through which at least a portion of the first electrode and the second electrode and/or electrical connectors (e.g., wires) may extend. This configuration may permit the collapse and expansion of the applicator while ensuring that, in the expanded or deployed state, the treatment electrodes maintain a consistent shape and spacing, which may be particularly helpful for providing consistent and complete treatment.

The apparatuses described herein may include a deployed state in which the arms extend from the elongate body at an angle, and a retracted (undeployed) configuration in which all or some of the arms are retracted into the elongate body and may collapse or bend so that they are at least partially within the elongate body; the electrode lengths forming the first and second (or more) treatment electrodes may be collapsed in the undeployed state and may be at least partially within the elongate body. In some examples the treatment electrodes may be formed of lengths of wire or other conductor that slide relative to the arms to allow relatively easy transition between the deployed and undeployed state. In some examples the apparatus may be configured so that the applicator is always deployed and does not convert into an undeployed state.

For example, described herein are apparatuses for delivering pulsed electric fields that may include: an elongate body; a plurality of arms extending from the elongate body at an angle; a first plurality of electrode lengths extending between the plurality of arms and forming a first treatment electrode; a second plurality of electrode lengths extending between the plurality of arms and forming a second treatment electrode that is radially outward of the first treatment electrode; and one or more (e.g., a plurality of) mapping and/or sensing electrodes on the plurality of arms.

In some examples an apparatus for delivering pulsed electric fields may include: an elongate body; a plurality of arms configured to extend from the elongate body at an angle when the apparatus is in a deployed state; a first plurality of electrode lengths extending between the plurality of arms and forming a first treatment electrode; a second plurality of electrode lengths extending between the plurality of arms and forming a second treatment electrode that is radially outward of the first treatment electrode in the deployed state; and a plurality of mapping electrodes on an extension region of each arm of the plurality of arms that is radially outward from the second treatment electrode in the deployed state and on an intermediate region of each arm of the plurality of arms that is between the first treatment electrode and the second treatment electrode.

Thus, the plurality of mapping electrodes may include mapping electrodes on an extension region of each arm of the plurality of arms that is radially outward from all of the treatment electrodes in the deployed state. The arms of the plurality of arms may be configured to extend from the elongate body at an angle, e.g., of between about 20 and about 90 degrees relative to the elongate body. For example, the arms of the plurality of arms may be configured to transition from a longitudinally-extending configuration at least partially within the elongate body in the un-deployed state, into an extended configuration wherein each arm of the plurality of arms extends at an angle from the elongate body when extended distally from the elongate body in the deployed state.

Any of these apparatuses may include a spacer at a distal end region of the elongate body configured to maintain a spacing of each arm of the plurality of arms within the distal end region of the elongate body. The spacer may be axially moveable relative to the distal end region of the elongate body. The elongate body may be configured as a sheath, as described above.

The first plurality of electrode lengths may comprise a first plurality of arcs extending between the plurality of arms; further, the second plurality of electrode lengths may comprise a second plurality of arcs extending between the plurality of arms. The first plurality of electrode lengths may comprise a first ring or loop forming the first treatment electrode and the second plurality of electrode lengths may comprise a second ring or loop forming the second treatment electrode.

Any of these apparatuses may include a central electrode that may be configured as a treatment electrode, a mapping and/or sensing electrode, or both. The central electrode may be integrated with the spacer, or it may be separate from the spacer. In some examples the apparatus includes a central electrode without a spacer, or a spacer without a central electrode. The central electrode may be configured to extend distally from a distal end of the elongate body.

Any of the apparatuses described herein may include one or more electromagnetic (EM) sensors coupled to one or more arms of the plurality of arms, including coupled to or positioned on the extension region of one or more arms of the plurality of arms. For example, the apparatus may include an EM sensor within the extension region of one or more arms of the plurality of arms.

An apparatus as described herein may include a third (or more, e.g., fourth, fifth, etc.) plurality of electrode lengths extending between the plurality of arms and forming a third treatment electrode that is radially outward of the first treatment electrode and the second treatment electrode (e.g., when the apparatus is deployed). The mapping/sensing electrode(s) may comprise cylindrical electrodes. In some examples, the mapping/sensing electrodes may be on an outer surface of the arms of the plurality of arms. The first plurality of electrode lengths and the second plurality of electrode lengths may each be formed of a wire having a diameter of 0.2 mm or less.

In some examples the apparatus may be configured to apply energy between the first and second treatment electrodes. For example, the first treatment electrode may comprise an anode and the second treatment electrode may comprise a cathode, wherein the apparatus is configured to deliver a pulsed energy between the first treatment electrode and the second treatment electrode.

The first treatment electrode and the second treatment electrode may each be 5 cm or longer.

Also described herein are apparatuses in which the first treatment electrode may form a circumferential loop that is longitudinally spaced apart from the second treatment electrode. The first and second treatment electrodes may be approximately the same radius. In some examples the first and second treatment electrodes may have different radiuses.

For example, an apparatus for delivering pulsed electric fields may include: an elongate body; a first plurality of arms configured to extend from the elongate body at an angle (e.g., when in a deployed state); a second plurality of arms configured to extend from the elongate body at an angle (e.g., in the deployed state); a first plurality of electrode lengths extending between the first plurality of arms and forming a first treatment electrode; a second plurality of electrode lengths extending between the second plurality of arms and forming a second treatment electrode that is axially separated from the first treatment electrode; and a plurality of mapping and/or sensing electrodes.

In any of these examples the spacing between the first and second treatment electrodes may be maintained (even when using expandable/collapsible configurations) by a plurality of struts extending between the first and second treatment electrodes. For example, an apparatus for delivering pulsed electric fields may include: an elongate body; a first plurality of arms configured to extend from the elongate body at an angle; a second plurality of arms configured to extend from the elongate body at an angle; a first plurality of electrode lengths extending between the first plurality of arms and forming a first treatment electrode; a second plurality of electrode lengths extending between the second plurality of arms and forming a second treatment electrode that is axially separated from the first treatment electrode by a plurality of struts; wherein the plurality of struts extends between the first treatment electrode and the second treatment electrode substantially parallel to a distal end region of the elongate body; and a plurality of mapping and/or sensing electrodes on the struts of the plurality of struts.

For example, each strut may include one or more mapping/sensing electrode. Alternatively, only a subset of the struts may include a mapping/sensing electrode. In some examples the plurality of mapping/sensing electrodes are on the first plurality of arms. The struts of the plurality of struts may extend from at least one of the first plurality of arms and the second plurality of arms. In some examples the first plurality of arms is rotationally offset from the second plurality of arms.

As mentioned above, the arms of the first plurality of arms and the second plurality of arms may be configured to extend from the elongate body at an angle of between 20 and 90 degrees relative to the elongate body. In some examples the arms of the first and second plurality of arms are configured to transition from a longitudinally-extending configuration at least partially within the elongate body into an extended or deployed state wherein each arm of the first and second plurality of arms extends at an angle from the elongate body when extended distally from the elongate body.

Also as described above, any of these apparatuses may include a spacer or a guide at a distal end region of the elongate body to maintain a spacing of each arm of the first and second plurality of arms within the distal end region of the elongate body.

The first plurality of electrode lengths may comprise a first plurality of arcs extending between the first plurality of arms; further wherein the second plurality of electrode lengths may comprise a second plurality of arcs extending between the second plurality of arms. The first plurality of electrode lengths may comprise a first loop or ring forming the first treatment electrode and the second plurality of electrode lengths comprises a second loop or ring forming the second treatment electrode.

Any of these apparatuses may include a central electrode. The central electrode may be configured to extend distally from a distal end of the elongate body. The central electrode may comprise a mapping or/and sensing electrode.

In some examples the first plurality of electrode lengths and the second plurality of electrode lengths are each formed of a wire having a diameter of 0.2 mm or less. The first treatment electrode may comprise an anode and the second treatment electrode may comprise a cathode, wherein the apparatus is configured to deliver a pulsed energy between the first treatment electrode and the second treatment electrode.

All of the methods and apparatuses described herein, in any combination, including a combination of various features disclosed in reference to various examples, are herein contemplated and can be used to achieve the benefits as described herein.

BRIEF DESCRIPTION OF THE DRAWINGS

A better understanding of the features and advantages of the methods and apparatuses described herein will be obtained by reference to the following detailed description that sets forth illustrative embodiments, and the accompanying drawings of which:

FIG. 2 illustrates an example of an applicator configured to deliver an electric treatment, such as nanosecond pulsed energy treatment within a body vessel.

FIG. 3A shows an example of an applicator configured to deliver energy treatment within a body vessel either circumferentially or point-by-point.

FIG. 3B shows an example of an applicator configured to deliver energy treatment within a body vessel and configured for "front facing" and "side facing" energy application.

FIG. 7 shows another applicator similar to one shown in FIG. 4A configured to deliver nanosecond pulsed energy treatment within a body vessel.

FIGS. 8A and 8B show another applicator configured to deliver nanosecond pulsed energy treatment to a body vessel.

FIG. 14 shows another applicator configured to deliver nanosecond pulsed energy treatment to a body vessel.

FIG. 15 shows another applicator configured to deliver nanosecond pulsed energy treatment to a body vessel.

FIG. 16 shows another applicator configured to deliver nanosecond pulsed energy treatment to a body vessel.

FIGS. 23A-23F illustrate an example of an apparatus for delivering pulsed electrical energy within a lumen.

FIG. 25 is an example of an apparatus for delivering pulsed electrical energy within a lumen.

FIG. 26 shows an apparatus for delivering pulsed electrical energy within a lumen.

FIG. 27 illustrates the apparatus of FIG. 26 applying energy around a pulmonary vein.

FIG. 31 shows an apparatus for delivering pulsed electrical energy within a lumen including a balloon to expand the applicator region.

FIG. 32 shows an apparatus for delivering pulsed electrical energy within a lumen.

FIG. 33 shows another view of the apparatus of FIG. 32.

FIGS. 34A-34C show examples of paddle-shaped apparatuses for delivering pulsed electrical energy within a lumen.

FIG. 35 is an example of an apparatus for delivering pulsed electrical energy within a lumen.

FIGS. 36A-36E illustrate further examples of apparatuses for delivering pulsed electrical energy within a lumen.

FIG. 43A shows a distal end view and FIG. 43B shows a side perspective view.

FIGS. 45A and 45B show an example of one wire loop with an active region forming a portion of an electrode assembly as described herein, illustrating expansion of the active region of the wire loop at a flexible bend.

FIG. 45C shows an example of a portion of an apparatus including small-diameter wire electrode assemblies formed from a plurality of wire loops with active regions having flexible bends arranged on an expandable member (e.g., balloon).

FIG. 46A shows an example with a transparent expandable member (e.g., balloon). FIG. 46B shows an example with an opaque expandable member. FIG. 46C is an enlarged view of an example of the active regions of some of the wire loops of the electrode assemblies of FIG. 46B.

FIG. 47A illustrates an example of an apparatus including a first and a second treatment electrodes, and a plurality of mapping and/or sensing electrodes on an extension region of the arms supporting the first and second treatment electrodes. FIG. 47B shows the apparatus for delivering pulsed electric fields also including a central electrode. FIG. 47C shows an example of the apparatus including various features of FIGS. 47A-47B with one of the arms shown as transparent.

FIG. 50 shows an example of animal model tissue showing ablation of discrete regions of the tissue using an apparatus similar to that shown in FIGS. 47A-47C.

DETAILED DESCRIPTION

Figure 1:
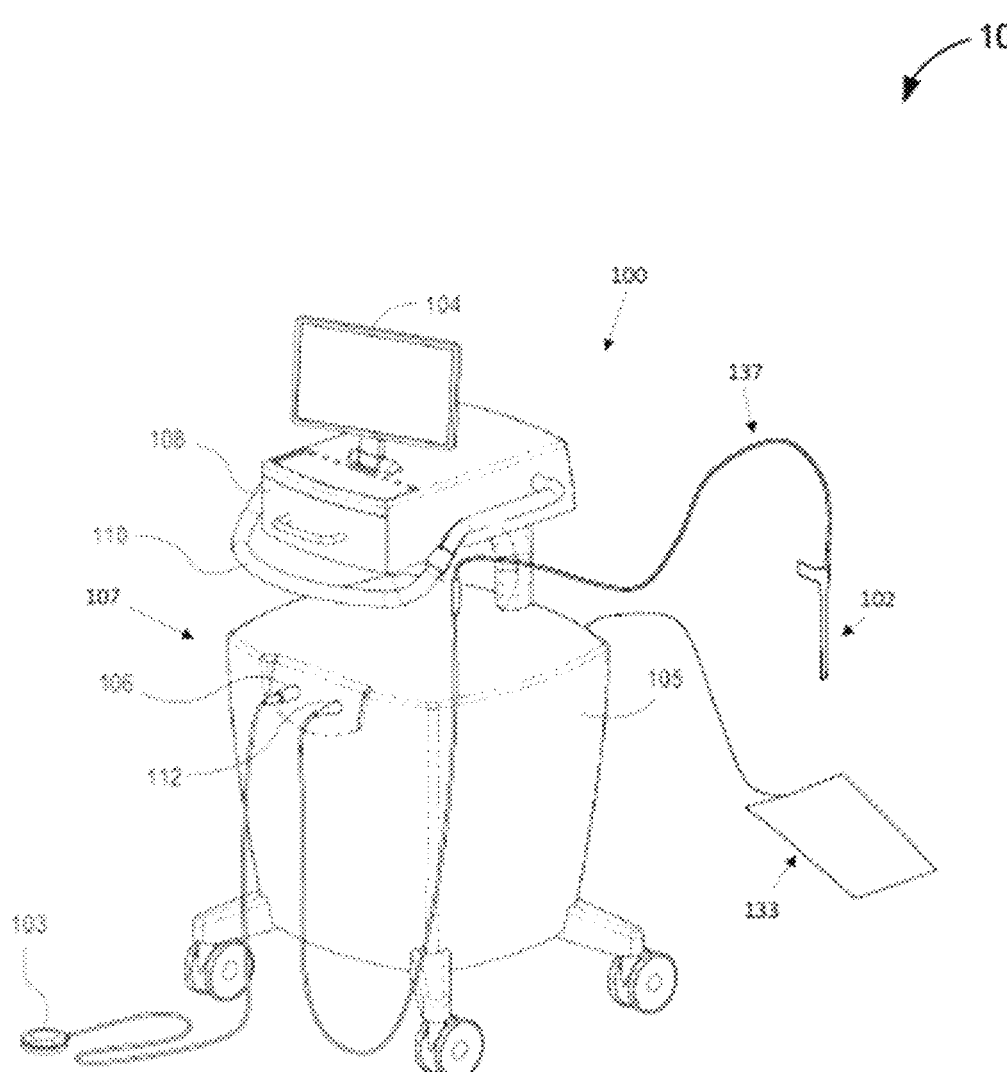
FIG. 1 illustrates one example of a system for delivering high voltage, fast pulses of electrical energy.

Described herein are systems and methods for treating a body, including a body lumen such as a body vessel, with pulsed electrical fields using electrodes adapted to be inserted into the body vessel such as, for example, arteries, veins, antrum, and any other vessels within a body as stated above. In general, the apparatuses and methods described herein may be positioned inside of any body chamber, including, but not limited to, a lumen of a body such as a tubular body member or vessel, against any wall of an organ, and/or in transitional areas (e.g., antrum, ostia, etc.).

In some cases, the body vessel may have an irregular or varying shape. For example, the antrum of a pulmonary vein may transition from a relatively large area or diameter to a relatively small area or diameter. These body vessel surfaces may be difficult for the electrodes to establish an effective contact with which to provide treatment. Described herein are various electrodes that may easily adapt and conform to irregular and/or varying shapes and provide positive contact with the body vessel.

The pulsed electrical treatment may be microsecond pulsed treatment, or sub-microsecond pulsed treatment, including nanosecond pulses. For example, nanosecond pulsed electric fields treatment may refer to the application of relatively high voltages (in some cases 5 kV or greater) for a relatively short amount of time (in some cases between about 1 nanosecond and 999 ns). These high voltages and short duration times create a pulsed electric field in the region where the voltages are applied. In some cases, nanosecond pulsing may induce apoptosis within cellular structures which may reduce a cells' inflammatory response.

Any of the methods described herein may be ablation methods. For example, the methods described herein may be particularly useful for the treatment of cardiac regions, vessels, etc., such as, but not limited to, an antrum. In some examples, these methods and apparatuses may be used for the treatment of atrial fibrillation and other cardiac conditions, including for ablation of cardiac tissue. As will be described in greater detail below, any of these methods and apparatuses may be used for treating body regions, such as the antrum of the pulmonary vein, that has a tapered or narrowing profile. Thus, in some examples the apparatuses and methods described here are adapted for use where the shape of the body lumen in which they are to be used has a diameter that changes abruptly.

Alternatively or additionally, these apparatuses and methods may be used to treat the walls of vessels or other lumen that are not necessarily tapered or are only slightly tapered. In some examples these methods and apparatuses may be used to treat the walls of a vascular or respiratory lumen. For example, these methods and apparatuses may be used to treat arterial stenosis, including in combination with a stent or angioplasty procedure. Thus, in some cases, these methods may be performed within the first 2-4 days following angioplasty and/or stenting. Untreated, smooth muscle cells (SMCs) at the luminal surface in deendothelialized areas may continue to proliferate at a low rate. The methods and apparatuses described herein may prevent or reduce this.

FIG. 1 illustrates one example of a system 100 (also referred to herein by way of example as a sub-microsecond generation system) for delivering fast pulses of electrical energy. Such system may include an elongate applicator tool 102, a pulse generator 107, footswitch 103, and user interface 104. Footswitch 103 is connected to housing 105 (which may enclose the electronic components) through a cable and connector 106. The elongate applicator tool 102 may include electrodes and may be connected to housing 105 and the electronic components therein through a cable 137 and high voltage connector 112. The system 100 may also include a handle 110 and storage drawer 108. The system 100 may also include a holder (e.g., holster, carrier, etc.) (not shown) which may be configured to hold the elongate applicator tool 102. In some examples the system may be configured for monopolar treatment and may optionally include a dispersive electrode 133 (e.g., a return electrode pad).

The applicator tool may be any of the apparatuses for delivery pulsed electrical fields within a body vessel, as described in detail herein. These apparatuses may generally include an elongate, flexible body (generically referred to herein as an elongate body, a catheter or elongate catheter body) at the end of which are one or more electrodes, including electrodes forming one or more loops, that may apply pulsed electrical fields to the body. In some cases, the elongate applicator tool 102 includes one or more imaging sensors, such as one or more cameras and/or fiber optics at or near the distal end of the elongate applicator tool 102. The camera(s) (not shown for simplicity) may be forward-facing and/or side facing. The system 100 may be configured to display images (in real time, and/or recorded) taken by the elongate applicator tool 102, in order to identify the target treatment area(s) and/or region(s).

A human operator may select a number of pulses, amplitude, pulse duration, and frequency information, for example by inputting such parameters into a numeric keypad or a touch screen of user interface 104. In some examples, the pulse width can be varied. A microcontroller may send signals to pulse control elements within the system 100. In some examples, fiber optic cables are used which allow control signaling while also electrically isolating the contents of the metal cabinet (e.g., the housing 105) with a sub-microsecond pulse generation system 100, e.g., the high voltage circuit, from the outside. In order to further electrically isolate the system, system 100 may be battery powered instead of being powered from a wall outlet.

The elongate applicator tool 102 may be hand-held (e.g., by a user) or it can be affixed to a movable arm of a robotic system, and its operation may be at least partially automated or fully automated, including computer-controlled operation.

FIG. 2 illustrates an example of an applicator 200 configured to deliver a treatment, such as a nanosecond pulsed energy treatment within a body vessel. The body vessel may be any feasible vessel including, but not limited to, an antrum of the pulmonary vein or the pulmonary veins themselves. In this example, the applicator 200 may include a proximal ring 210, a distal ring 220, and an elongate catheter body 230. Although the applicator 200 is shown with two rings 210 and 220, in other examples, the applicator 200 may include any feasible number of rings. The term "distal" may generally refer to a portion closest to the distal end of the applicator (and closest to a treatment tissue/surface), and the term "proximal" may generally refer to a portion that is relatively further from the distal end of the applicator and the treatment tissue/surface. However, persons skilled in the art will recognize that other terms may be used to identify and distinguish features (including the proximal and distal rings 210 and 220) of the applicator 200.

For example, the proximal and distal rings 210 and 220 may be referred to a first and second rings.

The proximal and distal rings 210 and 220 may be formed from any conformable material. In at least one example, the proximal and distal rings 210 and 220 may be formed from Nitinol (e.g., nickel titanium) however any other feasible material may be used, such as stainless steel. As shown in the example applicator 200, the proximal ring 210 may have a larger diameter than the distal ring 220. In other examples, the proximal ring 210 may have a smaller diameter than the distal ring 220.

The proximal and distal rings 210 and 220 may be used as circularly shaped electrodes to deliver, for example, nanosecond pulsed energy to selected treatment areas. In this example, the entire outer perimeter of each of the rings 220, 210 may be active regions (e.g., electrically contiguous) so that the outer perimeter of the rings, but not the inner arms 211, 221 (which may be insulated) form the active regions for applying electrical energy. In some examples, the proximal ring 210 and the distal ring 220 may be retracted into the catheter body 230. The applicator 200 may then be positioned in the treatment area. After placement of the applicator 200 is confirmed, then the proximal ring 210 and the distal ring 220 may be deployed from the catheter 230.

In some examples, the ring electrodes 210 and 220 are not deployed from within the catheter body 230 but may be housed together with the catheter body 230 within a delivery catheter; the distal end of the apparatus (e.g., the ring electrodes in this example) may be deployed out of the delivery catheter once at or near the target treatment location in the body. For example, the entire apparatus (including the catheter body and the electrodes) may be inserted into the proximal end of the delivery catheter (also referred to herein as a guiding sheath). The guiding sheath may already be in the patient, so that the distal end of the sheath is positioned near the target region (e.g., at or near the left atrium in some examples). The elongate catheter body and the electrodes (e.g., ring electrodes) may be inserted into the proximal valve of a guiding sheath using an introducer (e.g., a plastic tube) and the apparatus may slide distally within the sheath. In some examples the delivery catheter holding the distal end (e.g., the ring electrodes) may be advanced to the target tissue and then held in position while the distal end is driven out of the delivery catheter.

The proximal ring 210 may include two lobes. That is, the proximal ring 210 may be divided into two semi-circular sections that are joined to arms 211. In some examples, the arms 211 may be insulated. Similarly, the distal ring 220 may include two lobes that are joined to arms 221. In other examples, the proximal and distal rings 210 and 220 may include any number of lobes and arms. In some cases, increasing the number of lobes may increase flexibility of the proximal and distal rings 210 and 220 enabling them to conform to different shapes of body vessels more easily, allowing the electrodes of the rings to be in good apposition with the target tissue. In some examples, the arms 211 and 221 may be formed of Nitinol or any other feasible material. The arms 211 and 221 may flexibly couple the proximal ring 210 and the distal ring 220 to the elongate catheter body 230. Note that in any of the apparatuses described herein the entire apparatus may be referred to as a "catheter" and the elongate, typically flexible body portion extending from the distal end may be referred to as the catheter body (e.g., catheter body 230). The electrodes extending from the distal end of the elongate catheter body may be movable relative to the distal end of the elongate catheter body or they may be fixed relative to the distal end.

FIG. 2 shows a distance 240 that separates the proximal ring 210 and the distal ring 220. For example, the distance 240 may describe the distance between a plane that generally includes the proximal ring 210 and a plane that generally includes the distal ring 220. The distance 240 may be predetermined or may be variable and determined by a user when the proximal ring 210 and the distal ring 220 are deployed. In some examples, a voltage potential between the proximal ring 210 and the distal ring 220 and the distance 240 may determine an electric field density that may be delivered by the applicator 200. For example, a relatively small distance 240 may provide a higher electric field density compared to a relatively larger distance 240.

In some examples, the applicator 200 may be guided to the identified treatment area by the elongate catheter body 230 and a proximal handle (such as the handle portion of the elongate applicator tool 102 shown in FIG. 1). In some examples, the applicator 200 may also be guided by guide wires (not shown for simplicity) and/or the use of fluoroscopy equipment. The apparatuses described herein (e.g., applicator 200) may include a central lumen (e.g., through the elongate catheter body) which may allow the operation of the apparatus over a guidewire. Alternatively, a rapid exchange lumen may be present on a side of the applicator distal end.

The distal end of the apparatus may be positioned in the approximate region of the tissue to be treated (the target tissue region), and the ring electrodes (e.g., the proximal and distal rings 210 and 220) may be expanded out, as shown in FIG. 3A. The proximal and distal rings 210 and 220 may be flexibly coupled to and emerge from the elongate catheter body 230 and be brought into apposition with the body vessel. The precise position of the applicator 200, including the ring electrodes, may be verified, and/or the apparatus may be repositioned before applying energy.

Nanosecond pulsed energy treatment of the body vessel may then begin. In some examples, the system 100 and the applicator 200 may be configured for bipolar operation, e.g., between the proximal and distal rings 210 and 220. In some examples the proximal ring 210 may be referred to as a cathode and the distal ring 220 may be referred to as an anode (or vice versa). In other examples, the proximal ring 210 may be associated with a signal having a negative signal and the distal ring 220 may be associated with a signal having a positive signal. The proximal and distal rings 210 and 220 may perform as electrodes to deliver the nanosecond pulsed energy. Electrodes carrying opposing polarity signals may enable electric fields associated with pulsed treatment to be produced between the electrodes. In some examples, the system 100 (including the applicator 200) may be configured for monopolar operation. For example, the proximal and distal rings 210 and 220 may be electrically coupled to each other and a signal may be applied between them and a return electrode (e.g., another conductor such as a portion of the elongate catheter body 230, or a conductive pad or electrode) that may be in contact with the patient.

After the delivery of the nanosecond pulsed energy treatment, the applicator 200 may be moved to another area of the body vessel or removed from the patient.

Any of the apparatuses described herein may also be elastically resilient and configured for use in regions of the body that may expand and contract, such as during diastole/systole, respiration, etc. For example, as just described the electrodes may be formed as rings (or partial rings) that may be flexibly coupled to a distal end region of the catheter body. The flexible coupling may be through a wire or other member that may allow the rings to flex with movement of the tissue, while remaining in position on the tissue.

FIG. 3A shows another example of an applicator 300 configured to deliver a treatment, such as nanosecond pulsed energy treatment, within a body vessel. Similar to the applicator 200 of FIG. 2, the applicator 300 may include the proximal ring 210, the distal ring 220, the arms 211 and 221, and the elongate catheter body 230. The applicator 300 may also include a point-by-point ablation tip 310. The point-by-point ablation tip 310 may be disposed distally on the elongate catheter body 230 with respect to the distal ring 220. In some examples, the point-by-point ablation tip 310 may provide targeted treatment independent and separate from the proximal ring 210 and the distal ring 220. Thus, the point-by-point ablation tip 310 may include one or more electrodes to deliver nanosecond pulsed energy (not shown for simplicity). Alternatively, in some examples point-by-point ablation may be achieved by using a subset of the ring or petal electrodes extending outward from the elongate body (elongate catheter body) 230. This is described in more detail in reference to FIGS. 7 and 32-33, below.

FIG. 3B is another example of an apparatus that is configured to apply either circumferential treatment over a large area or point-by-point treatment at a smaller area by using either "front-facing" or "side-facing" approaches as explained below. The apparatus show in FIG. 3B is configured as a 3-pole ablator (apparatus) in which an electrical field can be applied either between a distal ring 314 that may be held at a first polarity (polarity 1) and a center electrode 310 that is held at a second polarity (polarity 2). The distal end or "front" of the device may be "facing" the tissue. Alternatively the energy can be applied between the distal ring 314 (e.g., at polarity 1) and the proximal ring 312, which may be set to polarity 2. The side of the device may face the tissue. Thus, the apparatus (applicator 300') may be used to apply smaller (point) application of energy or a single shot (e.g., circumferential) application of energy to a larger area.

The apparatus shown in FIG. 3B may also use just a portion of either the distal or proximal (or both) rings to apply a smaller region of treatment. For example, in FIG. 3B, the distal ring 314 is formed of three subregions 314', 314" and 314''' that may be electrically coupled together to form a single electrode. Similarly, the proximal ring 312 is also formed of three subregions 312', 312", 312''' that are coupled together to form the single electrode. This apparatus may also be configured to apply energy between just one or two subregions (or a subregion and the single central electrode, or the subregion and the full proximal ring) of the distal ring in order to apply energy over a smaller area. Thus, in some configurations each of the subregions may be individually energized. In some examples adjacent subregions of the same ring may be used at different polarities to apply energy between them.

The applicators in FIGS. 3A and 3B 300, 300' are shown in a deployed mode, e.g., with respect to a body vessel 320. One example of a body vessel 320 may be a pulmonary vein which may include an antrum 325. The antrum 325 may transition in size from a first diameter to a second diameter. Thus, the different diameters of the proximal ring 210 and the distal ring 220 may advantageously enable the applicator 300 to conform to the varying shape of the antrum 325. In some examples, the diameters of the proximal and distal rings are different (e.g., the proximal ring is larger than the distal ring). In some examples, the one (or both) of the proximal and distal rings are configured so that the diameter is adjustable, which may allow the apparatus to confirm to different shapes and diameters.

In any of the apparatuses described herein the first and second rings may be referred to as electrode rings, or simply "electrodes". In some examples the first electrode (e.g., the proximal electrode ring 210) is configured to have one or more loops (two loops are shown in FIG. 2, while FIG. 4A, described below, shows five loops), and includes an electrically active region ("active region") that is formed on the one or more loops. The active region is the electrically conductive region that is configured to contact target tissue and between which the pulsed electrical field is applied. The active region may be exposed (e.g., may include a conductive surface) and uninsulated, as compared to the other region of the loop. All of these conductive regions are electrically connected, e.g., forming a single electrode. The active region is therefore typically long and narrow, e.g., formed from the wire of a portion of the one or more loops.

In the example applicator 300, the arms 211 and 221 are shown offset approximately ninety degrees with respect to each other. In other examples, the arms 211 and 221 may be offset by any feasible amount. The applicator 300 may be used for various cardiac applications, such as treatment of atrial fibrillation, ventricular tachycardia and other cardiac related ablations. However, it is not limited to the cardiac applications and could be used to apply electric energy in other parts of the body.

Figure 4A:
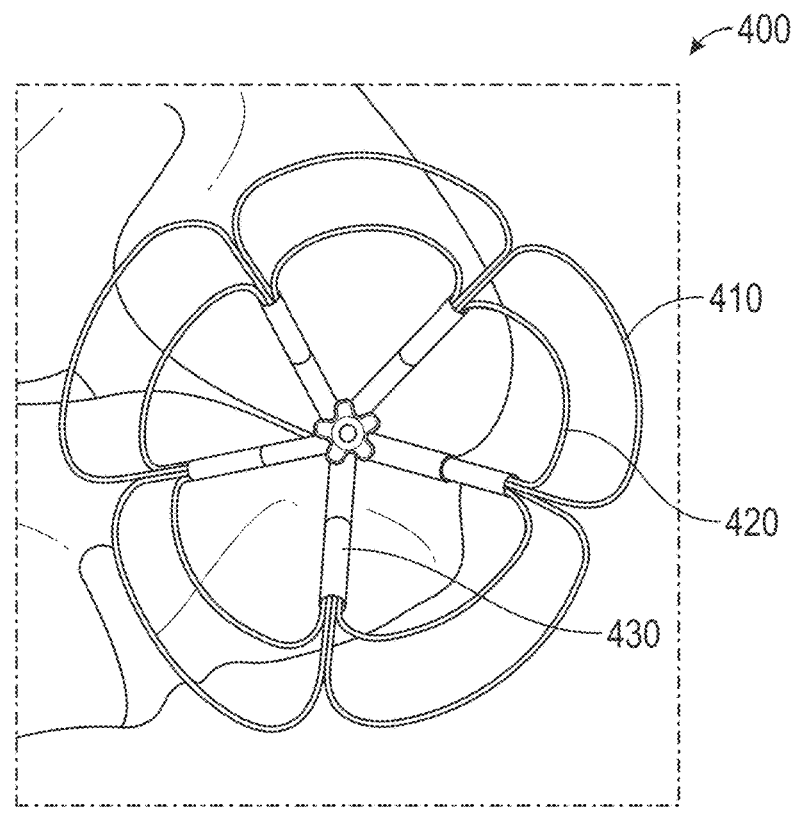
FIGS. 4A and 4B show another example of an applicator configured to deliver nanosecond pulsed energy treatment within a body vessel.
Figure 4B:
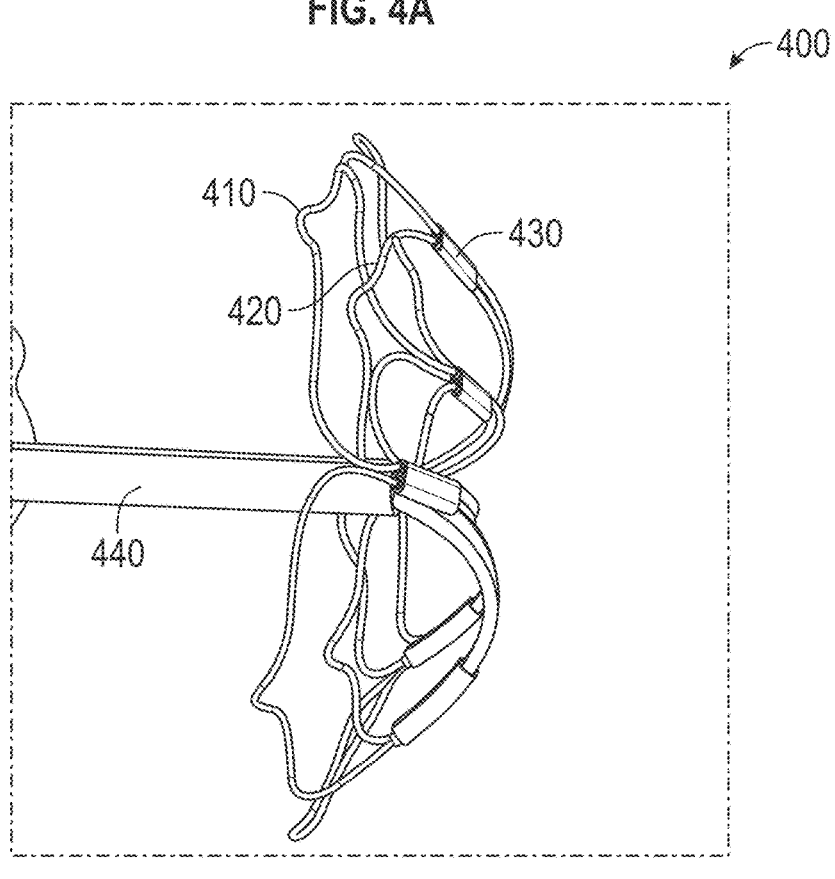

FIG. 4A shows another example of an applicator 400 configured to deliver nanosecond pulsed energy treatment within a body vessel. The applicator 400 may include a proximal ring 410 and a distal ring 420. The proximal and distal rings 410 and 420 may each include 5 lobes. In addition, the applicator 400 may include five arms 430 to flexibly couple the proximal and distal rings 410 and 420 to the elongate catheter body (not shown). As described above, proximal and distal rings 410 and 420 with relatively more lobes may be more flexible than proximal and distal rings with fewer lobes. FIG. 4B shows a side view of the applicator 400. The proximal and distal rings 410 and 420 and the arms 430 are shown coupled to an elongate catheter body 440.

Figure 4C:
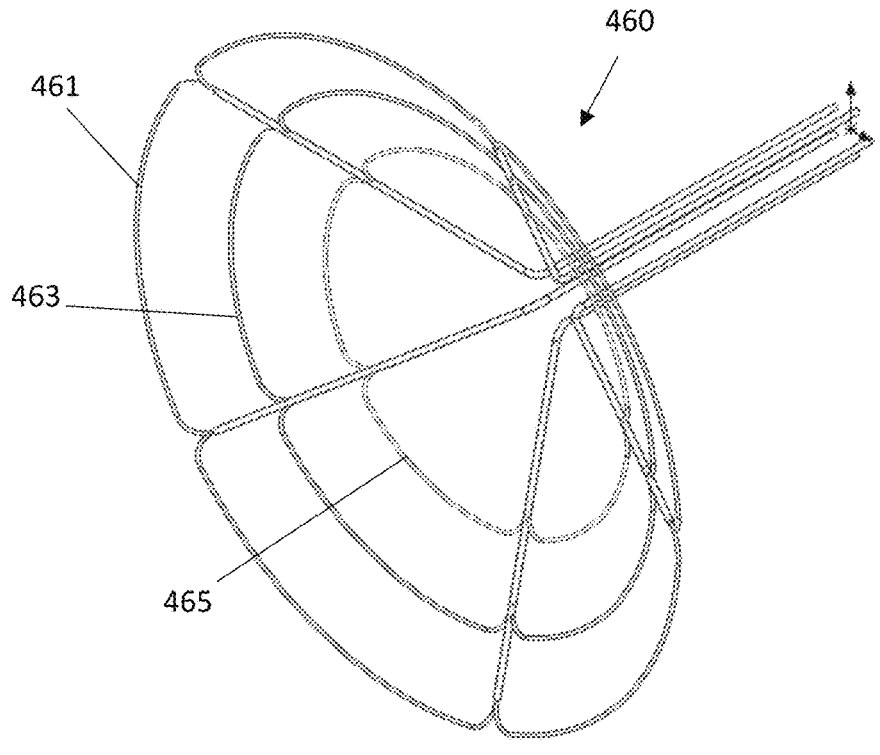
FIG. 4C is another example of an apparatus for delivering energy (e.g., nanosecond pulsed electrical energy) within a body vessel either as a single shot or point-by-point.
Figure 4D:
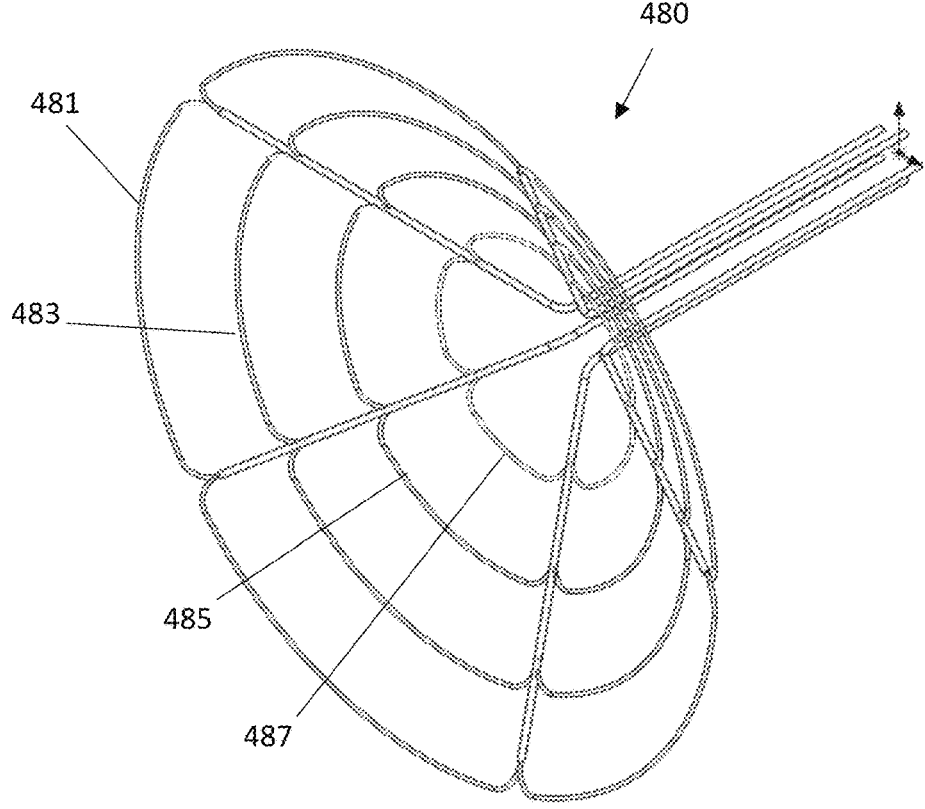
FIG. 4D is another example of an apparatus for delivering energy (e.g., nanosecond pulsed electrical energy) within a body vessel either as a single shot or point-by-point.
Figure 4E:
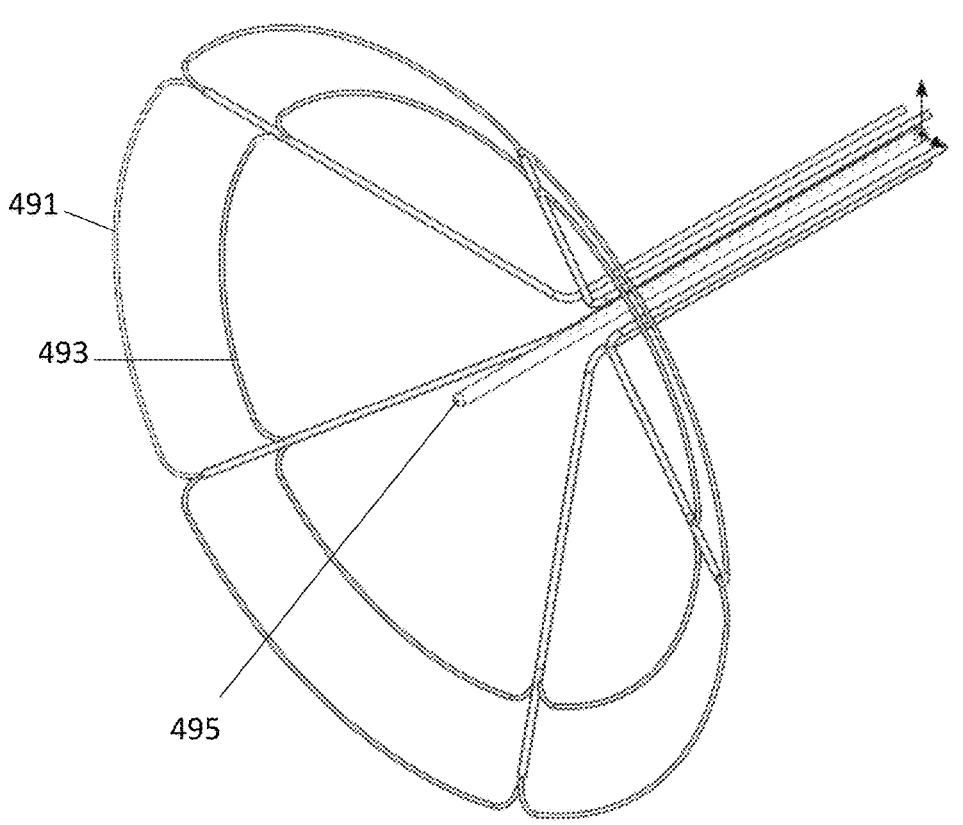
FIG. 4E is another example of an apparatus for delivering energy (e.g., nanosecond pulsed electrical energy) within a body vessel.

FIGS. 4C-4E illustrate examples of applicators that may be used to deliver nanosecond pulsed electrical energy treatment within a body vessel. These examples are similar to those shown in FIGS. 2, 3A-3B and 4A-4B in that they may include multiple rings of electrodes that may be selectively activated to apply bipolar energy for treating tissue. These apparatuses may also be referred to as conformable ring apparatuses, which may be used to apply energy to tissue within the body. In one non-limiting example, the apparatuses shown in FIGS. 4C-4E may be used for bipolar application of electrical energy on myocardial tissue including but not limited to antrum, ostium, and medial/lateral walls (such as treatment of the pulmonary vein).

As described above for FIGS. 4A-4B, in some examples, the apparatuses described herein include two rings of electrodes, an inner ring and outer ring, which may be used for treatment of tissue, including (but not limited to) myocardial tissue in the antrum and/or antrum-ostium. In some examples, additional rings may be used. For example FIG. 4C shows an apparatus including three rings, and FIG. 4D shows an example having four rings. FIG. 4E illustrates an example having two rings with a center electrode. These configurations may allow for adaptability to the patient anatomy as well and may assist in achieving both single shot treatment (e.g., treatment of the whole region such as circumference of the vessel in one treatment, including ablation) and point-by-point treatment (e.g., treatment of small portions of the body vessel one at a time, including ablation).

FIG. 4C shows an example of a configuration of an applicator 460 apparatus having three rings of electrodes, including an outer ring 461 having a diameter of approximately 30 mm. The outer electrode may be formed of a plurality of subregions (e.g., petals or loops) that may be electrically coupled together to apply a first polarity; in some examples individual subregions may be independently activated. FIG. 4C also includes a second ring 463 that is smaller and concentrically arranged relative to the first ring. In FIG. 4C the second ring has a diameter of approximately 23 mm and may also be formed of a plurality of subregions that may be electrically coupled to provide a second polarity. The plurality of subregions may also, in some examples, be separately activated. The same apparatus may also include a third ring 465 that is concentrically arranged relative to the second ring and may similarly be formed of a plurality of subregions that may be electrically coupled to provide the first polarity. In FIG. 4C the third ring has a diameter of approximately 16 mm. The outer and middle rings may be used for treating larger antrums and/or ostiums, while a second configuration may use the second and third rings for applying treatment in smaller antrums and/or ostiums. Varying sizes of the diameters and/or number of rings may allow the system to select which pairs of rings to designate (at which polarities) in order to provide greater adjustment and fit when treating different sized tissue regions, such as (but not limited to) antrums and/or ostiums.

For example, in FIG. 4D the apparatus includes four concentrically arranged rings. The outer electrode (ring 481) may be formed of a plurality of subregions that may be electrically coupled together to apply a first polarity; in some examples individual subregions may be independently activated. A second ring 483 is concentrically arranged relative to the first ring and may also be formed of a plurality of subregions that may be electrically coupled to provide a second polarity or may be independently activated (energized). A third ring 485 of a smaller circumference is concentrically arranged relative to the second ring and may similarly be formed of a plurality of subregions that may be electrically coupled to provide the first polarity. Finally, a fourth electrode (ring 487) of even smaller circumference is concentrically arranged relative to the third ring.

Any of these apparatuses may provide a central small (e.g., point) electrode, as shown in FIG. 4E. FIG. 4E is similar to FIGS. 4A and 4B in having two concentrically arranged rings of electrodes. The first ring electrode 491 may be formed of a plurality of subregions electrodes each formed from a wire having an exposed electrically active region. As in any of these examples, in some configurations each sub-region may be individually controlled and/or they may all be electrically coupled together to form a single electrode. The second ring electrode 493 is concentrically arranged relative to the first ring electrode and may, like the first ring electrode, be formed from a plurality of subregions. Finally, the example shown in FIG. 4E may also include a single central electrode 495 that may be configured to apply a polarity that is opposite of the polarity applied to either the larger outer ring (or a subregion of the outer ring) or to the inner ring (or a subregion of the inner ring).

Any of these apparatuses can be used as a distal part of an elongate body (such as a catheter) and may be used in treatment of, for example, atrial fibrillation. Treatment of atrial fibrillation can include various target sites including but not limited to: Pulmonary Vein (PV) antrums, PV ostiums, and heart wall muscle/tissue. As described herein, these apparatuses may be useful for treating a large area (e.g., a single shot application of sub-microsecond pulsed energy), for example, for treating varying sized Pulmonary Vein antrums/ostiums and/or the ability to provide point-by-point tissue treatment (e.g., ablation) throughout the anatomy of the heart. These apparatuses may also be used to apply sub-microsecond treatments in other parts of the human body. For example, larger diameter outer rings can be used for single shot treatment of antrums and ostiums, while smaller inner rings can be used for point-by-point ablation of targeted tissue. Due to the conformability and adjustability of these configurations, treatment can be achieved more efficiently while also being able to adjust/conform to varying sized anatomies.

Figure 5:
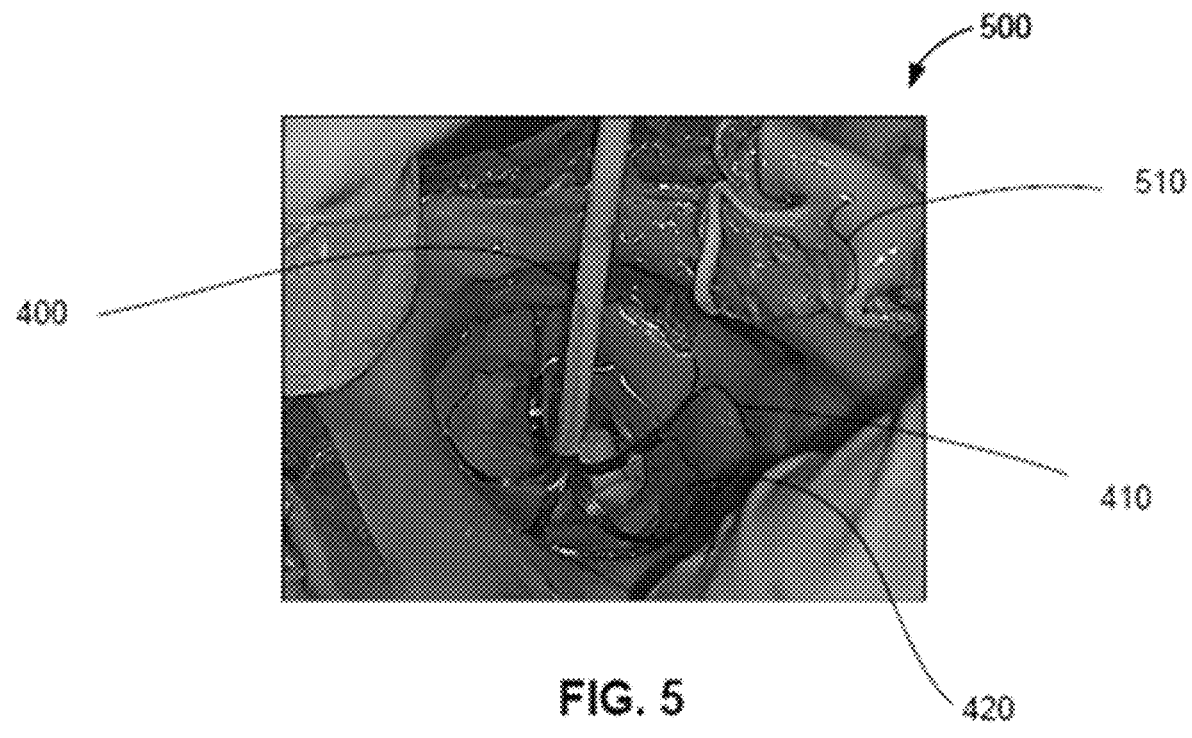
FIG. 5 shows an illustration of the applicator of FIG. 4 disposed within a pulmonary vein.

FIG. 5 shows an illustration 500 of the applicator 400 of FIG. 4 disposed within an antrum 510 of a pulmonary vein. The proximal ring and distal rings 410 and 420 may conform to the surface of the pulmonary vein.

Figure 6A:
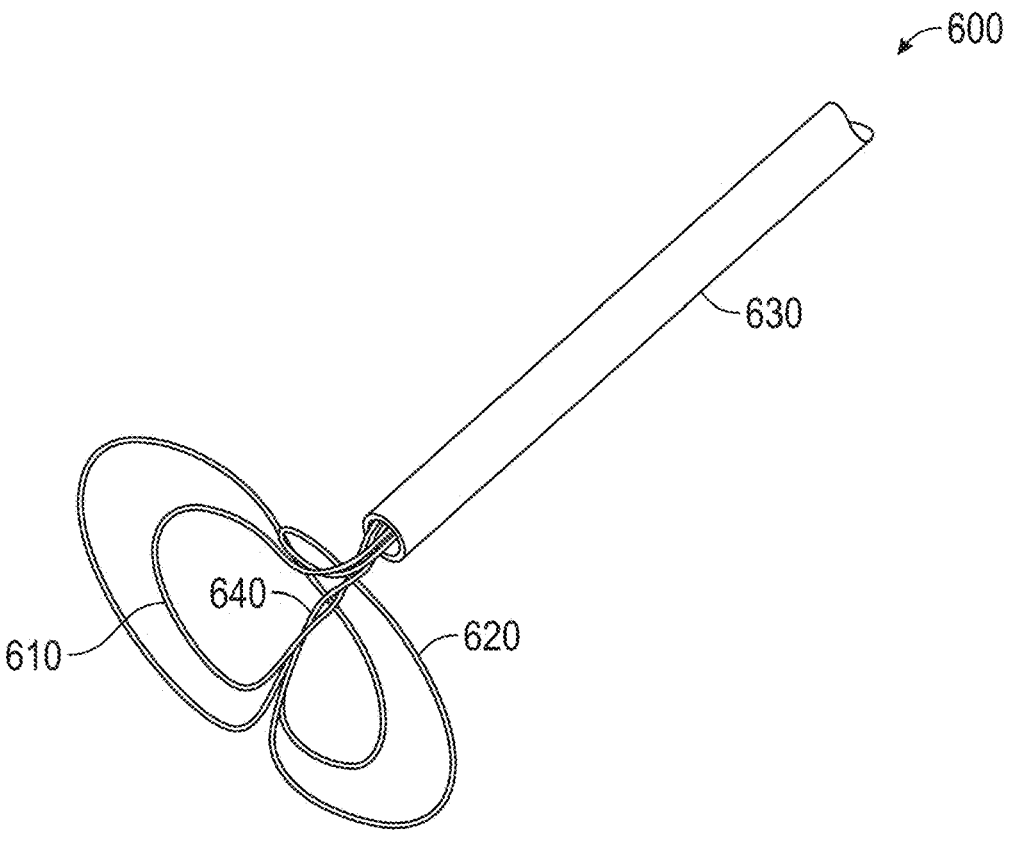
FIG. 6A shows another applicator configured to deliver nanosecond pulsed energy treatment within a body vessel.

FIG. 6A shows another applicator 600 configured to deliver a treatment, such as nanosecond pulsed energy treatment within a body vessel. The applicator 600 may include a first ring 610, a second ring 620, an elongate catheter body 630, and arms 640. The arms 640 may electrically and flexibly couple the first and second rings 610 and 620 to the system 100 (not shown) through the elongate catheter body 630. The first and second rings 610 and 620 and the arms 640 may be formed from Nitinol or any other feasible material. Additionally, the first ring 610 may have a first diameter and the second ring 620 may have a second diameter, different than the first diameter. The different diameters may determine, at least in part, the density of the electric field associated with the nanosecond pulsed energy treatment. Although shown with two lobes, the first and second rings 610 and 620 may include any feasible number of lobes. The first and second rings 610 and 620 may be collapsed and withdrawn into the delivery catheter (not shown), or in some implementations into an elongate catheter body 630 to allow for the placement of the applicator 600 with respect to the treatment area.

In contrast to the applicators 200, 300, and 400, the first ring 610 and the second ring 620 of the applicator 600 may be approximately co-planar. This co-planar arrangement may enable the electrodes (e.g., the first and second rings 610 and 620) to provide better contact with planar tissues and/or tissues shaped similar to an antrum of a pulmonary vein. In some examples, the electrodes may even have a configuration with a "funnel" facing in the direction opposite to the antrum of the pulmonary vein.

The applicator 600 may be configured for bipolar operation. Pulsed energy may be transmitted between the first ring 610 and the second ring 620. Thus, the first ring 610 may be associated with a signal having first polarity (e.g., a positive signal) and the second ring 620 may be associated with a signal having second polarity (e.g., a negative signal). In other examples, the first ring 610 may be associated with a signal having a negative signal and the second ring 620 may be associated with a signal having a positive signal. In another example, the applicator 600 may be configured for monopolar operation. For example, the first and second rings 610 and 620 may both be electrically coupled together and a return electrode (e.g., on the elongate catheter body 630 or a conductive pad) may be used.

Figure 6B:
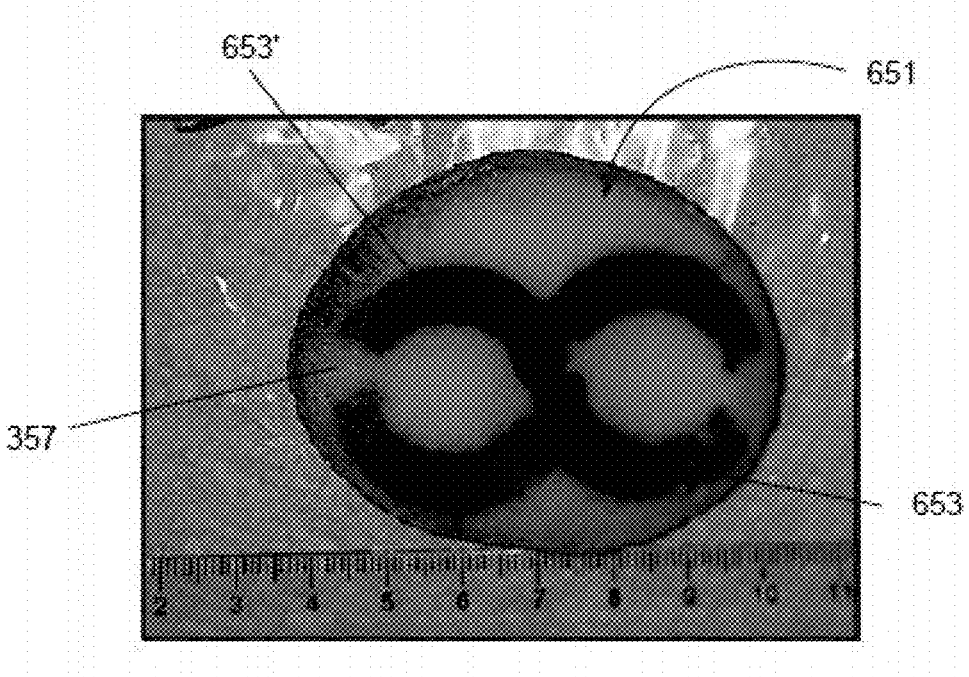
FIG. 6B shows one example of the effects of a treatment with an applicator similar to the applicator of FIG. 6A.

FIG. 6B shows an example illustrating the use of an applicator similar to the one shown in FIG. 6A to treat a model tissue 651. In FIG. 6B, nanosecond pulse treatment was applied to the model tissue (potato submerged in saline)

using an applicator similar to the applicator of FIG. 6A, showing treatment of two regions 653, 653' (e.g., applying the apparatus twice). In particular, the applicator has been used to apply pulsed electrical treatment against two target regions. Two annular regions are formed by the application of the first and second loop electrodes. In this example, darker regions of the test tissue show the effect of the nanosecond pulse electric field on the target tissue model. For each of the two applied treats (shown overlapping in this example), approximately 320 degrees were treated; small gaps where the active regions of the electrodes do not cover are shown 357.

FIG. 7 shows another applicator 700 configured to deliver nanosecond pulsed energy treatment within a body vessel. The applicator 700 may include a first ring 710, a second ring 720, an elongate catheter body 730, and arms 740. The arms 740 may electrically and flexibly couple the first and second rings 710 and 720 to the system 100 (not shown) through the elongate catheter body 730. The first and second rings 710 and 720 and the arms 740 may be formed from Nitinol or any other feasible material. Additionally, the first ring 710 may have a first diameter and the second ring 720 may have a second diameter, different than the first diameter. The different diameters may determine, at least in part, the density of the electric field associated with the nanosecond pulsed energy treatment.

The rings in FIG. 7 may be formed of a plurality of sub-sections ("petals") as shown. For example in FIG. 7 each ring includes five sub-sections. These sub-sections may be configured to act as a single ring, e.g., by applying energy to all of the subsections together, or one or more sub-sections (petals) may be activated separately. For example, in FIG. 7, the outer and inner lower sub-section 733, 734 may be activated without activating the adjacent sub-sections. The use of sub-sections of these rings may allow the device to be used for point-by-point treatment, providing a smaller treatment area, as described herein.

Similar to the applicator 600 of FIG. 6A, the first ring 710 and the second ring 720 may be approximately coplanar. Thus, function and use of the applicator 700 may be similar to the function and use of the applicator 600. The applicator 700 is shown with 5 lobes, although in other examples, other numbers of lobes are possible. As described above, applicators with relatively more lobes may be more flexible than applicators with relatively fewer lobes, and therefore may more easily conform to some body vessels.

The applicator 700 may be configured for bipolar operation. Pulsed energy may be applied between the first ring 710 and the second ring 720. In some examples, the first ring 710 may be configured as an anode and the second ring 720 may be configured as a cathode (or vice versa). In another example, the applicator 700 may be configured for monopolar operation. For example, the first and second rings 710 and 720 may both be coupled together and a return electrode (on another portion of the elongate catheter body 730 or a conductive pad or electrode) may be in contact with the patient.

FIGS. 8A and 8B show another applicator 800 configured to deliver energy, such as nanosecond pulsed energy treatment to a body vessel. The applicator 800 may include a proximal ring 810, a proximal arm 811, a distal ring 820, a distal arm 821, and an elongate catheter body 830. The proximal and distal arms 811 and 821 may electrically and flexibly couple the proximal and distal rings 810 and 820 to the system 100 (not shown) through the elongate catheter body 830. The proximal and distal rings 810 and 820 and the proximal and distal arms 811 and 821 may be formed from Nitinol or any other feasible material. Additionally, the proximal ring 810 may have a first diameter and the distal ring 820 may have a second diameter, different than the first diameter. The different diameters may determine, at least in part, the density of the electric field associated with the nanosecond pulsed energy treatment. The proximal and distal rings 810 and 820 may be collapsed and withdrawn into the elongate catheter body 830 to allow for the placement of the applicator 800 with respect to the treatment area.

The proximal and distal rings 810 and 820 may be separated by a distance 840. In some examples, the proximal and distal rings 810 and 820 may telescope with respect to the elongate catheter body 830 and/or with respect to each other. Thus, by telescoping either or both the proximal and distal rings 810 and 820, the distance 840 may be changed. In some examples, the elongate applicator tool 102 may control the distance 840 by moving control wires, push rods, tendons, cables, or the like to telescope (position) the proximal ring 810 and or the distal ring 820.

The applicator 800 may be configured for bipolar operation. Pulsed energy may be transmitted between the proximal ring 810 and the distal ring 820. Thus, the proximal ring 810 may be an anode and the distal ring a cathode, or vice versa. In other examples, the applicator 800 may be configured for monopolar operation.

In some examples, the proximal ring 810 and the distal ring 820 may not form a continuous circle. Region 850 of the distal ring 820 is enlarged in FIG. 8B to show detail. The distal arm 821 may be bent to form the distal ring 820. For example, the distal ring 820 is bent toward the right as shown in the region 850. However, the tip of the distal ring 820 does not connect or attach to the distal arm 821. Leaving the tip of the distal ring 820 unconnected may provide increased flexibility for the distal ring 820. Although not shown, features of the proximal ring 810 and the proximal arm 811 may be similar.

Figure 8C:
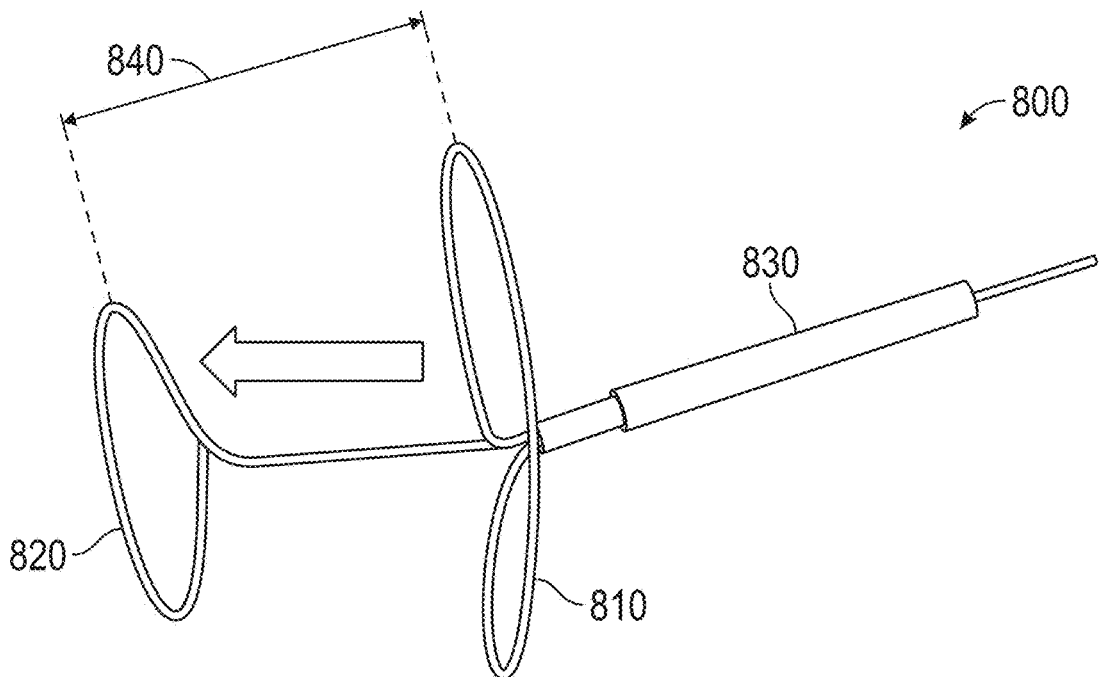
FIG. 8C shows another example of an applicator, in which the spacing between the electrodes is adjustable.

FIG. 8C shows another example and view of the applicator 800 similar to the applicator of FIG. 8A. In this view, the distance 840 between the proximal ring 810 and the distal ring 820 is shown as increased with respect to the distance 840 of the applicator 800 in FIG. 8A. For example, the proximal ring 810 and/or the distal ring 820 may be moved to increase the distance 840 between the respective rings. As described above, changing the distance 840 may affect the density of the electric field associated with the nanosecond pulsed energy treatment.

Figure 9:
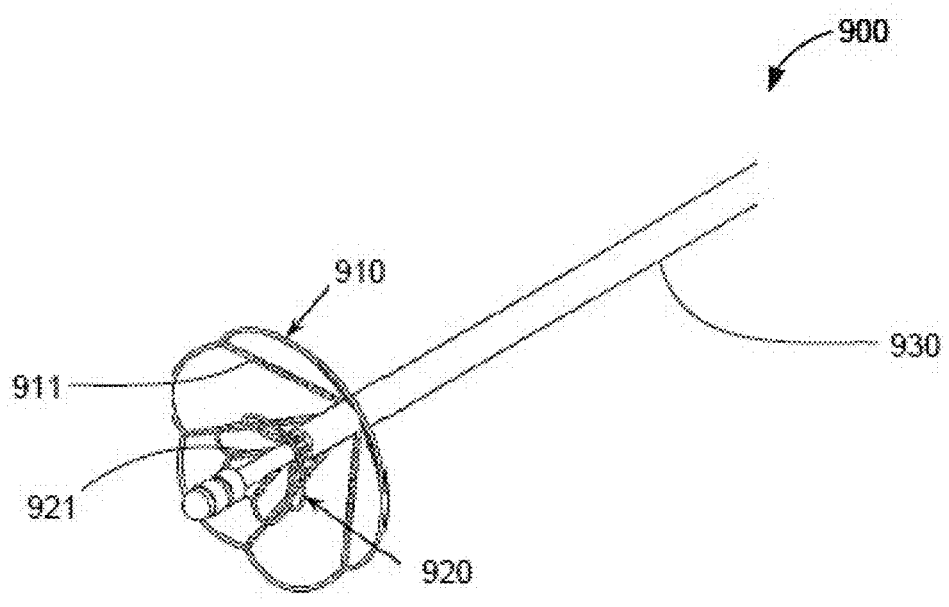
FIG. 9 shows another applicator configured to deliver nanosecond pulsed energy treatment to body vessel.

FIG. 9 shows another applicator 900 configured to deliver nanosecond pulsed energy treatment to body vessel. The applicator 900 may include a proximal ring 910, a proximal arm 911, a distal ring 920, a distal arm 921, and an elongate catheter body 930. The proximal and distal rings 910 and 920 and the proximal and distal arms 911 and 921 may be formed from Nitinol or any other feasible material. Additionally, the proximal ring 910 may have a first diameter and the distal ring 920 may have a second diameter, different than the first diameter. The different diameters may determine, at least in part, the density of the electric field associated with the nanosecond pulsed energy treatment. Although shown with six lobes, the proximal and distal rings 910 and 920 may include any feasible number of lobes.

The applicator 900 may be configured for bipolar operation. Pulsed energy may be transmitted between the proximal ring 910 and the distal ring 920. The proximal ring 910 may be a cathode and the distal ring 920 may be an anode (or vice versa). In another example, the applicator 900 may be configured for monopolar operation.

Figure 10:
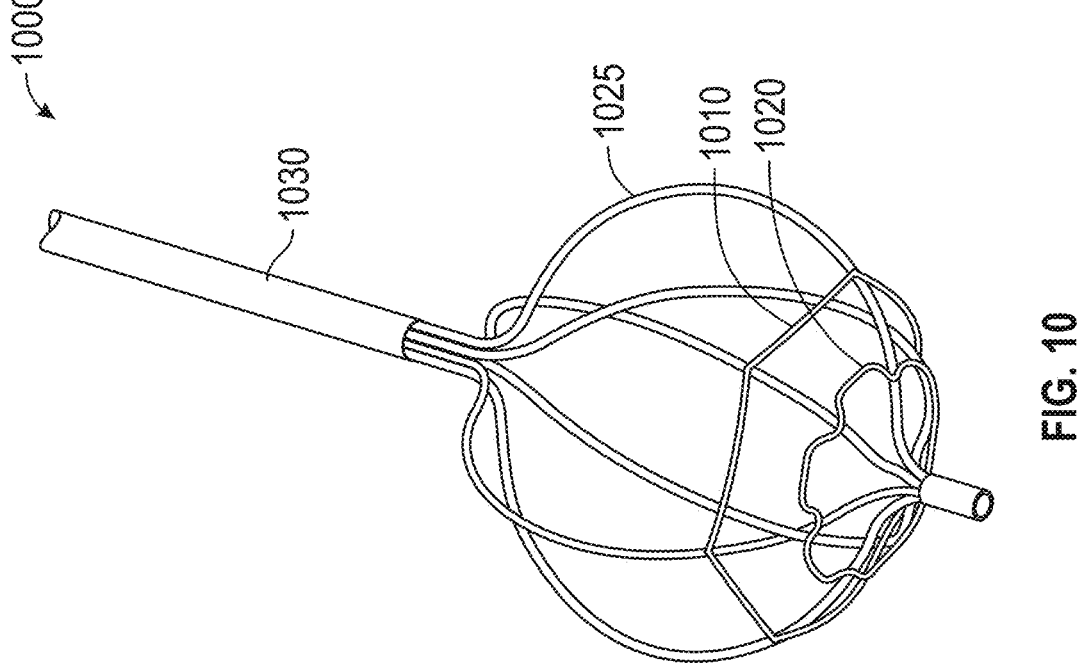
FIG. 10 shows another applicator configured to deliver nanosecond pulsed energy treatment to a body vessel.

FIG. 10 shows another applicator 1000 configured to deliver sub-microsecond pulsed energy treatment to a body vessel. The applicator 1000 may include a proximal ring 1010, a distal ring 1020, an expandable sphere 1025, and an elongate catheter body 1030. The proximal and distal rings 1010 and 1020 may be coupled to the system 100 (not shown) through conductors (also not shown) and the elongate catheter body 1030. The proximal and distal rings 1010 and 1020 and the expandable sphere 1025 may be formed from Nitinol or any other feasible material. In some examples, the proximal and distal rings 1010 and 1020 may be electrically insulated from the expandable sphere 1025.

The proximal and distal rings 1010 and 1020 may be disposed upon and/or coupled to the expandable sphere 1025. Thus, the expandable sphere 1025 and the proximal and distal rings 1010 and 1020 may be collapsed and withdrawn into the delivery catheter or sheath to allow for the positioning of the applicator 1000 with respect to the treatment area.

Additionally, the proximal ring 1010 may have a first diameter and the distal ring 1020 may have a second diameter, different than the first diameter. The different diameters may determine, at least in part, the density of the electric field associated with the nanosecond pulsed energy treatment. Although shown with six lobes, the proximal and distal rings 1010 and 1020 may include any feasible number of lobes.

The applicator 1000 may be configured for bipolar operation. The proximal ring 1010 may be an anode and the distal ring 1020 may be a cathode (or vice versa). In another example, the applicator 1000 may be configured for monopolar operation.

Figure 11:
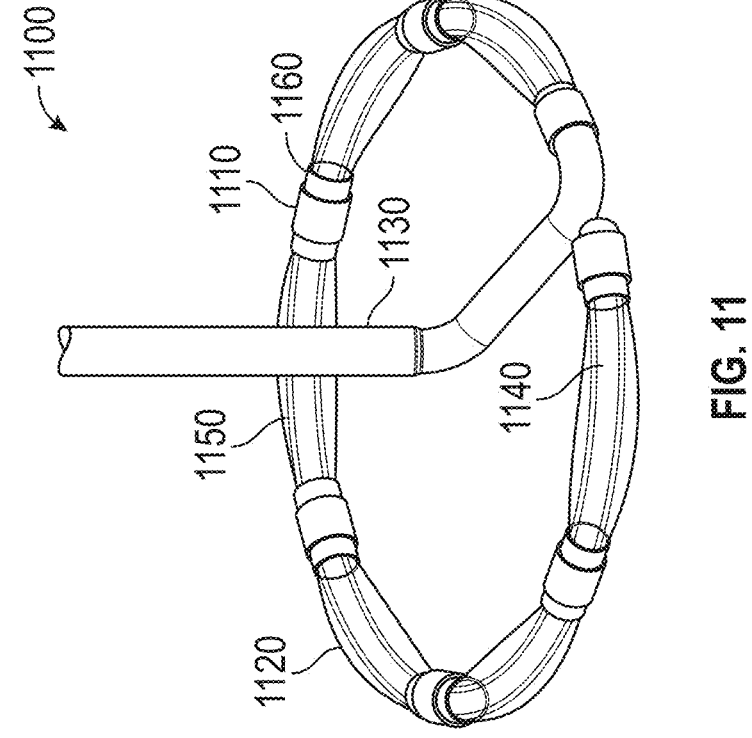
FIG. 11 shows another applicator configured to deliver nanosecond pulsed energy treatment to a body vessel.

FIG. 11 shows another applicator 1100 configured to deliver nanosecond pulsed energy treatment to a body vessel. The applicator 1100 may include one or more band electrodes 1110, a conductive braid 1120, an elongate catheter body 1130, a shape support member 1140, a tubular insulative member 1150, and one or more band insulators 1160. The one or more band electrodes 1110 and the conductive braid 1120 may be coupled to the system 100 (not shown) through conductors (also not shown) and the elongate catheter body 1130. In some examples, the one or more band electrodes 1110 may be coupled to each other.

The shape support member 1140, the conductive braid 1120, and the one or more band electrodes 1110 may be formed from Nitinol, or any other feasible material. In some examples, the shape support member 1140 may be formed substantially into a circle. In some cases, the diameter of the shape support member 1140 may be selected to substantially match a shape of a body vessel. The tubular insulative member 1150 may be disposed circumferentially around and adjacent to (e.g., touching) the shape support member 1140. The conductive braid 1120 may be disposed circumferentially around the tubular insulative member 1150 and may function as a first electrode of the applicator 1100. The conductive braid 1120 may be formed from a woven or braided conductive wire or any other feasible, conductive material. The one or more band electrodes 1110 may be disposed over the one or more band insulators 1160, which in turn are disposed over the conductive braid 1120. The one or more band electrodes 1110 and the one or more band insulators 1160 may be distributed on the conductive braid 1120. Although FIG. 11 shows six band electrodes 1110, in other examples, the applicator 1100 may include any feasible number of band electrodes.

The applicator 1100 may be configured for bipolar operation. Pulsed energy may be transmitted between the one or more band electrodes 1110 and the conductive braid 1120. The distance between band electrodes can vary, and as a result will make the braided electrode section between them shorter or longer and at the same time (given the diameter of the assembly stays the same) change the overall number of bipolar couples. In another example, the applicator 1100 may be configured for monopolar operation. Spacing between the one or more band electrodes 1110 and the conductive braid 1120 may determine, at least in part, the density of the electric field associated with the nanosecond pulsed energy treatment.

Figure 12:
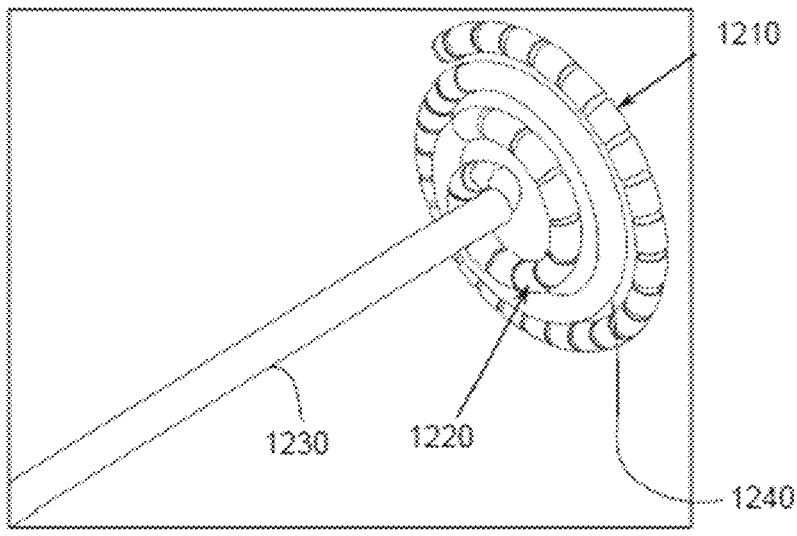
FIG. 12 shows another applicator configured to deliver nanosecond pulsed energy treatment to a body vessel.

FIG. 12 shows another applicator 1200 configured to deliver nanosecond pulsed energy treatment to a body vessel. The applicator 1200 may include one or more first electrodes 1210, one or more second electrodes 1220, an elongate catheter body 1230, and a spiral member 1240. The one or more first electrodes 1210, and the one or more second electrodes 1220 may be electrically coupled to the system 100 (not shown) through the elongate catheter body 1230. The spiral member 1240 and the one or more first and second electrodes 1210 and 1210 may be formed from Nitinol or any other feasible material. Additionally, the spiral member 1240 may spiral outward from the elongate catheter body 1230 while at the same time extending away from (e.g., distally away from) the elongate catheter body 1230, thereby forming a conical shape. This conical shape may enable the one or more first and second electrodes 1210 and 1220 to uniformly contact some tissue surfaces.

The one or more first and second electrodes 1210 and 1220 may be formed from any feasible conductive material. In some examples, the one or more first and second electrodes 1210 and 1220 may be wound spirally about the spiral member 1240. In other examples, the one or more first and second electrodes 1210 and 1220 may be individual bands electrically coupled together. Furthermore, an insulator (not shown) may be disposed between the one or more first and second electrodes 1210 and 1220, particularly when the spiral member 1240 is conductive. The first and second electrodes 1210 and 1220 and the spiral member 1240 may be withdrawn into the delivery catheter or sheath (not shown), or in some implementations, into an elongate catheter body 1230 to allow for the placement of the applicator 1200 with respect to the treatment area.

The applicator 1200 may be configured for bipolar operation. Pulsed energy may be transmitted between the one or more first electrodes 1210 and the one or more second electrodes 1220. Thus, the one or more first electrodes 1210 may be configured as a single cathode and the one or more second electrodes 1220 may be configured as a single anode (or vice versa). In another example, the applicator 1200 may be configured for monopolar operation. For example, the one or more first and second electrodes 1210 and 1220 may both be electrically coupled together and a return electrode (e.g., a conductive pad or electrode that may be in contact with the patient) may be used.

Figure 13:
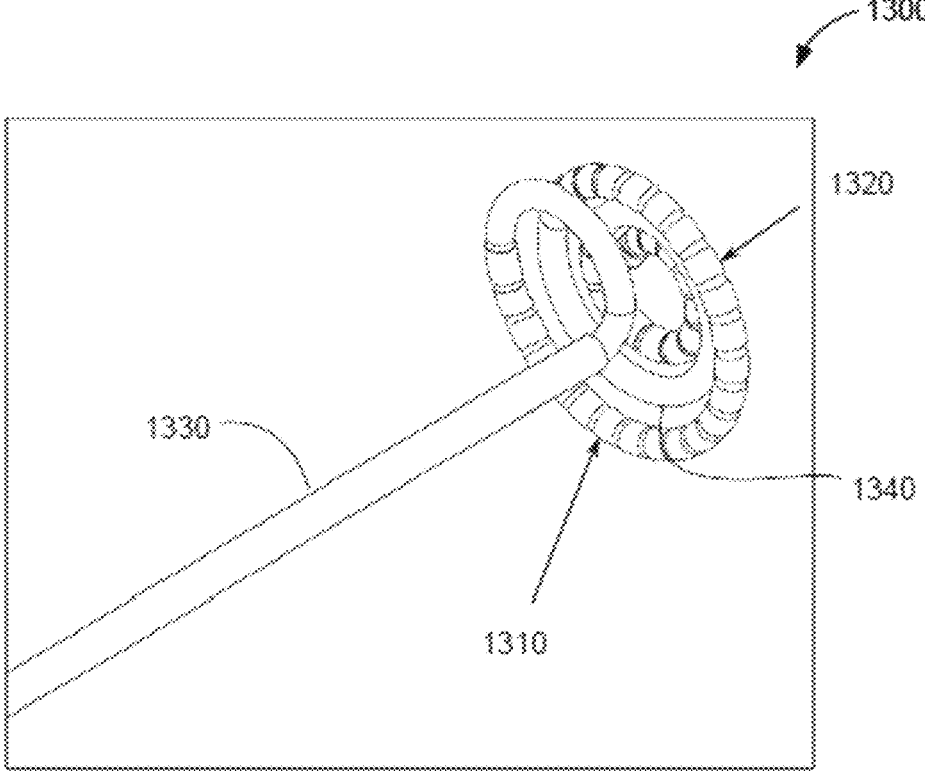
FIG. 13 shows another applicator configured to deliver nanosecond pulsed energy treatment to a body vessel.

FIG. 13 shows another applicator 1300 configured to deliver nanosecond pulsed energy treatment to a body vessel. The applicator 1300 may include one or more first electrodes 1310, one or more second electrodes 1320, an elongate catheter body 1330, and a spiral member 1340. The one or more first electrodes 1310 and the one or more second electrodes 1320 may be electrically coupled to the system 100 (not shown) through the elongate catheter body 1330. The spiral member 1340 and the one or more first and second electrodes 1310 and 1320 may be formed from Nitinol or any other feasible material. Additionally, the spiral member 1340 may spiral from an outer circumference toward an inner circumference while at the same time extending away from (e.g., distally away from) the elongate catheter body 1330, thereby forming an inverted (with respect to the applicator 1200) conical shape. This inverted conical shape may enable the one or more first and second electrodes 1310 and 1320 to uniformly contact some tissue surfaces.

The one or more first and second electrodes 1310 and 1320 may be formed from any feasible conductive material. In some examples, the one or more first and second electrodes 1310 and 1320 may be wound spirally about the spiral member 1340. In other examples, the one or more first and second electrodes 1310 and 1320 may be individual bands electrically coupled together. Furthermore, an insulator (not shown) may be disposed between the one or more first and second electrodes 1310 and 1320 and the spiral member 1340, particularly when the spiral member 1340 is conductive. The one or more first and second electrodes 1310 and 1320 and the spiral member 1340 may be collapsed and withdrawn into the delivery sheath (not shown) or, in some implementations, into an elongate catheter body 1330 to allow for the placement of the applicator 1300 with respect to the treatment area.

The applicator 1300 may be configured for bipolar operation. Pulsed energy may be transmitted between the one or more first electrodes 1310 and the one or more second electrodes 1320. Thus, the one or more first electrodes 1310 may be configured as an anode, and the one or more second electrodes 1320 may be configured as a cathode (or vice versa). In another example, the applicator 1300 may be configured for monopolar operation.

FIG. 14 shows another applicator 1400 configured to deliver nanosecond pulsed energy treatment to a body vessel. The applicator 1400 may include a plurality of first electrodes 1410, a plurality of second electrodes 1420, an elongate catheter body 1430, and a spiral member 1440. The plurality of first and second electrodes 1410 and 1420 may be electrically coupled to the system 100 (not shown) through the elongate catheter body 1430. The spiral member 1440 and the plurality of first and second electrodes 1410 and 1420 may be formed from Nitinol or any other feasible material. Additionally, the spiral member 1440 may spiral outward from the elongate catheter body 1430 while at the same time extending away from (e.g., distally away from) the elongate catheter body 1430, thereby forming a conical shape. This conical shape may enable the plurality of first and second electrodes 1410 and 1420 to uniformly contact some tissue surfaces.

The plurality of first and second electrodes 1410 and 1420 may be disposed in an alternating manner on the spiral member 1440. Changing the spacing between the plurality of first and second electrodes 1410 and 1420 may affect the density of the electric field associated with the nanosecond pulsed energy treatment. Furthermore, an insulator (not shown) may be disposed between the plurality of first and second electrodes 1410 and 1420 and the spiral member 1440, particularly when the spiral member 1440 is conductive.

The applicator 1400 may be configured for bipolar operation. Pulsed energy may be transmitted between the plurality of first electrodes 1410 and the plurality of second electrodes 1420. Thus, the plurality of first electrodes 1410 may be configured as an anode and the plurality of second electrodes 1420 may be configured as a cathode. In another example, the applicator 1400 may be configured for monopolar operation.

FIG. 15 shows another applicator 1500 configured to deliver nanosecond pulsed energy treatment to a body vessel. The applicator 1500 may include a first electrode 1510, a second electrode 1520, an elongate catheter body 1530, a third electrode 1540, a fourth electrode 1550, and a spiral member 1560. The first electrode 1510, a second electrode 1520, the third electrode 1540, and the fourth electrode 1550 may be electrically coupled to the system 100 (not shown) through the elongate catheter body 1530. The spiral member 1560 and the first, second, third, and fourth electrodes 1510, 1520, 1540, and 1550 may be formed from Nitinol or any other feasible material. Additionally, the spiral member 1560 may spiral outward from the elongate catheter body 1530 while at the same time extending away from (e.g., distally away from) the elongate catheter body 1530, thereby forming a conical shape. This conical shape may enable the first and second electrodes to uniformly contact some tissue surfaces.

The first, second, third and fourth electrodes 1510, 1520, 1540, and 1550 may be formed from any feasible conductive material. In some examples, the first, second, third and fourth electrodes 1510, 1520, 1540, and 1550 may be wound spirally about the spiral member 1560. Furthermore, an insulator (not shown) may be disposed between the first, second, third and fourth electrodes 1510, 1520, 1540, and 1550, particularly when the spiral member 1560 is conductive. In some examples, the first and third electrodes 1510 and 1540 may be electrically coupled together and the second and fourth electrodes 1520 and 1550 may be electrically coupled together.

The applicator 1500 may be configured for bipolar operation. Pulsed energy may be transmitted between two sets of electrodes. For example, the first and third electrodes 1510 and 1540 may be configured as a single cathode and the second and fourth electrodes 1520 and 1550 may be configured as a single anode (or vice versa). In another example, the applicator 1500 may be configured for monopolar operation.

FIG. 16 shows another applicator 1600 configured to deliver nanosecond pulsed energy treatment to a body vessel. The applicator 1600 may include a first electrode 1610, a second electrode 1620, an elongate catheter body 1630, a third electrode 1640, a fourth electrode 1650, a supporting member 1660, and a connecting member 1670. The first electrode 1610, the second electrode 1620, the third electrode 1640, and the fourth electrode 1650 may be electrically coupled to the system 100 (not shown) through the elongate catheter body 1630. The first, second, third and fourth electrodes 1610, 1620, 1640, and 1650 may be disposed upon the supporting member 1660 which may emerge from the elongate catheter body 1630. In some examples, an insulator (not shown) may be disposed between the first, second, third, and fourth electrodes 1610, 1620, 1640, and 1650, particularly when the supporting member 1660 is conductive. The connecting member 1670 may couple opposing ends of the supporting member 1660. Although only four electrodes are shown, in other examples, the applicator 1600 may include any feasible number of electrodes.

The first, second, third, and fourth electrodes 1610, 1620, 1640, and 1650, the supporting member 1660, and the connecting member 1670 may be formed from Nitinol or any other feasible material. The connecting member 1670 may be smaller and/or more flexible than the supporting member 1660 to enable the supporting member 1660 and the first, second, third, and fourth electrodes 1610, 1620, 1640, and 1650 to be more easily withdrawn into the elongate catheter body 1630 to allow for the placement of the applicator 1600 with respect to the treatment area.

The applicator 1600 may be configured for bipolar operation. Pulsed energy may be transmitted between two sets of electrodes. For example, pulsed energy may be transmitted between the first and third electrodes 1610 and 1640, forming a combined anode, and the second and fourth electrodes 1620 and 1650, forming a combined cathode, or vice versa. In another example, the applicator 1600 may be configured for monopolar operation.

Figure 17A:
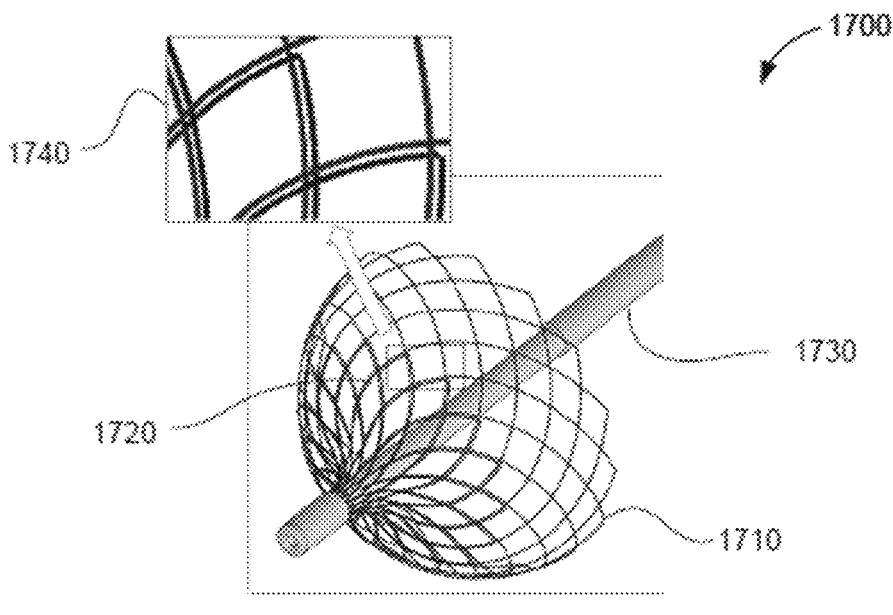
FIG. 17A shows another applicator configured to deliver nanosecond pulsed energy treatment to a body vessel.

FIG. 17A shows another applicator 1700 configured to deliver treatment to a body vessel. The applicator 1700 may include a first insulated conductor 1710, a second insulated conductor 1720, and an elongate catheter body 1730. The first and second insulated conductors 1710 and 1720, and the elongate catheter body 1730 may be formed from Nitinol or any other feasible material. Furthermore, the first insulated conductor 1710 and the second insulated conductor 1720 may be woven into a basket. In some examples, the first insulated conductor 1710 and the second insulated conductor 1720 may be woven together in the distal section of the basket (as shown, the distal section is closer circumferentially to the shaft 1730). A double braid region of the basket is shown in the enlarged region 1740. The basket formed by the first insulated conductor 1710 and the second insulated conductor may be collapsed and withdrawn into the delivery catheter (not shown) to allow for the placement of the applicator 1700 with respect to the treatment area.

Figure 17B:
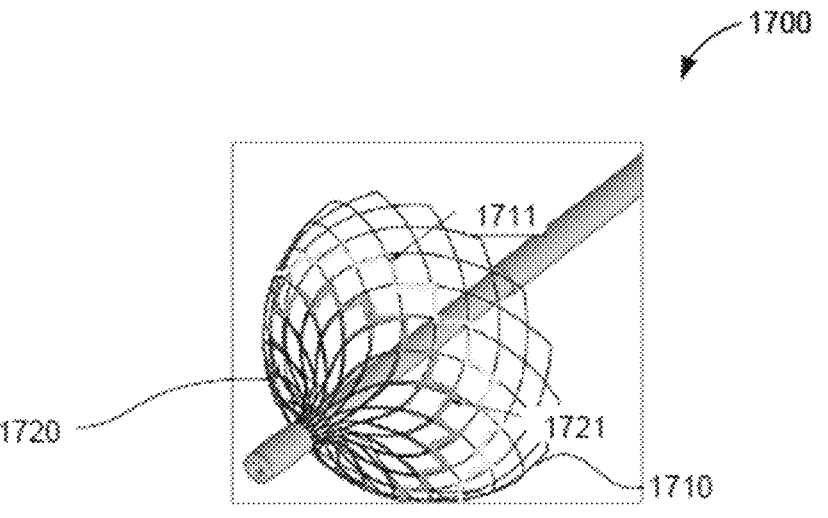
FIG. 17B shows further details of the applicator of FIG. 17A.

FIG. 17B shows another view of the applicator 1700 of FIG. 17A. Regions of insulation of the first insulated conductor 1710 and the second insulated conductor 1720 may be selectively removed to expose associated bare conductors. Thus, insulation removed from the first insulated conductor 1710 may form a first electrode 1711 and insulation removed from the second insulated conductor 1720 may form a second electrode 1721.

The applicator 1700 may be configured for bipolar operation. Pulsed energy may be transmitted between two sets of electrodes. For example, pulsed energy may be transmitted between the first electrode 1711 and the second electrode 1721. Thus, the first electrode 1711 may be configured as an anode and the second electrode 1721 may be configured as a cathode (or vice versa). In another example, the applicator 1700 may be configured for monopolar operation.

Figure 18:
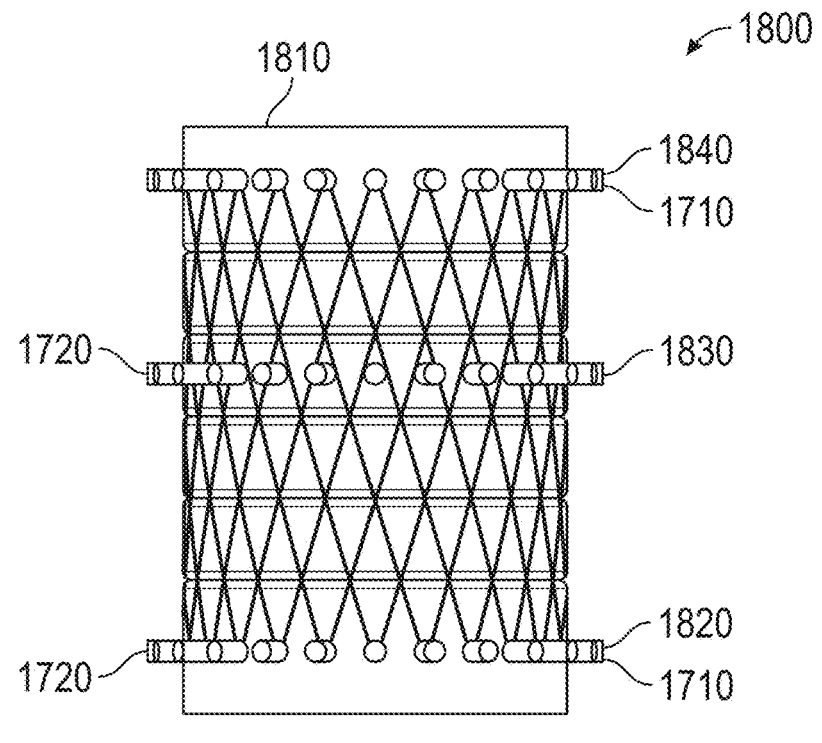
FIG. 18 shows one example of a fixture for fabricating the applicator of FIG. 17A.

FIG. 18 shows one example of a fixture 1800 for fabricating the applicator 1700 of FIG. 17A. The fixture 1800 may include a cylinder 1810, a first group of pins 1820, a second group of pins 1830, and a third group of pins 1840. To fabricate the applicator 1700, the first insulated conductor 1710 is selectively wrapped between the first and third group of pins 1820 and 1840. In a similar manner, the second insulated conductor 1720 is selectively wrapped between the first and second group of pins 1820 and 1830. After wrapping the first insulated conductor 1710 and the second insulated conductor 1720 around the cylinder 1810, insulation may be selectively removed from the first insulated conductor 1710 and the second insulated conductor 1720 to form the first electrode 1711 and the second electrode 1721.

Figure 19:
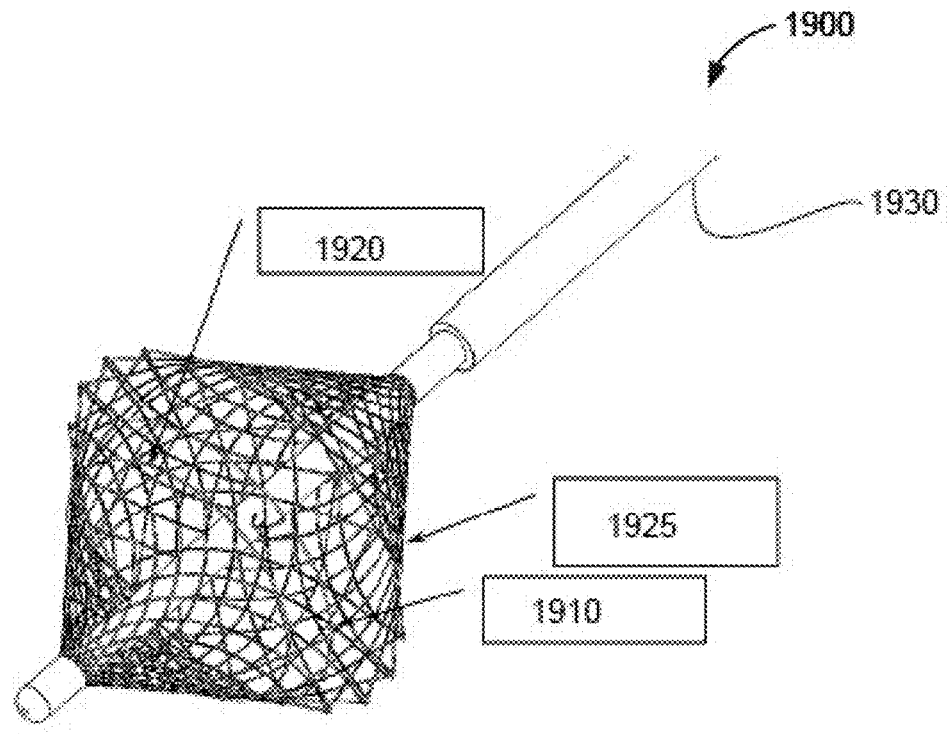
FIG. 19 shows another applicator configured to deliver nanosecond pulsed energy treatment to a body vessel.

FIG. 19 shows another applicator 1900 configured to deliver nanosecond pulsed energy treatment to a body vessel. The applicator 1900 may include a first electrode 1910, a second electrode 1920, a braid member 1925, and an elongate catheter body 1930. The first electrode 1910, the second electrode 1920, and the braid member 1925 may be formed from Nitinol or any other feasible material. In some examples, the braid member 1925 may be or made from electrically nonconductive material. The braid member 1925 may expand (as shown) to deploy the first electrode 1910 and the second electrode 1920 such that the first electrode 1910 may form a distal circular electrode and the second electrode 1920 may form a proximal circular electrode. Although only two electrodes are shown, in other examples, the applicator 1900 may include any feasible number of electrodes. The braid member 1925 may be collapsed and withdrawn into the delivery sheath to allow for the placement of the applicator 1900 with respect to the treatment area.

The applicator 1900 may be configured for bipolar operation. Pulsed energy may be transmitted between two sets of electrodes. For example, pulsed energy may be transmitted between the first electrode 1910 and the second electrode 1920. Thus, the first electrode 1910 may be configured as a cathode and the second electrode 1920 may be configured as an anode (or vice versa). In another example, the applicator 1900 may be configured for monopolar operation.

Figures 20, 21:
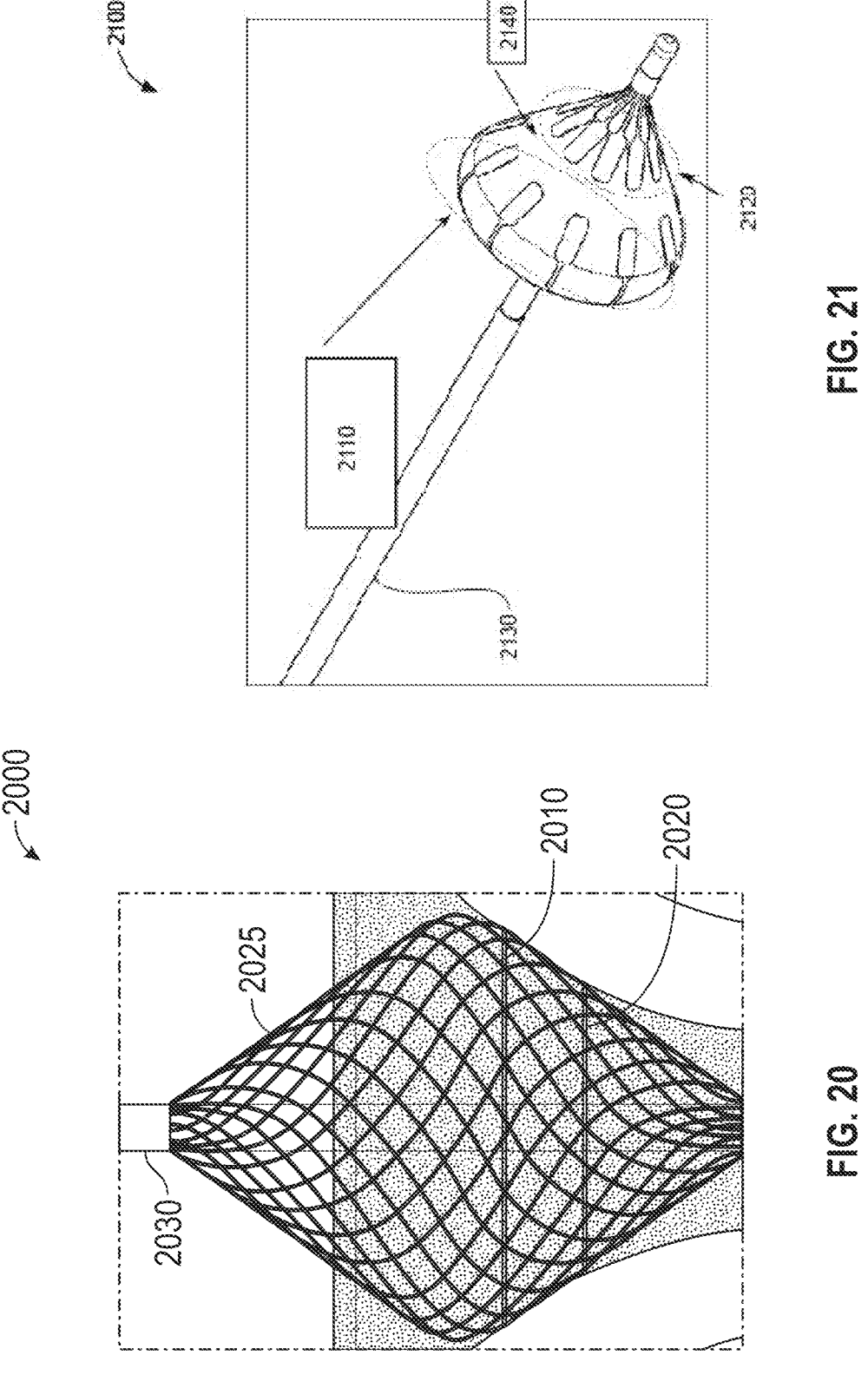
FIG. 20 shows another applicator configured to deliver nanosecond pulsed energy treatment to a body vessel.
FIG. 21 shows another applicator configured to deliver nanosecond pulsed energy treatment to a body vessel.

FIG. 20 shows another applicator 2000 similar to the applicator of FIG. 19 and configured to deliver treatment to a body vessel. The applicator 2000 may include a first electrode 2010, a second electrode 2020, a braid member 2025, and an elongate catheter body 2030. The first electrode 2010, the second electrode 2020, and the braid member 2025 may be formed from Nitinol or any other feasible material. The braid member 2025 may expand (as shown) to deploy the first electrode 2010 and the second electrode 2020 such that the first electrode 2010 may form a proximal electrode and the second electrode 2020 may form a distal electrode. Although only two electrodes are shown, in other examples, the applicator 2000 may include any feasible number of electrodes. The first and second electrodes 2010 and 2020 and the braid member 2025 may be collapsed to allow for the placement of the applicator 2000 with respect to the treatment area.

The applicator 2000 may be configured for bipolar operation. Pulsed energy may be transmitted between two sets of electrodes. For example, pulsed energy may be transmitted between the first electrode 2010 and the second electrode 2020. Thus, the first electrode 2010 may be configured as an anode and the second electrode 2020 may be configured as a cathode (or vice versa). In another example, the applicator 2000 may be configured for monopolar operation.

FIG. 21 shown another applicator 2100 configured to deliver nanosecond pulsed energy treatment to a body vessel. The applicator 2100 may include a first set of electrodes 2110, a second set of electrodes 2120, an elongate catheter body 2130, and an expandable member 2140. The first set of electrodes 2110 and the second set of electrodes 2120 may be formed from Nitinol or any other feasible material. In some examples, the expandable member 2140 may be a balloon that may be inflated to expand and deploy the first and second set of electrodes 2110 and 2120. In some cases, the expandable member 2140 and the first and second set of electrodes 2110 and 2120 may be collapsed to allow for the placement of the applicator 2100 with respect to the treatment area.

The applicator 2100 may be configured for bipolar operation. Pulsed energy may be transmitted between two sets of electrodes. For example, pulsed energy may be transmitted between the first electrode 2110 and the second electrode 2120. In another example, the applicator 2100 may be configured for monopolar operation.

Also described herein are apparatuses (e.g., applicators, applicator devices, etc.) that are configured to apply bipolar application of electrical energy, and in particular, sub-microsecond (e.g., nanosecond), pulsed electrical energy within a tubular structure such as a lumen of the body (also referred to as a body vessel). As mentioned above, in general a tubular structure may be a lumen such as a blood vessel (vein, artery, etc.), an airway such as the nasal passages, oral cavity, sinuses, larynx, trachea, bronchial tubes, etc., an organ such the heart (atrium, ventricle, etc.), the lungs, bladder, etc. Any of these apparatuses may be configured for bipolar application of the electrical energy to the tubular structures and may include an elongate body having a distal end region that includes a plurality of longitudinally extending ribs that are configured to expand outwards. In any of these examples the elongate body may be a catheter. The elongate body may include one or more channels, including a guidewire lumen. The ribs may be part of an expanding/contracting frame. A plurality of these ribs may be arranged radially around the circumference of the distal end region of the apparatus. Each of the ribs may correspond to an electrode. In some examples the apparatus may be configured as a bipolar device, in which a first subset of the ribs has a first polarity, and a second subset of the ribs has a second polarity. In some examples ribs of opposite polarity may alternate.

The ribs may be attached at a proximal end to a first elongate member forming the elongate body. In some examples the ribs may be attached at a distal end to a second elongate member that is axially slidably within the first elongate member. The ribs may be expanded (e.g., deploying the apparatus) by sliding the first elongate member relative to the second elongate member (or vice versa) to shorten the distance between the distal and proximal ends of the ribs. Similarly, the ribs may be retracted (e.g., constricting the apparatus) by sliding the first elongate member relative to the second elongate member (or vice versa) to increase the distance between the distal and proximal ends of the ribs. In some examples the ribs may be biased (or may be in communication with a bias) tending to expand the ribs outwards. Alternatively in some examples the ribs may be biased (or may be in communication with a bias) that tends to collapse the ribs inward. For example, the ribs may be formed of a shape memory alloy (e.g., a nickel titanium alloy, such as Nitinol) that is shape-set to be in the expanded configuration or alternatively the collapsed configuration. In some examples the ribs may be in communication with a bias such as a leaf spring, balloon, etc.

The ribs may be un-insulated over a portion of the length of each rib, from which energy may be applied. For example, each rib may be un-insulated over a middle region of the rib extending a length, L, which may be referred to as the active length or active region of each rib. In some examples only the outward-facing side of each rib is un-insulated. Any appropriate electrical insulator may be used, including polymeric insulators, and in particular biocompatible polymeric insulators.

Figure 22A:
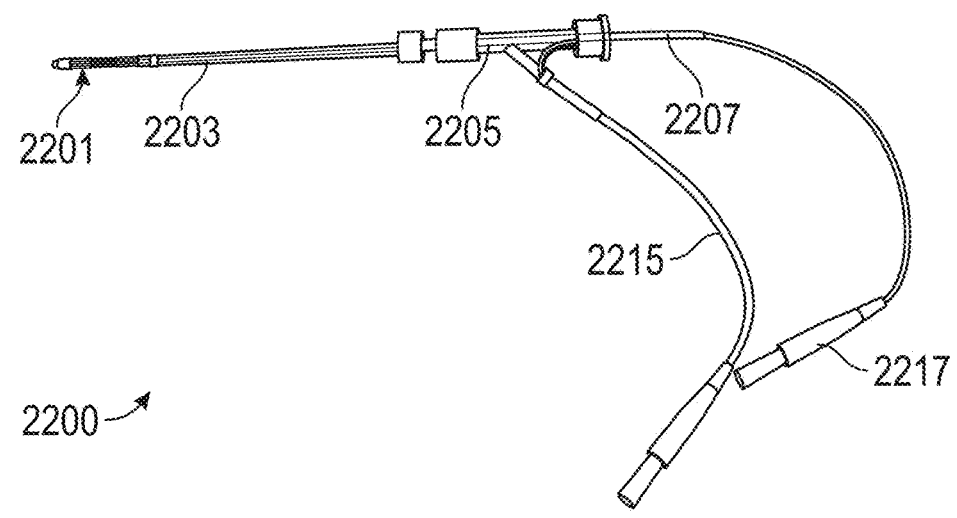
FIGS. 22A-22C illustrate one example of an apparatus for delivering pulsed electrical energy within a lumen.
Figure 22B:
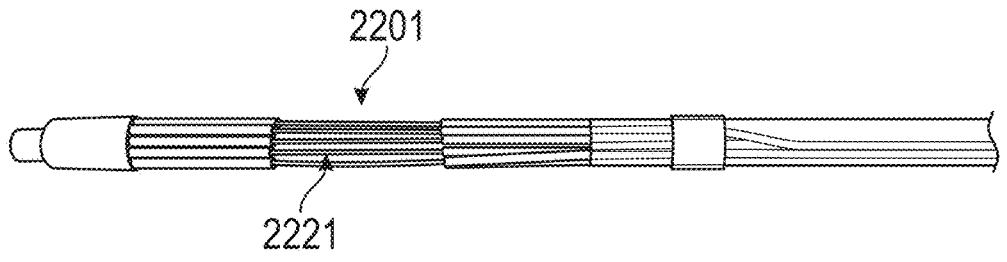

For example, FIG. 22A illustrates one example of an apparatus as described herein, configured for delivering sub-microsecond (e.g., nanosecond) pulsed energy within a tubular structure. In FIG. 22A the apparatus 2200 includes an elongate body 2203 extending proximally to distally. The elongate body is configured to be inserted into a body lumen. In some examples the elongate body may be flexible; in some examples the elongate body is rigid. The elongate body may be curved or steerable (e.g., using one or more tendons). The apparatus also includes an applicator region 2201 at the distal end region of the elongate body. In FIGS. 22A and 22B the applicator region is shown in a collapsed (un-expanded) configuration. The applicator region may include a plurality of expandable ribs 2221 that are each configured to expand outwards within the lumen from a collapsed configuration. For example, in FIG. 22B the collapsed ribs are shown collapsed down so that the cross-sectional diameter of the applicator region has approximately the same diameter as the rest of the elongate body.

Figure 22C:
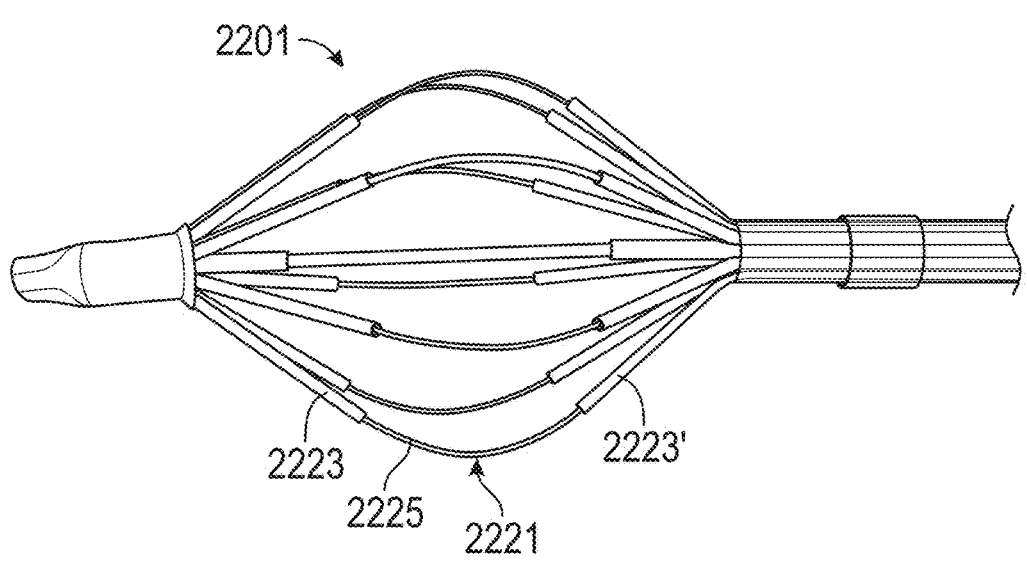

FIG. 22C shows the applicator region 2201 in an expanded configuration in which the plurality of ribs is extended radially outwards in a curve. In this example eight ribs 2221 are shown, though any appropriate number (e.g., two, three, four, five, six, seven, eight, nine, ten, eleven, twelve, thirteen, fourteen, fifteen, sixteen, etc.) may be used. Each rib includes an un-insulated active region 2225, in which the conductive material is exposed. The ribs may be formed of any appropriate material, including, e.g., stainless steel, nickel titanium (e.g., Nitinol), etc. In FIG. 22C, each rib 2221 includes a centrally positioned active region that is flanked on either side by insulated regions 2223, 2223'. The active region may be any appropriate length, such as between 1 mm and 3 cm (e.g., between 1 mm and 2 cm, between 1 mm and 1.5 cm, between 1 mm and 10 mm, between 1 mm and 8 mm, between 2 mm and 10 mm, between 2 mm and 8 mm, between 2 mm and 7 mm, etc.).

In general, the plurality of ribs may include two subsets, each having a different polarity. In some examples a first subset of the plurality of ribs in the active region is configured to have a first polarity and a second subset of the ribs is configured to have a second polarity. Thus, energy (e.g., pulsed, sub-microsecond energy) may be applied between the two subsets of ribs. In this example, every other rib (or spline) arranged radially around the active region may have a different polarity, and ribs of the same polarity may be electrically coupled together. Thus the polarity alternates around the active region.

In FIGS. 22A-22C, the plurality of ribs forming the expandable active region are coupled to a pair of elongate members that form the elongate body extending proximally to distally so that relative movement of the first elongate member and the second elongate member may result in expanding or contracting the active region. For example, the proximal end of each of the plurality of ribs may be connected to a first (e.g., in some examples, outer) elongate member 2205 and the distal end of the plurality of ribs may be connected to a second (e.g., in some examples, inner) elongate member 2207. The second elongate member is coaxially positioned relative to the first elongate member and may slide proximally to distally within the first elongate member in order to expand or contract the active region.

The apparatus also includes a pair of electrical connectors that couple to the pulse generator for applying power to the apparatus. For example, in FIG. 22A a first electrical connector 2215 is shown coupled to the first elongate member and may couple to a first subset of the ribs (having a first polarity). The second electrical connector 2217 is connected to the second elongate member and may couple to a second subset of the ribs (having a second polarity). Alternatively, in some examples the same applicator may be used to apply a single polarity from all of the ribs, and a separate return pad (e.g., ground pad like the pad 133 shown in FIG. 1) may be used (not shown).

The example device shown in FIGS. 22A-22C includes eight (8) stainless steel ribs that are each approximately 0.015" by 0.005" (e.g., 0.38 mm×0.13 mm). Each rib is insulated by a polymeric insulator, such as a polyimide to provide electrical insulation, in order to prevent arcing and expose only a necessary length of the rib (also referred to herein as a spline or a strut) for energy delivery.

FIGS. 23A-23F illustrate another example of an apparatus similar to that shown in FIG. 22A-22C. In this example, the distal active region of the apparatus 2301 is shown in the collapsed configuration as in FIG. 22A. The apparatus also includes an elongate body 2303 that includes a first elongate member (outer elongate member 2305) and a second (e.g., inner) elongate member 2307. The first elongate member is coupled to the proximal end of the active region and the second elongate member is coupled to the distal end of the active region. Thus, pulling the second elongate member proximally and/or pushing the first elongate member distally may shorten the distance between the proximal and distal ends of the active regions (e.g., the ribs or splines) and expand the ribs outwards.

Figures 23A, 23B, 23C, 23D, 23E, 23F:
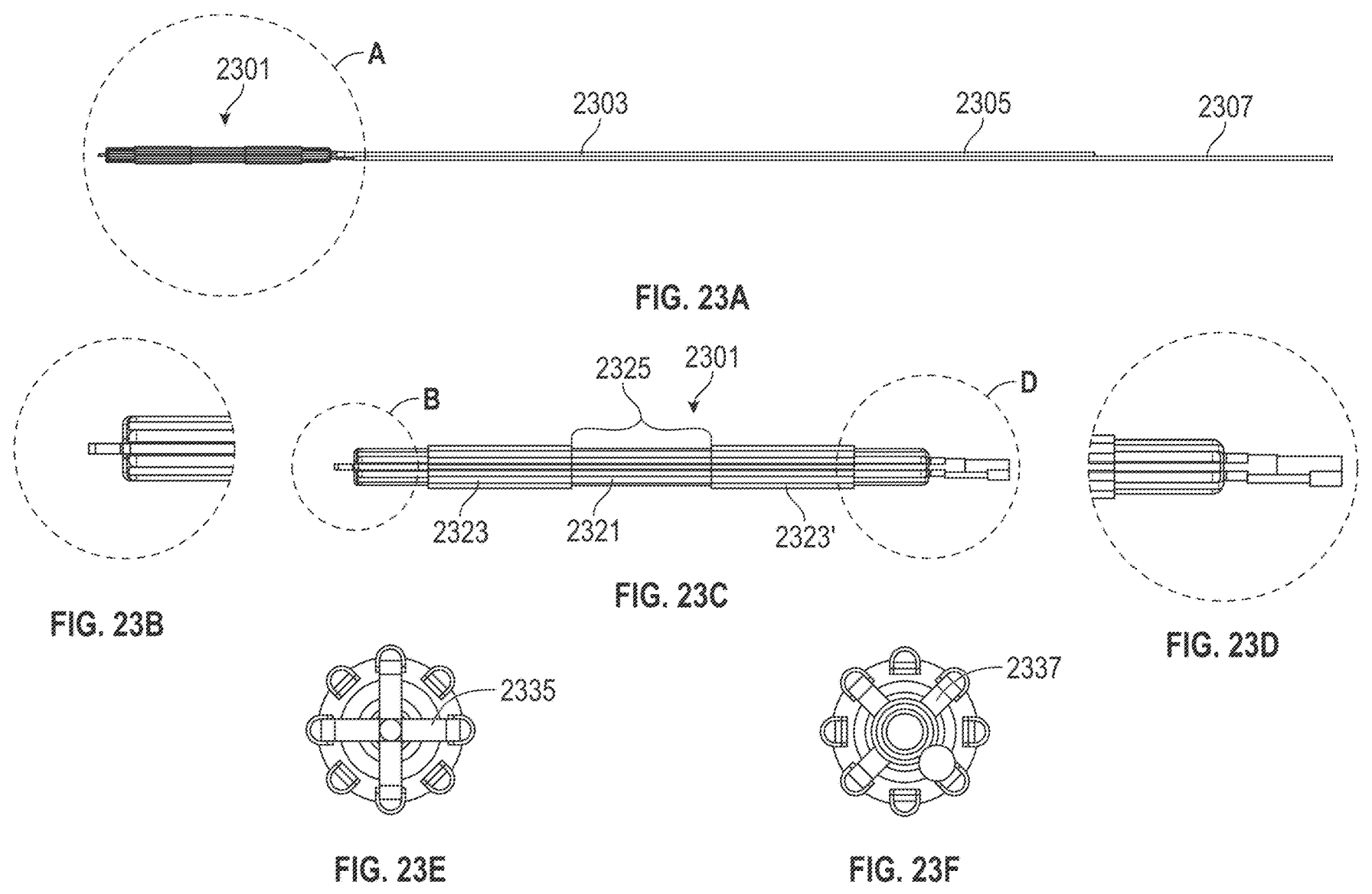

FIG. 23B shows an enlarged view of the active region 2301 including a plurality of ribs 2321, shown in the collapsed (un-expanded) configuration. FIGS. 23C and 23D illustrate enlarged end views of the ribs forming the active region described above, and FIGS. 23E and 23F show end views of each of the distal and proximal ends, respectively. FIGS. 23E and 23F illustrate one example of the electrical connections between ribs of the same polarity alternating around the perimeter. In FIG. 23E, showing an end view of the distal end of the active region, every other rib or spline is electrically coupled 2335, forming the first subset of splines. FIG. 23F shows an end view of the proximal end of the active region showing the electrical connection 2337 of the second subset of splines. In the example of FIGS. 23A-23F each spline 2321 includes a central active region 2325 that is flanked by a pair of insulated regions 2323, 2323'. In FIGS. 23A-23F, the electrical distribution may be configured to use high voltage and return voltage wire. FIG. 23E shows the distal end of the four flat wires forming the splines of the first subset, that are bent and soldered together for one polarity. The proximal end of the four flat wires forming the second subset of splines may be bent and soldered together to form the other polarity, as shown in FIG. 23F.

As mentioned, the inner, second elongate member may be moved (e.g., pulled/pushed) relative to the first elongate member to expand and contract the splines (and thus the diameter of the active region). For example, a selected diameter may be set by the user (expanding within the lumen of the vessel) and the expansion state of the apparatus may be locked in place, e.g., using a lock or latching mechanism securing the first elongate member relative to the second elongate member. Once in position, energy can be applied.

Figure 24A:
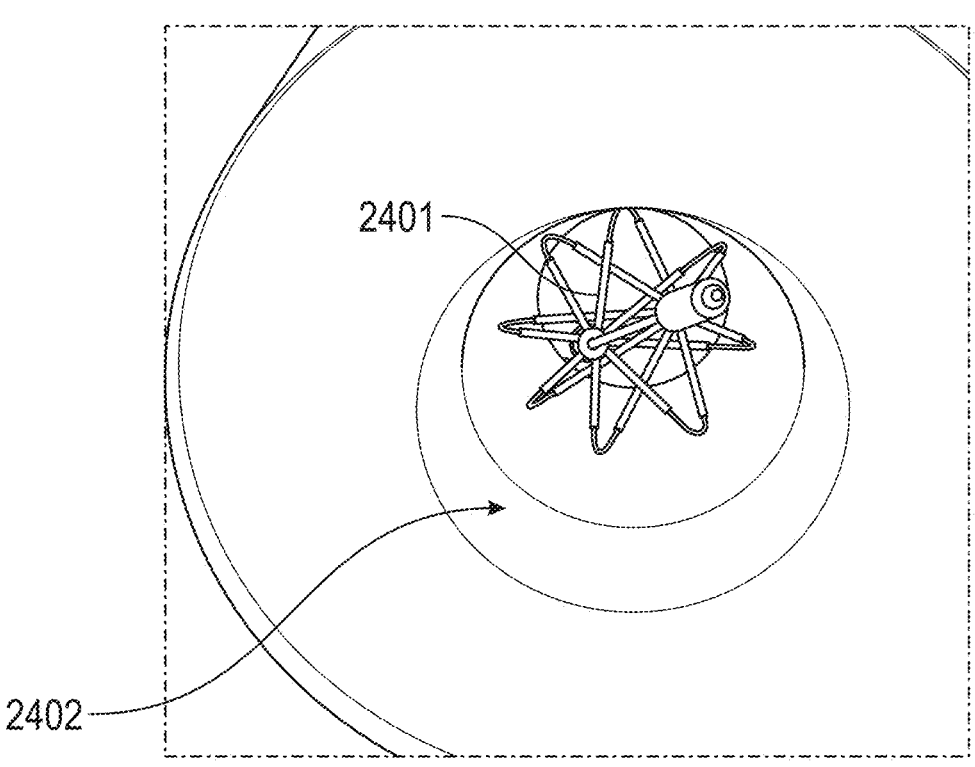
FIGS. 24A-24E illustrate treatment of a model tissue using an apparatus such as the one shown in FIG. 22A-22C.
Figure 24B:
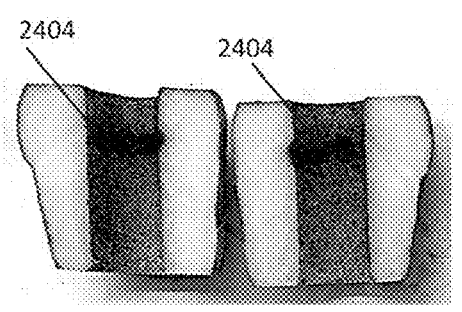
Figure 24C:
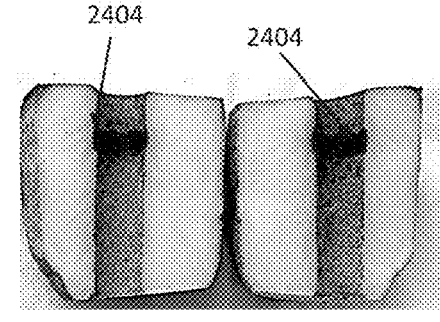
Figure 24D:
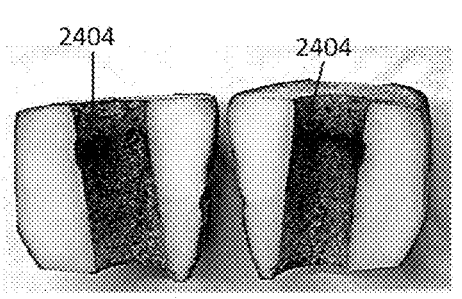
Figure 24E:
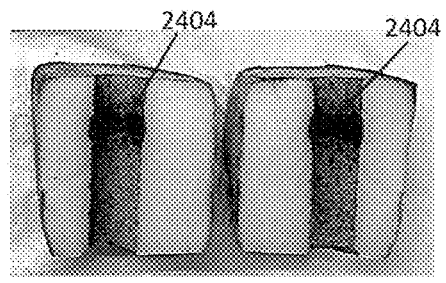

For example, FIGS. 24A-24E illustrate one example of an apparatus, such as the apparatuses shown in FIGS. 22A-22C and 23A-23F, in operation, applying pulsed, sub-microsecond energy to an example of a tissue. In this example, the sample tissue is a potato, into which a lumen has been formed for insertion of one example of the apparatus. FIG. 24A shows an end view of a lumen 2402 through a sample tissue into which apparatus 2401 has been inserted and expanded, as described above. In this example the eight (8) ribs are expanded until they just contact the walls of the simulated lumen. The bipolar apparatus was constructed as described above and inserted into the lumen and expanded. FIGS. 24B and 24D illustrate 20 mm lumen diameters while FIGS. 24C and 24E show 14 mm lumen diameters. As shown in FIGS. 24B-24E all of the parameters and devices tested resulted in circumferential treatment 2404 around the perimeter of the lumen. All of these examples were tested using pulses in a nanosecond range (e.g., between 1 and 1000 ns) and a voltage of about 2,500 V.

In the examples shown in FIGS. 22A-22C and 23A-23F, the apparatuses include an exposed (active) portion of each rib (e.g., spline) that is located in the middle of said spline. Alternatively, in some examples the location of the exposed active portion can be biased towards distal or proximal end of the electrode assembly. If ribs (splines) are made from a shape memory material, such as Nitinol, the ribs may be shape-set to the preferred configuration.

For example, FIGS. 25 and 26 illustrates examples of apparatuses 2500, 2600 in which the exposed active region of the ribs of the expandable/collapsible frame forming the applicator region are biased towards the distal end. In FIG. 25, the applicator region has an approximately teardrop shape in longitudinal cross-section. Thus, the applicator region is configured to expand outwards into shape having a larger cross-sectional area, relative to a long axis of the applicator region, that is larger distally than proximally. Each rib (spline) 2521 has a curved shape in the expanded configuration with slope of the distal-facing region being larger (steeper) than the slope of the proximal portion. As described above, each rib also includes an exposed active region 2525 that is flanked by insulated region 2623, 2623'. FIG. 26 is similar to the example shown in FIG. 25, but the entire distal end region of each rib 2621 is exposed (un-insulated) 2625, and only the proximal end of the rib is insulated 2623.

The apparatuses shown in FIGS. 22A-22C, 23A-23F, 25 and 26 may be expanded by coupling the applicator region proximally to a first elongate member that is axially slidable relative to a second elongate member which is coupled to the distal end of the applicator region, as described above. Alternatively or additionally, any of these devices may be expanded by pushing distally out of a catheter or sleeve so that the applicator region expands (e.g., self-expands); the ribs of the applicator region may be biased to expand radially outwards as they are driven distally out of the catheter/sleeve. Similarly, the applicator region may be collapsed by pulling proximally back into the catheter/sleeve. The examples shown in FIGS. 25 and 26 are configured in this manner, such that the elongate body does not necessarily extend into the expandable applicator region. In this example the active regions of each rib (spline) may be coupled electrically at the proximal end, including electrically coupling a first subset of the active regions to a first polarity and a second subset of the active regions to a second polarity; in some examples ribs having the first polarity may alternate with ribs having the second polarity.

Any of the apparatuses described herein may be configured to treat a sidewall of a lumen, and/or may be configured to treat a forward (distal) facing region of the tissue. For example, the apparatuses described herein may be configured to treat the tissue around the antrum of the pulmonary veins (PV) in the left atrium (LA) of the heart, e.g., to treat atrial fibrillation (AFIB) via PV Isolation (PVI). An example of this treatment using an apparatus such as the one shown in FIG. 26 is illustrated in FIG. 27.

For example, to gain access to the heart's LA, a puncture of the femoral vein may be performed using a needle under fluoroscopic and/or ultrasound guidance. After the puncture under fluoroscopic guidance, a guidewire (e.g., a 0.032-inch J-tip guidewire) may be advanced. The needle may be removed, and a sheath introducer (e.g., an 8-12 F introducer) may then be inserted into the vein and flushed. A transseptal sheath and dilator may be advanced over the guidewire to the superior vena cava (SVC). Once the sheath has reached 3 to 4 cm superior to the cavoatrial junction, the wire may be removed. The transseptal puncture needle may be advanced under fluoroscopic guidance until it reaches the sheath tip. The needle may then be advanced with the stylet inserted until it reaches 4 cm from the tip. The stylet prevents the needle tip from scraping the inner lumen of the sheath. The stylet can then be removed. The puncture may then be performed, and the sheath may be advanced into the LA. An apparatus (e.g., a catheter including the apparatus 2600 shown in FIG. 26) including electrodes formed as part of the applicator region may be introduced in the LA through the sheath. The active regions (e.g., electrodes) of the expanded or partially expanded ribs can be pushed against the wall of the LA 2718 surrounding the pulmonary vein 2719 as shown in FIG. 27. In any of the apparatuses described herein the distal end of the device may be deflectable or fully articulatable. For example, the elongate body may include one or more tendons for articulating the distal end (the applicator region). Thus, positioning of the electrodes can be aided by a deflectable or fully articulated distal end of the catheter, controlled via a steering mechanism in the handle and pull-wires (tendons) located within the shaft of the elongate body.

The location of the catheter within the body can be verified using fluoroscopy and/or ultrasound (e.g., ICE), as well as impedance and/or magnetic localization enabled by additional electrodes and/or magnetic sensor(s) of the catheter. The contact between the active regions (e.g., electrodes) of the apparatus and the tissue (e.g., the LA) wall can be verified, for example, by acquiring signals generated by the cardiac tissue. Electrodes incorporated into the catheter design for impedance-based localization can be used for this purpose as well. After the desired position and contact of the electrodes is confirmed, the energy (e.g., sub-microsecond pulsing, microsecond pulsing, RF, etc.) may be applied to achieve the desired therapeutic effect, including in some examples non-thermal ablation of all or a selected portion of the target tissue. The active electrodes and/or the electrodes used for the impedance-based localization and/or contact assessment prior to ablation can be used for the post-ablation signal acquisition. In some examples the tissue-contacting electrodes can be used for impedance-based localization and contact assessment. For example, the absence of electrical signals from the cardiac tissue may indicate an effective acute effect from the ablation. The apparatus may be repositioned one or more times and the application of energy may be repeated over additional region of the tissue (e.g., the LA areas surrounding other pulmonary veins). For example, when treating in the LA, a complete PVI can be achieved.

In some examples the ribs may be configured so that the un-insulated regions form substantially flat region, such as a region that is substantially parallel (e.g., within about +/−8 degrees, within about +/−5 degrees, within about +/−4 degrees, within about +/−3 degrees, within about +/−2 degrees, within about +/−1 degree, etc.) to the long axis of the distal end region, such as the region that extends through the plurality of ribs. For example, each rib may include hinge regions adjacent to one or both ends of the un-insulated (active) region that allow the rib to bend or flex so that the un-insulated region is substantially flat.

Figure 28A:
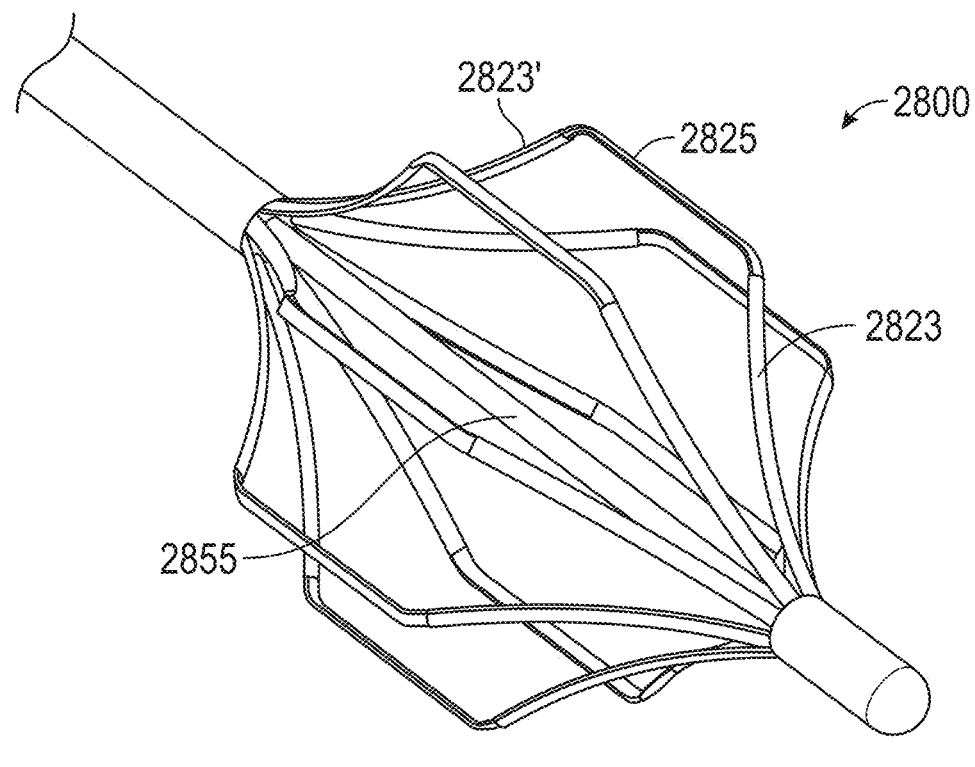
FIG. 28A illustrates an example of an apparatus for delivering pulsed electrical energy within a lumen.
Figure 28B:
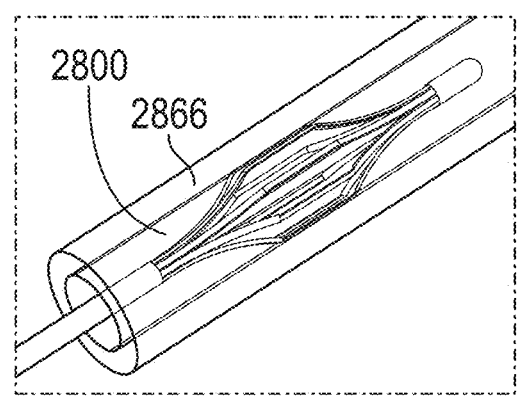
FIGS. 28B and 28C show the apparatus of FIG. 28A within a narrow (FIG. 28B) and larger (FIG. 28C) diameter lumen.
Figure 28C:
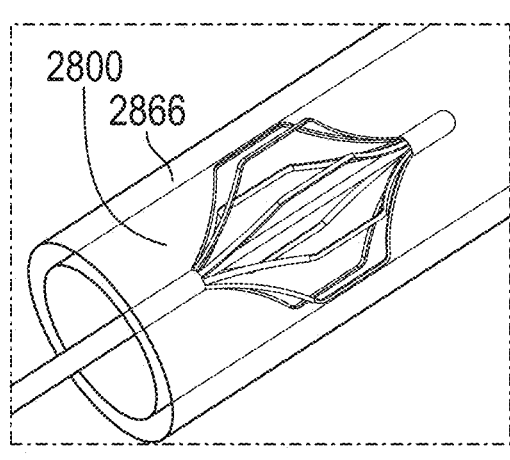

For example, FIGS. 28A-28C illustrate an example in which the ribs forming the expandable frame of the applicator region may be shaped to be substantially parallel with the long axis of the midline of the applicator region, so that they appear substantially "flat" and may align with the walls of the lumen when expanded radially outwards. In FIG. 28A, the apparatus 2800 is similar to that shown in FIGS. 22A-22C and FIGS. 23A-23F in including multiple ribs (splines) 2821 that are radially arranged around a central midline

2855. Each rib includes an active (electrode) region 2825 that is flanked by an insulated region 2823, 2823'. In this example eight ribs are arranged radially around the midline. The central midline may be formed of an inner elongate member that is coupled to the distal end region of the ribs and may be slid distally or proximally to expand/contract the applicator region.

In FIG. 28A, each of the ribs is shaped so that the active region 2825 extends substantially flat (unbent) to expose approximately the same size active region (electrode) regardless of the amount of expansion of the applicator region (e.g., the frame). For example, in FIG. 28B the lumen is narrower than the lumen shown in FIG. 28C, and the applicator region may expand less than in FIG. 28C to contact the wall of the lumen. As the applicator region expands outwards, the active region of the ribs remains substantially parallel with the central midline and also substantially parallel with the wall of the lumen 2866, as shown in FIGS. 28B and 28C. Further, the length of the active regions in contact with the tissue are substantially similar.

Thus, in some examples the ribs may be shape set or formed to assure that regardless of the ID of the lumen, including an organ such as the bronchi, esophagus, blood vessel, etc., and the length of the contact between the exposed active (electrode) section of each rib and the tissue does not change significantly. For example, the apparatus 2800 may be introduced inside the lumen (organ) with an ID of approximately 20 mm (e.g., FIG. 28C); the same apparatus may be used within a lumen having an ID of approximately 10 mm (e.g., FIG. 28B). In the apparatus shown in FIG. 28A, the ribs may be formed of a shape memory alloy (such as Nitinol) and may have an active (exposed electrode) region of length approximately 10 mm, for example. In general, the length of the exposed section can vary depending on application.

In any of these apparatuses the ribs may be hinged to include a more flexible region to allow preferential bending on either side of the active region, similar to the configuration shown in FIG. 28A. The hinge may be a living hinge. In some examples, the hinge is formed by a narrowing or cut-out region on one or both sides of the rib. The hinges may act as stress concentrators to allow a contact bend along the exposed, un-insulated, active region of the rib.

Figure 29A:
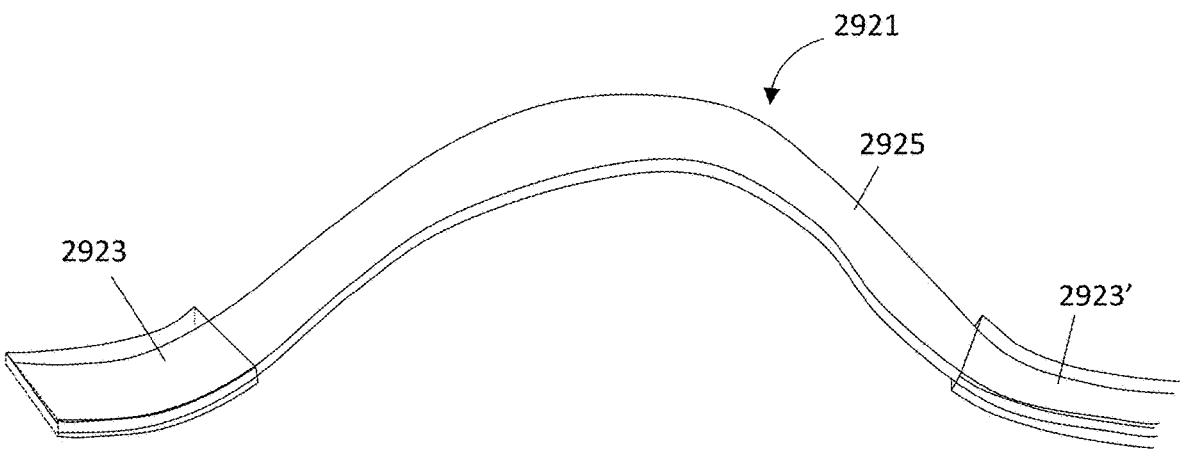
FIG. 29A shows an example of a rib of an applicator region bending with a curve.
Figure 29B:
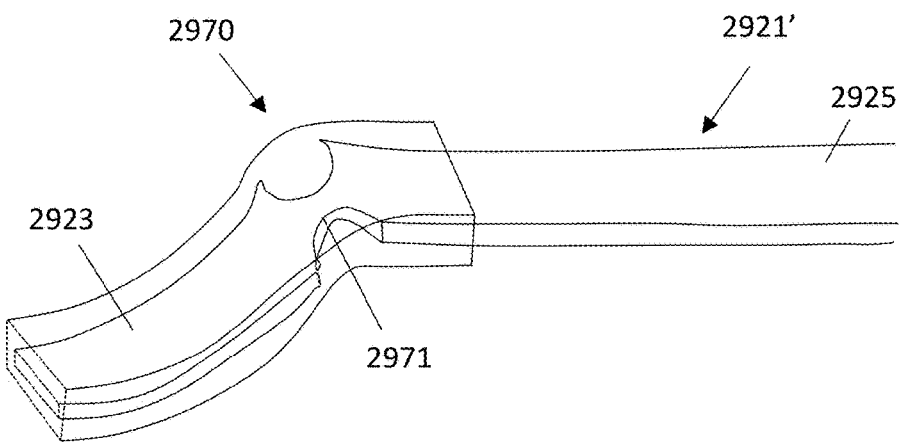
FIG. 29B shows an example of a rib of an applicator region that is hinged as described herein.

FIG. 29A illustrates an example of a rib that does not include one or more hinges. In this example, the rib 2921 includes an un-insulated, active region (electrode) 2925 that is flanked by a pair of insulated regions 2923, 2923'. The rib extends in an arc. FIG. 29B shows a similar rib in which a hinge region 2970 is included. The hinge region in this example is formed by two cut-out regions 2971 that provide preferential bending at the hinge region. In some examples the hinge region may be formed by a thinning of the thickness of the rib at the hinge region, perforations at the hinge region, a shape-set bend at the hinge region, and/or the use of one or more different materials at the hinge region, such as regions that more preferentially bend than the active region. A second hinge region may be included at the opposite side of the active region 2925 (not shown). In any of these examples the hinge region may be within the insulated region 2923, within the un-insulated region 2925, or spanning the two regions. In FIG. 29B the hinge region is within the insulated region 2923. The insulation material may provide support for the hinge region, preventing breaking of the rib at the hinge region.

Figure 30A:
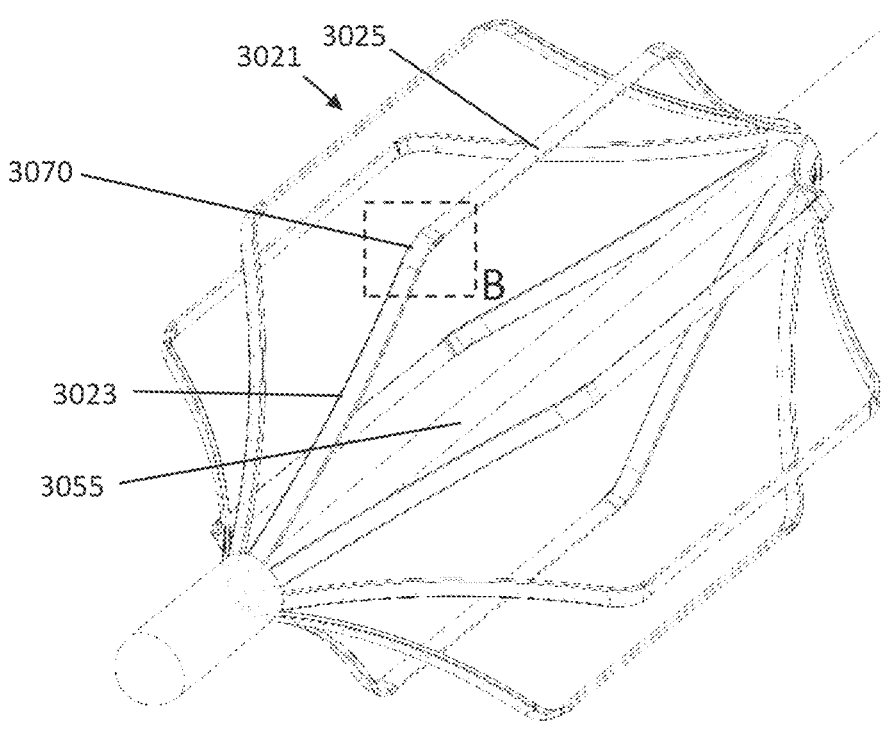
FIG. 30A shows an apparatus for delivering pulsed electrical energy within a body vessel (lumen).
Figure 30B:
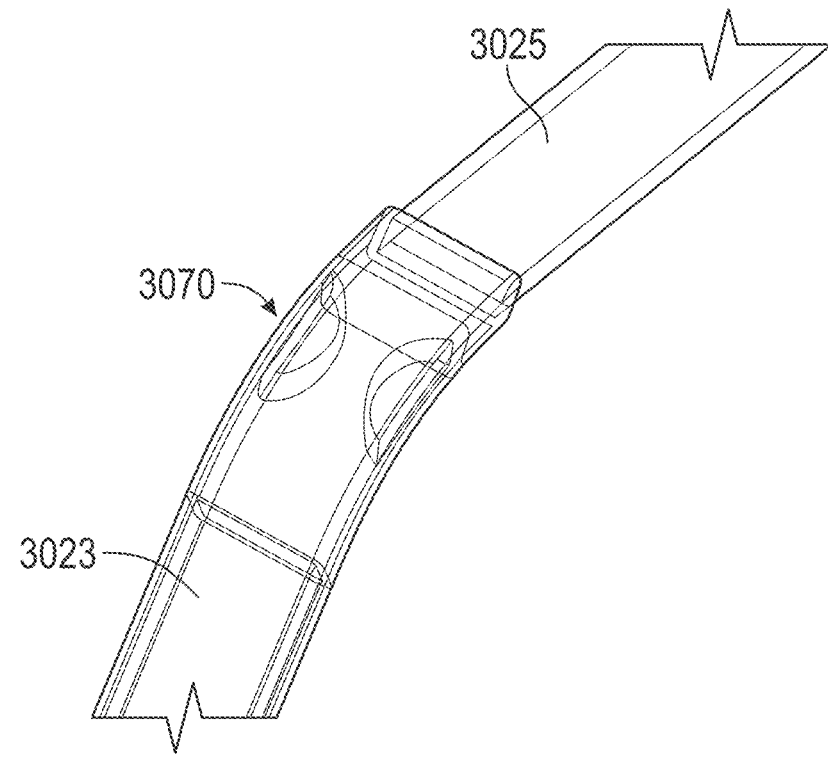
FIG. 30B shows an enlarged view of a hinge region of the apparatus of FIG. 30A.

FIGS. 30A and 30B illustrate another example of an apparatus including an applicator region comprising a plurality of ribs 3021 that are each configured to have an active region 3025 (electrode) that is configured to remain substantially flat and parallel to the central longitudinal axis of the applicator region 3055 in any expanded configuration. FIG. 30B shows an enlarged view of section B of FIG. 30A, showing the hinge region 3070 of one of the ribs. In this example the hinge region is similar to that shown in FIG. 29B and is covered by the electrically insulating material of the insulated region 3023.

As mentioned above, any of these apparatuses may also or alternatively include a balloon to help expand the applicator region. For example, a balloon may be positioned within the expandable frame formed by the applicator region, as shown in FIG. 31. In this example, the apparatus 3100 includes a balloon 3185 that is shown inflated within the applicator region formed by eight ribs and may drive (or may assist in driving) expansion of the applicator region. The balloon may be inflated by injection of a fluid, such as saline, into the balloon through the elongate body 3103. Each rib includes an active region 3125, shown in this example as a centrally located active region (electrode) that is flanked by a pair of insulated regions 3123, 3123'. In some examples the applicator region may be shape-set to collapse, so that deflation of the balloon may allow the ribs to self-collapse back to the un-expanded configuration. In some examples the applicator region may also be collapsed by pulling it proximally back into a catheter or sleeve. An applicator region may also include one or more elongate members to assist in expansion/collapse in addition to a balloon, as described above. A balloon such as the one shown in FIG. 31 may also act as an insulator to prevent arcing between the electrodes of different polarities. For example, the balloon may be formed of an electrically insulating material. The apparatus shown in FIG. 31 also includes an atraumatic distal tip 3186, which may additionally or alternatively be used as a centering guide in some examples.

Point-by-Point Treatment

The apparatuses described herein may be used for point-by-point treatment, as mentioned above. For example, any of these apparatuses may include a smaller electrode, e.g., in reference to FIG. 3A or 3B (showing a center electrode), or a sub-section of an applicator region, as described in reference to FIGS. 3B and 7. In some examples, such as the apparatus shown in FIGS. 22A-22C, a single pair of ribs of different polarity may be used to apply treatment to a smaller region of tissue. Thus, sub-sections or subregions of a larger set of circumferential electrodes may be used. For example, the apparatuses described herein may be used for performing cardiac ablations to address the variety of issues, e.g. atrial fibrillation, ventricular tachycardia, thickening of the ventricular wall, etc., as well as ablations in other organs, e.g. esophagus (e.g., Barret's esophagus), bronchi (e.g., chronic bronchitis, asthma, etc.), or the like. The same apparatuses may be configured to apply both larger regions of treatment, e.g., using an entire applicator region, and may apply a smaller region of treatment, appropriate for point-by-point treatment, using a sub-section of the applicator region.

The apparatuses described herein may be configured to create treatment regions (e.g., in some examples, regions of ablation) of about 5-15 mm. Larger treatment regions may not be necessary or recommended in some cases. For example, ablating too much of the proximal wall or roof of the heart's left atrium (LA) may lead to loss of cardiac muscle functionality or to the interruption of the proper pathways for the propagation of the heart's electric impulses. The apparatuses described herein may limit the "footprint" of ablation to, e.g., about 5-15 mm depending on the distance between electrodes, and may create an electric field that is strong enough to achieve transmural effect.

FIGS. 32 and 33 illustrate another example of an apparatus for an applicator in which the applicator region includes a distal ring 3214 having three independently addressable electrodes 3214', 3214", 3214'" and a proximal ring 3212 of three independently addressable electrodes 3212', 3212", 3212'". Therapeutic energy may be applied between the entire distal ring and the proximal ring, e.g., to circumferentially treat (e.g., ablate) a lumen, or energy may be applied between just a subset of the distal ring electrode and the proximal ring electrodes (e.g., just between 3214' and 3212'). Treatment may therefore be applied just when the side of the applicator region is facing the tissue.

FIGS. 34A-34C, 35 and 36A-36D illustrate examples of applicators that may be configured as described herein. FIGS. 34A-34C show examples of flat "paddle" applicators that include an outer electrode (wire electrode) and an inner electrode (wire electrode). For example, FIG. 34A shows an example of a substantially flat paddle applicator including an outer (more distal) active region electrode 3401 and an inner (more proximal) active region electrode 3403. The outer and inner electrodes are arranged so that the minimum distance, d, between the outer and inner wire electrodes is substantially the same along their lengths. Each electrode is formed by a wire that is insulated 3405 proximally but is un-insulated over the active region. Similarly, the wire paddle-shaped apparatus in FIG. 34B also includes an outer (more distal) active region electrode 3401' and an inner (more proximal) active region electrode 3403'. The outer and inner electrodes are arranged so that the minimum distance, d', between the outer and inner wire electrodes is substantially the same along their lengths. FIG. 34C illustrates another example of a wire paddle-shaped apparatus that also includes an outer (more distal) active region electrode 3401" and an inner (more proximal) active region electrode 3403". The outer and inner electrodes are arranged so that the minimum distance, d", between the outer and inner wire electrodes is substantially the same along their lengths. In FIG. 34C the overall shape is a semi-circular shape.

FIG. 35 is another example of a paddle type applicator formed by two parallel wires that are arranged longitudinally. The elongate body and/or the insulated portion of the wires 3505 forming the electrodes may be L-shaped so that the electrodes may be placed flat against a target tissue without contacting the elongate body to the tissue. In FIG. 35, the first wire 3503 is separated from the second wire 3501 by a fixed distance along the active (un-insulated) length of the electrode.

FIGS. 36A-36D show examples of applicators having forward (distal) facing electrodes. FIG. 36A includes a plurality (e.g., in this example, six) ribs that each include a distal-facing electrode 3603. The active region (electrode) is formed in this example from an un-insulated portion of each rib (spline), and each of these active regions may be electrically coupled together to form a single polarity electrode. A central electrode 3605 is positioned on the distal end face of the electrode. As in the apparatuses shown in FIGS. 22A-22C and 23A-23F above, the apparatus shown in FIG. 36A may be expandable and collapsible, including by coupling he distal end of each rib to an axially slidable elongate member that may slide relative to the proximal end of the ribs.

FIG. 36B shows an example of an apparatus configured as a distal-facing applicator including a pair of wings 3613, 3615 that may be energized at different polarities to apply energy therebetween. The example of the applicator shown in FIG. 36C is similar to that shown in FIG. 36B, and also include a pair of wings 3613', 3615' that may be energized at different polarities to apply energy therebetween. The electrodes in this example maintain a constant distance between them over their length, which may be beneficial in applying a uniform energy density to the tissue.

FIG. 36D illustrates an example of an apparatus having radially separated active regions (electrodes) 3661, 3662, 3663, 3664 that form a distal-facing circle. The first 3661 and third 3663 active regions, which are separated by the second 3662 and fourth 3664 active regions may be a first polarity (and may be electrical coupled to each other), while the second 3662 and fourth 3664 active regions may be a second polarity and may be electrically coupled to each other. In some examples only two of the four electrodes may be used, with each electrode applying opposite polarity energy, for example the first and second active regions.

FIG. 36E illustrates an example of an apparatus (e.g., applicator) having three radially separated active regions 3677, 3677', 3677" (and in some examples, a central electrode). These active regions may be formed of a flexible wire that is exposed (uninsulated) along all or a portion of the circumferentially-extending length forming the "petal" shape. Applicator may be any appropriate size; for example, the length of the active region of each petal may be between 5 mm and 3 cm (e.g., between 7 mm and 1.5 cm, between 8 mm and 12 mm, etc.) and the diameter of the (optional) central electrode may be between 0.5 mm and 5 mm (e.g., between 1 mm and 3 mm, etc.). Each of the curved active regions ("petals") in this example may extend approximately 120 degrees around a central region that includes an optional central electrode. In some examples the central electrode, if present, may be configured to operate at a different polarity than one or more (or all) of the radial, curving active regions, to apply energy in a bi-polar manner (between the central electrode and one or more of the active regions). In some examples a central electrode is not included or is not used, and bi-polar energy may be applied between any two of the curved active regions.

Any of these apparatuses may be used as a distal part of a device or an apparatus including an elongate body (e.g., catheter) that may be used for treatment within a lumen of the body, such as (but not limited to) treatment of atrial fibrillation, ventricular tachycardia, or other cardiac related ablations. For example, these apparatuses may be used to apply nanosecond pulsed electrical field in virtually any part of the human body. For example, these apparatuses may be used in some implementations to apply other types of energy, e.g. RF or microsecond pulsed energy. These applicators can be a part of the catheter used during a minimally invasive procedures or as a part of an apparatus used during surgery, e.g. cardiac surgery. In some cases the method of using the apparatus may be performed as a concomitant procedure if necessary and the device may not be catheter-based.

In any of these apparatuses, the distance between electrodes can vary, which may determine the strength of the pulsed field at every given voltage, hence the size of the treatment region.

Centering Features

Any of the apparatuses described herein may also include a centering guide (centering feature) to assist in positioning the apparatus within the tissue. Thus any of these apparatuses may include a centering guide to assist in positioning the apparatus so that the electrodes (e.g., of a single shot configuration) are oriented relative to the tissue. In some examples the apparatus may include a centering guide to position the electrodes of the apparatus relative to the antrum/ostium regions of various vessels, such as the heart's pulmonary veins enabling proper positioning and more efficient ablation while achieving PVI (Pulmonary Vein Isolation).

Figure 37:
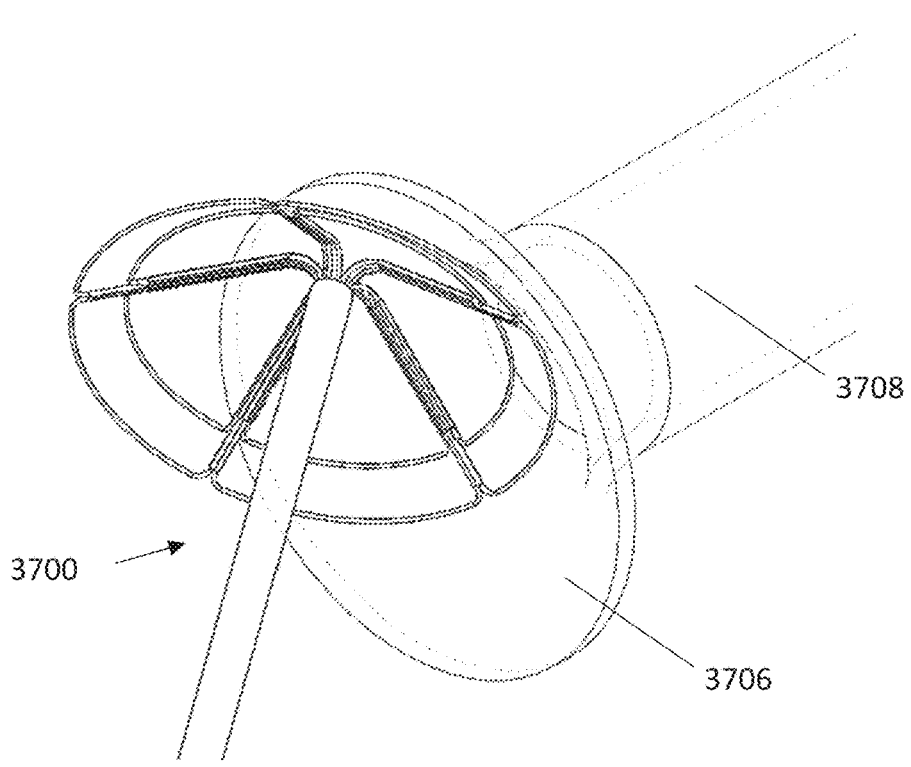
FIG. 37 illustrates the difficulty in positioning an apparatus to treat a pulmonary vein.

FIG. 37 illustrates the difficulty in centering an apparatus 3700 such as the apparatuses including an applicator described herein relative to the target tissue; in this example the target tissue is the left atrium (LA) 3706 of pulmonary veins (PVs) 3708. Positioning the apparatus relative to the LAPVs can be challenging particularly if 3D visualization is not performed. Many facilities conducting procedures to address atrial fibrillation (AFIB) do not have 3D mapping capabilities and rely on fluoroscopic imaging to place their devices. Thus, navigating the apparatus towards the PV can be difficult. In certain cases the device may be placed off-centered to the antrum of the PV as shown in FIG. 37, preventing circumferential ablation from being achieved.

Figure 38A:
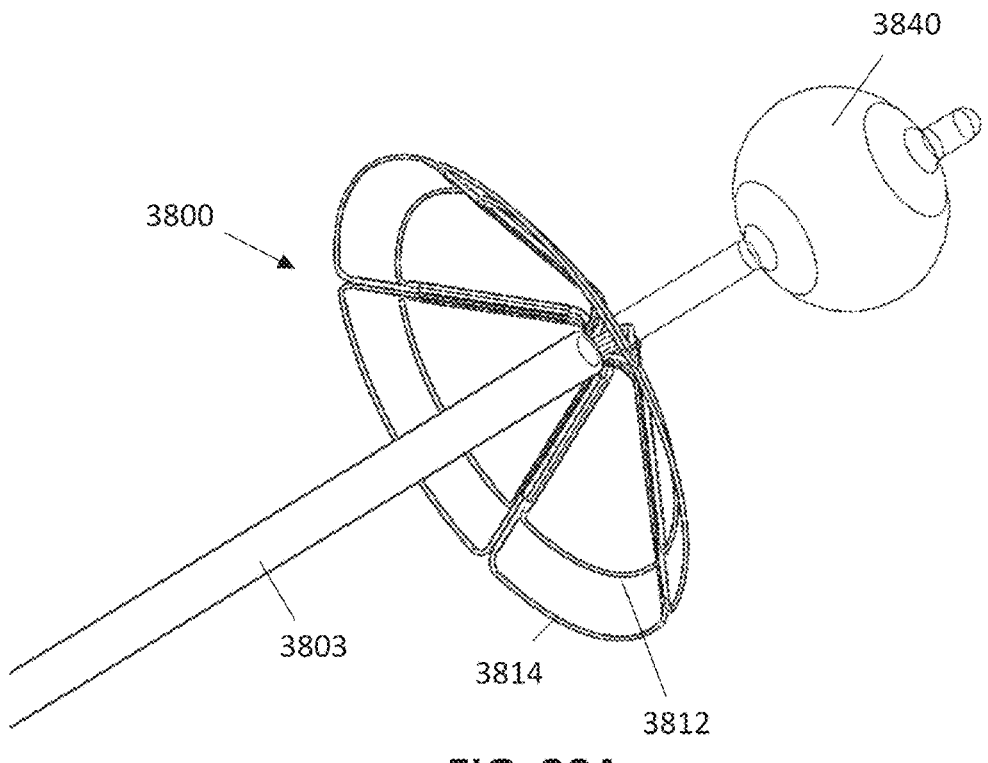
FIG. 38A-38B show apparatuses for delivering pulsed electrical energy within a lumen including centering guides.

Thus, any of the apparatuses described herein may include one or more additional centering guides that can be a part of the apparatus or an additional device that can be used in conjunction with the apparatus to enable the centering with regard to the lumen into which the treatment is to be applied, such as (but not limited to) an antrum of the PVs. In general, the centering guide may be an expandable, atraumatic projection that may extend distally of the distal end of the apparatus. FIG. 38A illustrates one example of an apparatus 3800 including an applicator as described herein including a centering guide 3840. The centering guide feature 3840 is integrated into the apparatus in this example and extends distally beyond the electrodes of the first (outer) ring 3814 and the second (inner) ring 3812.

Figure 38B:
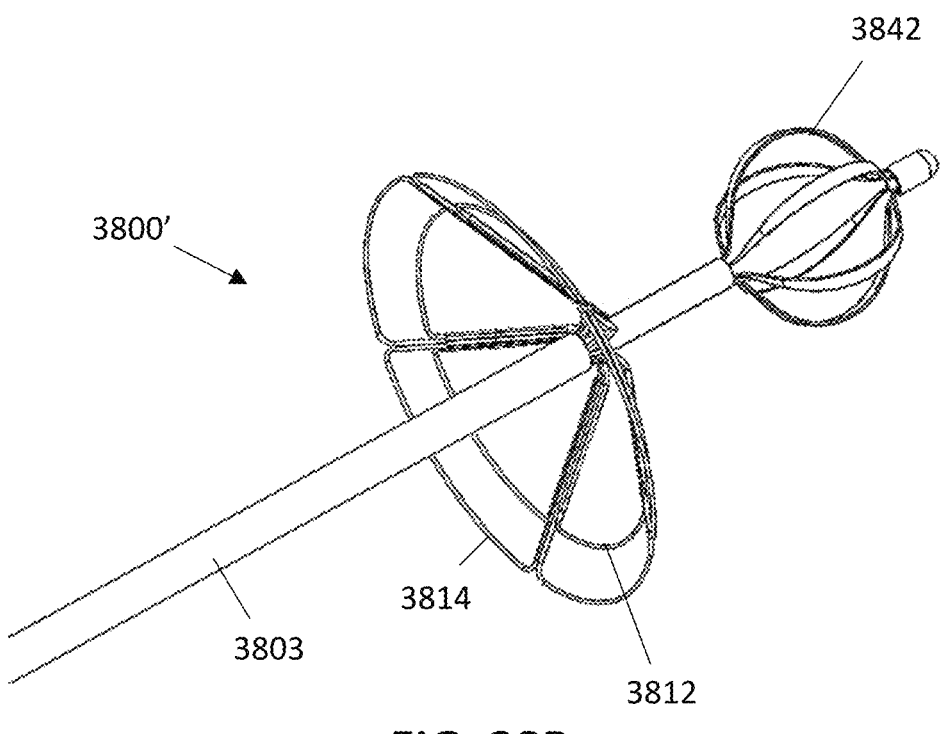
Figure 39:
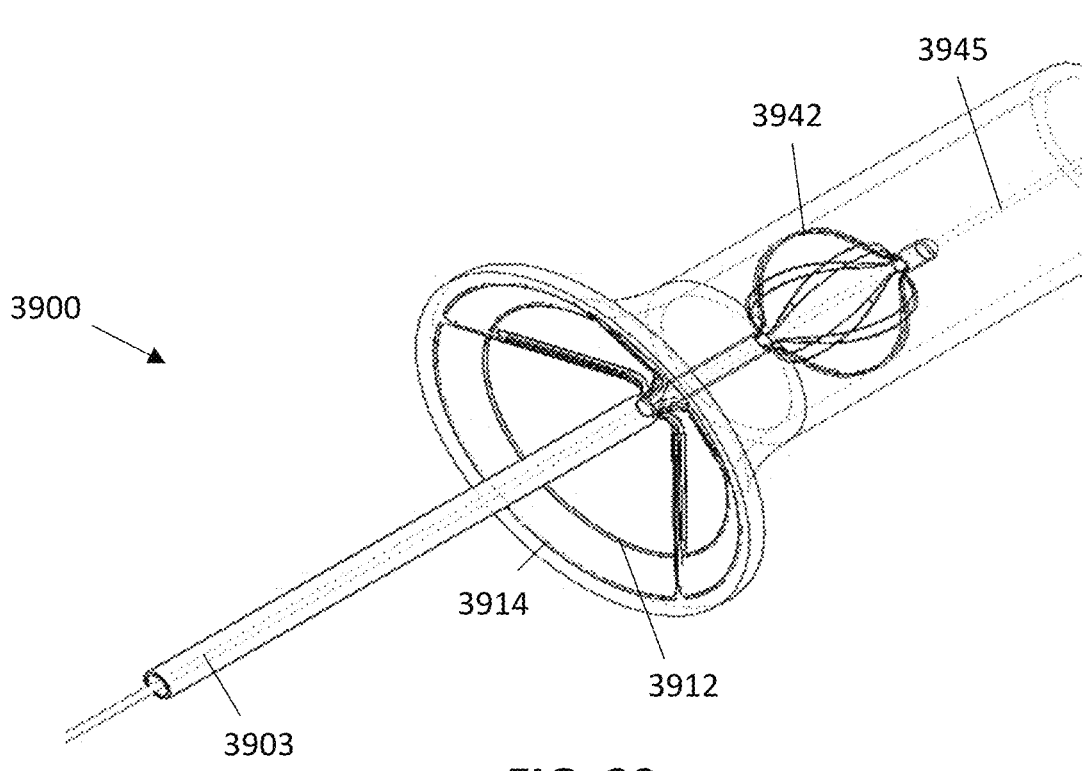
FIG. 39 is an example of an apparatus for delivering pulsed electrical energy within a lumen including a centering guide.

FIG. 38B shows an apparatus including another example of a centering guide 3842 extending from the distal end of the apparatus 3800', distal to the first 3814 and second 3812 rings forming the active regions (electrodes) extending from an elongate body 3803. In FIG. 38A the centering guide is an expandable and collapsible balloon, while in FIG. 38B the centering guide is formed by a plurality of splines that may expand and collapse. The centering guide may generally be positioned within the lumen first and expanded to guide positioning within the tissue traumatically. Any of these apparatuses may also or additionally use a guidewire for positioning the apparatus. For example, a balloon or splines may have integrated guidewire or a lumen for a guidewire that can be used to introduce the apparatus. For example, a balloon or splines (centering guide) can be integrated into the ablation device and introduced over a guidewire together. FIG. 39 illustrates one example of an apparatus 3900 including pair of ring electrodes 3912, 3914, a centering guide 3942 and a guidewire 3945. The guidewire extends through a lumen in the elongate body 3903.

In some examples the centering guide may also act as, or may include, an electrode for the application of pulsed energy to the tissue. For example, in FIG. 39, the basket 3942 (formed of splines/ribs) may include an electrode that may be used at a first polarity when one or both of the ring electrodes 3912, 3914 are used at a second polarity, to apply treatment to the tissue, such as by applying sub-microsecond (e.g., nanosecond) pulses between the ring electrode(s) and the basket.

Figures 40A, 40B, 40C, 40D, 41A, 41B, 41C, 41D:
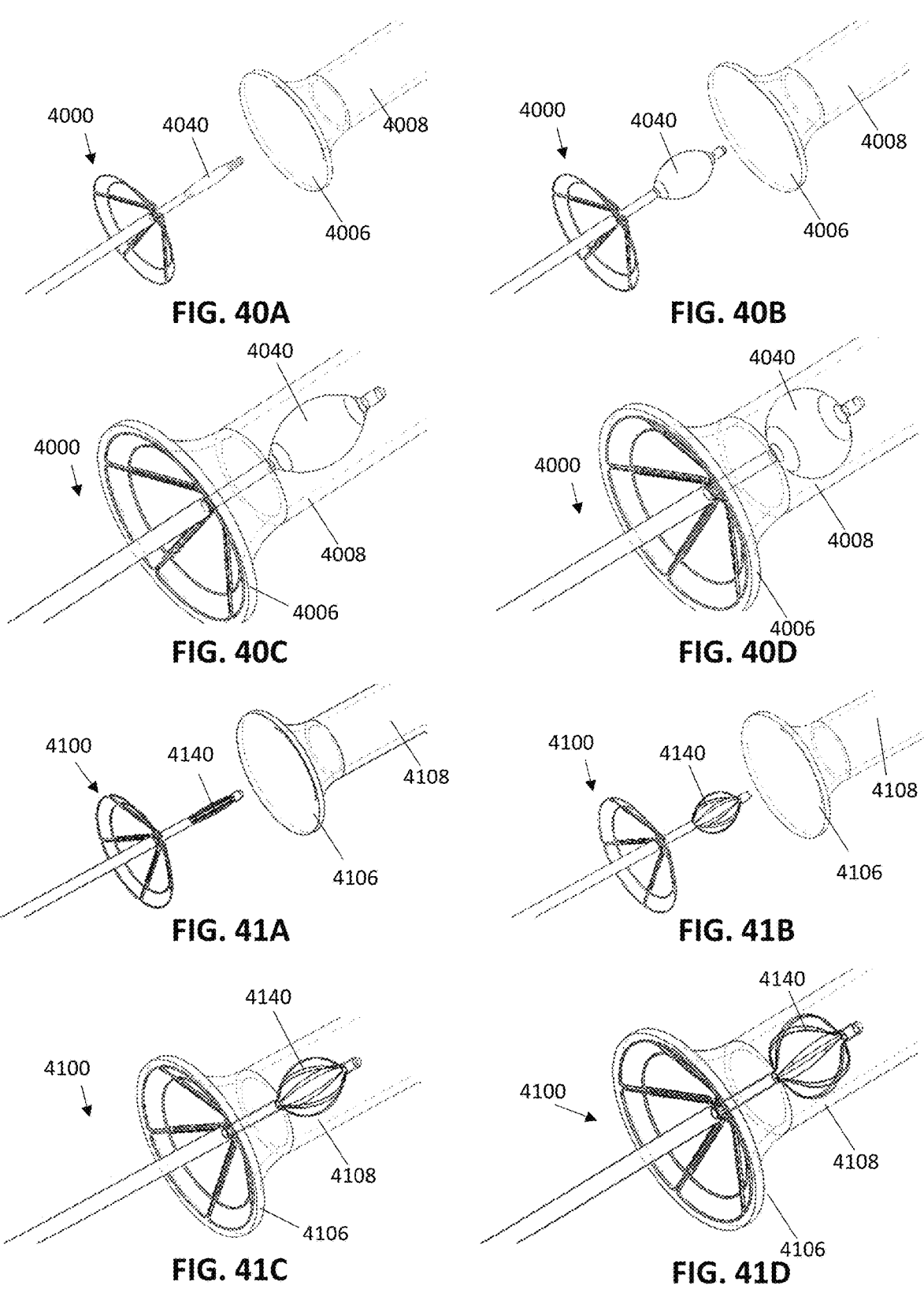
FIGS. 40A-40D illustrate a method of using an apparatus for delivering pulsed electrical energy within a lumen using a centering guide.
FIGS. 41A-41D illustrate a method of using an apparatus for delivering pulsed electrical energy within a lumen using a centering guide.

For example, FIGS. 40A-40D illustrate use of a centering guide configured as an expandable balloon as part of an apparatus. In FIG. 40A the apparatus 4000 including a deflated balloon 4040 is introduced near an LA 4006 and positioned. The centering guide (e.g., balloon) 4040 is partially inflated, as shown in FIG. 40B, to have an OD that is smaller than the ID of the PV 4008. In FIG. 40C the centering guide (balloon) is moved inside the PV until the ring electrodes contact the antrum, as shown. Finally, as shown in FIG. 40D, the balloon is inflated.

FIGS. 41A-41D illustrates a similar method of use when the centering guide is an expandable basked, e.g., formed by splines (ribs) as shown in FIG. 38B. In FIG. 41A the apparatus 4100 including a collapsed basket 4140 is introduced near an LA 4106 and positioned. The centering guide (e.g., basket) 4140 is partially expanded, as shown in FIG. 41B, to have an OD that is smaller than the ID of the PV 4108. In FIG. 41C the centering guide (basket) is moved inside the PV until the ring electrodes contact the antrum, as shown. Finally, as shown in FIG. 41D, the balloon is inflated.

Methods to Treat Cardiac Ablations

In general, the methods and apparatuses described herein may use pulsed electrical energy (e.g., microsecond, sub-microsecond, nanosecond, etc., pulsed electrical energy) to treat atrial fibrillation, ventricular tachycardia, and other cardiac related ablations. The applicators described herein may be used to deliver pulsed electrical energy to desired treatment areas during minimally invasive procedures or during surgery, such as during cardiac surgery.

For example, these methods and apparatuses may be used to tread cardiac ablations by delivering pulsed energy to coronary arteries as well as peripheral arteries and veins. For example, any of the applicators described herein may be used to deliver pulsed energy to the antrum of the pulmonary vein. In particular, the applicators may conform to a transitional region of the antrum that begins (with respect to the distal region of the applicator) with a relatively larger region and transitions to a relatively smaller region. A first or distal electrode having a relatively smaller diameter may contact the smaller region while a second or proximal electrode having a relatively larger diameter may contact the larger region.

In another example, diameter dimensions of the first and second electrode may be reversed such that the diameter of the first electrode is relatively larger than the diameter of the second electrode. The use of such applicators may be well suited for treating regions of tissue that begins with a relatively smaller region and transitions to a relatively larger region.

One example usage of the applicators described herein is to deliver a single-shot ablation for pulmonary vein isolation in the left atrium to treat atrial fibrillation. To gain access to the left atrium, a puncture of the femoral vein may be performed using a needle under fluoroscopic and/or ultrasound guidance. After the puncture, under fluoroscopic guidance a 0.032-inch J-tip guidewire may be advanced. The needle may be removed, and a sheath introducer (usually 8-12 F in size) may be inserted into the vein and then flushed. A transseptal sheath (which may carry any of the applicators described herein) is advanced over the guidewire to the superior vena cava (SVC). Alternatively, the apparatuses of the present disclosure may be advanced through the inferior vena cava (IVC) in the case of a primary puncture being done in the femoral vein.

Once the sheath is positioned within three to four centimeters (cm) superior to the cavoatrial junction, the wire is removed. The transseptal puncture needle is advanced under fluoroscopic guidance until it reaches the sheath tip. The needle is advanced with the stylet inserted until it reaches 4 cm from the tip. The stylet prevents the needle tip from scraping the inner lumen of the sheath. The stylet can then be removed. Puncture is performed and sheath is advanced into the left atrium. The catheter with the electrodes may be introduced in the left atrium through the sheath.

The electrodes may be pushed against a wall of the left atrium, in particular surrounding the pulmonary vein. The proper positioning of the electrodes can be aided by the deflectable or fully articulated distal end of the elongate catheter body, controlled via mechanism in the elongate handle and pull-wires located within the shaft of the elongate catheter body. The proper location of the catheter can be verified using fluoroscopy and/or ultrasound (TEE and/or ICE), as well as impedance and/or magnetic localization enabled by additional electrodes and/or magnetic sensor(s) of the catheter. The proper contact between electrodes of the applicator and left atrium wall can be verified via impedance readings enabled by sending, for example, low amplitude non-therapeutic electrical "test" signals. After the proper position and contact of the electrode bipolar couples is confirmed, the energy (nanosecond pulse, microsecond pulse, RF) can be applied to achieve the desired ablative effect. By means of subsequent repositioning of the catheter and the distal bipolar couple and repeating the energy application over additional left atrial areas surrounding other pulmonary vein(s), a complete pulmonary vein isolation treatment can be achieved.

Pulsed electrical (e.g., nanosecond pulsed) treatment may include a pulse profile having a rise and/or fall time for pulses that may be less than 20 ns, about 20 ns, about 25 ns, about 30 ns, about 40 ns, about 50 ns, about 60 ns, about 75 ns, or greater than 75 ns. In some examples, the pulse voltage may be less than 1 kV, less than 5 kV, about 5 kV, between about 5 kV and about 10 kV, about 15 kV, about 20 kV, about 25 kV, about 30 kV, greater than 5 kV, greater than 10 kV, greater than 15 kV, greater than 20 kV, greater than 30 kV, etc. In some examples, the current may be less than 10 A, about 10 A, about 25 A, about 40 A, about 50 A, about 60 A, about 75 A, about 100 A, about 125 A, about 150 A, about 175 A, about 200 A, or more than 200 A. In some examples, the pulse duration may be less than 10 ns, about 10 ns, about 15 ns or less, about 20 ns or less, about 25 ns or less, about 30 ns or less, about 40 ns or less, about 50 ns or less, about 60 ns or less, about 75 ns or less, about 100 ns or less, about 125 ns or less, about 150 ns or less, about 175 ns or less, about 200 ns or less, about 300 ns or less, about 400 ns or less, about 500 ns or less, about 750 ns or less, about 1 µs or less, about 2 µs or less, about 3 µs or less, about 4 µs or less, about 5 µs or less, or greater than 5 µs. The apparatuses (e.g., systems) described herein may include, in addition to the instrument (e.g., the elongate applicator tool), a pulse generator such as the one shown schematically in FIG. 1, configured to emit pulses, e.g., in the sub-microsecond range.

In general, the systems of the present disclosure may comprise additional elements, such as power supplies, and/or a high voltage connector for safely connecting the elongate applicator tool device to a high voltage power source. As described above, these systems and devices are configured to apply high voltage, sub-microsecond pulsed electrical energy.

Figure 42:
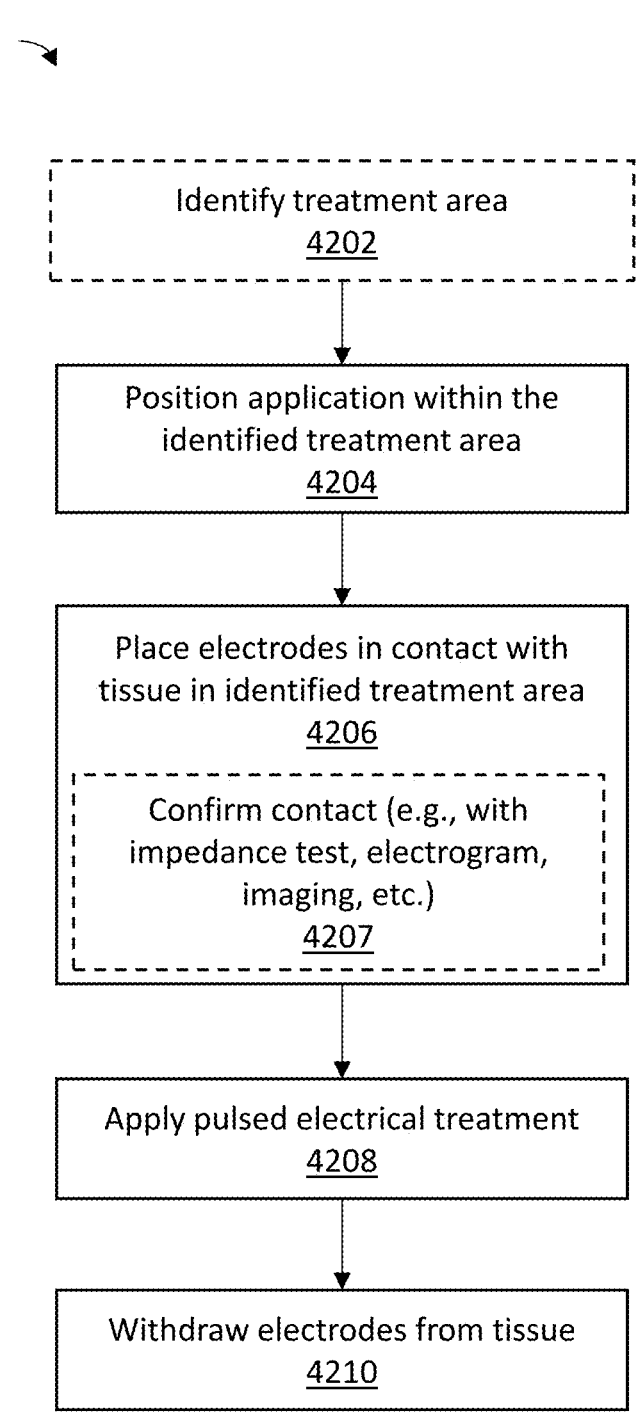
FIG. 42 is a flowchart depicting an example of one method for delivering pulsed electrical treatment to a selected treatment area of a patient.

FIG. 42 is a flowchart depicting an example of one method 4200 for delivering pulsed electrical treatment to a selected treatment area of a patient. Some examples may perform the operations described herein with additional operations, fewer operations, operations in a different order, operations in parallel, and some operations differently. The method 4200 may be used to treat atrial fibrillation, ventricular tachycardia, or other cardiac ablations. The method 4200 is not limited to cardiac applications, but rather may be also used to treat various body vessels.

In FIG. 42, the method 4200 may begin as a treatment area is identified in the block 4202. Block 4202 may be optional as denoted with dashed lines in FIG. 42. For example, one or more diagnostic tests for a patient may identify a region of a vein, artery, or other body vessel to receive pulsed electrical treatment. In other examples, the treatment area may be any technically feasible lumen, passage or structure. The diagnostic tests may include radiological, vascular, ultrasound, or any other feasible tests that enable the identification of a treatment area.

In block 4204 an applicator is positioned within the identified treatment area. For example, the system 100 of FIG. 1 may be used to position an applicator (such as, but not limited to, any of the applicators of FIGS. 2-41D) within the identified treatment area. For example, the applicator may be positioned by expanding a first electrode (e.g., a first ring electrode having one or more loops) and a second electrode (e.g., a second ring electrode having one or more loops) that are spaced apart.

In block 4206, electrodes of the applicator may be placed in contact with a target tissue in the identified treatment area. The electrodes may be positioned so that an active region on the first electrode, which may extend circumferentially (fully or partially) on the targe tissue, is spaced apart from an active region on a second electrode that may also extend circumferentially (fully or partially) on the target tissue. The region between the first electrode and the second electrode active regions may be treated. In some examples the first active region of the first electrode and the second active region of the second electrode may be placed circumferentially around a lumen (e.g., vessel wall); in some examples the first active region of the first electrode and the second active region of the second electrode may be placed circumferentially around a portion of a body vessel, such as, in one non-limiting example, an antrum of a pulmonary vein. In some cases, the electrodes may be positioned through an attached elongate catheter body such that electrodes come into contact with the tissue. In some other cases, the electrodes may emerge from an elongate catheter body, and expand to allow the electrodes to enter the treatment area. After expansion, the applicator may be moved to place the electrodes in contact with the tissue.

When placing the electrode in contact with tissue, the spacing (e.g., longitudinal spacing) between the electrodes (e.g., sets of electrodes) on the applicator may be adjusted in some examples. For example, and especially in reference to the applicators described with respect to FIGS. 2, 3, 8, and 9, the spacing between the electrode on the applicator may be adjusted to vary the density of the pulsed electric field or to accommodate varying tissue shapes and topologies.

In optional block 4207, contact with tissue may be confirmed by any appropriate method (e.g., impedance testing, electrogram, imaging, etc.). In this optional step, a low level or low amplitude signal (e.g., a voltage and/or current) may be provided to the electrodes. The system 100 may determine and/or measure the impedance associated with the electrodes based on the signals provided to and returned from the electrodes. Contact with tissue may be confirmed when the impedance is within an expected value.

In block 4208, pulsed electrical treatment is applied to the identified treatment area through the applicator. For example, the system 100 may deliver energy through applicators (e.g., between the active region of the first electrode to the active region of the second electrode). In some examples the energy may be provided by a pulse generator configured to provide electrical pulses having an amplitude of greater than 0.1 kV and a duration of less than 1000 nanoseconds.

Additional treatments, including repeating the application of energy to the tissue through the first and second electrodes, may be made; the effect of each pulsed electrical treatment may be assessed. If the treatment is sufficient, no further treatment may be necessary (for example, as determined by imaging, impedance testing, electrogram, etc.). In some examples it may be advantageous to apply the energy in a circumferential pattern as described herein (see, e.g., FIG. 6B) without having to move the apparatus to get near-complete or complete circumferential treatment.

In block 4210, the electrodes of the applicator are withdrawn from the tissue. In some cases, the catheter may be moved with respect to the surface of the tissue that has received treatment to provide further treatment. The applicator may be moved to another treatment area or may be removed from the patient.

Use with Cardiac Mapping

As described above, any of these apparatuses and methods may be used with cardiac mapping systems. For example, any of these apparatuses and methods may be part of an ablation method for treatment of cardiac regions, including but not limited to the pulmonary veins (or the antrum associated with a pulmonary vein), etc., and may include coordinating position of the energy applying (e.g., the sub-microsecond pulsing energy applying) electrodes of the applicator with mapping, such as 3D electro-anatomical mapping/maps of the relevant tissue.

As mentioned, the apparatus may include one or more sensors, including electrical sensors (e.g., sensing electrodes) and/or imaging sensors, etc. The apparatus may integrate data from these one or more sensors with one or more maps of the tissue to be treated. These electro-anatomical maps may be generated by a separate mapping system, including commercially available mapping systems, or apparatuses described herein may include an integrated mapping system or sub-system into the apparatus. In some examples the sensors are configured as electrodes that may be used as sensors for a mapping (e.g., 3D electro-anatomical mapping) system or sub-system and in combination with one or more patches that may be applied to the patient and connected to the mapping system/sub-system.

Any of the applicators described herein may include additional electrodes to allow visualization of the apparatus in combination with a mapping system.

Figure 43A:
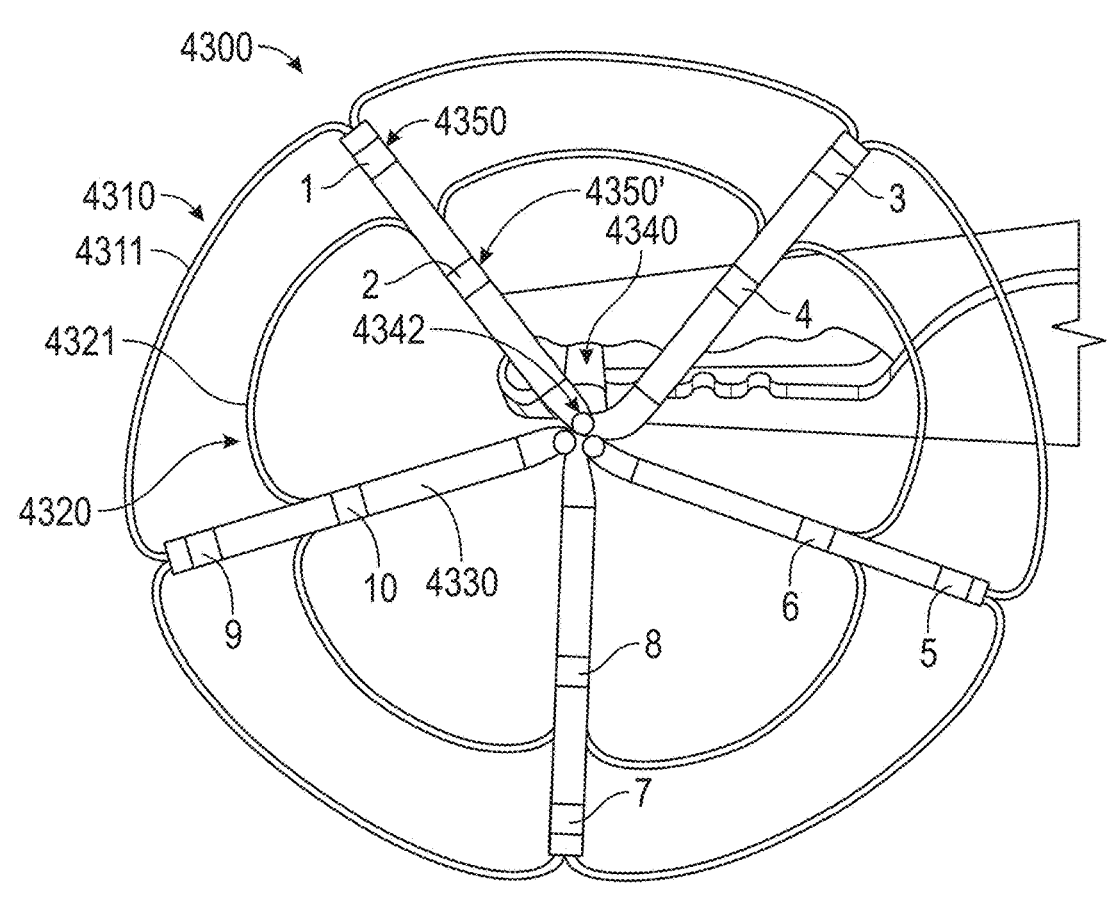
FIGS. 43A-43B illustrate one example of an applicator including treatment electrodes and sensing/mapping sensors.
Figure 43B:
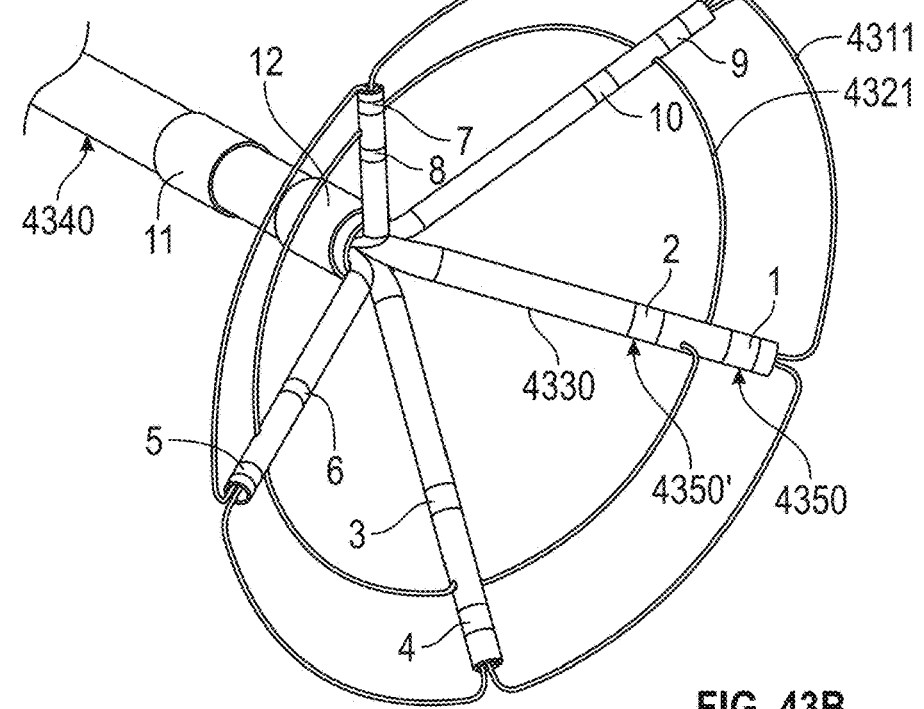

For example, FIGS. 43A-43B illustrate an example of an apparatus similar to that shown in FIGS. 4A-4E and 7, including both treatment electrodes 4311, 4321 and mapping electrodes 4350, 4350'; in FIG. 43A, ten individual mapping electrodes 1, 2, 3, 4, 5, 6, 7, 8, 9, 10 are positioned on the applicator's distal, outward-facing side. The mapping electrodes may also be referred to as sensing electrodes. As described above, the applicator 4300 is configured to deliver nanosecond pulsed energy treatment. The applicator 4300 in this example includes an inner, proximal, ring 4320 and an outer, distal, ring 4310. The inner 4320 and outer 4310 rings each include 5 lobes formed by the lengths of wire forming the treatment electrodes 4311, 4321. In addition, the applicator 4300 includes five arms 4330 that flexibly couple the inner and outer rings to the elongate catheter body 4340. As described above, the inner and outer rings may have more lobes (e.g., more treatment electrodes) and/or may have fewer lobes.

The sensing or mapping electrodes are typically smaller than the treatment electrodes, which are, in this example, elongate lengths of wire. For example, the sensing or mapping electrodes may be 5 mm or less in length and/or width (e.g., may have a maximum dimension of 5 mm or less, 4.5 mm or less, 4 mm or less, 3.5 mm or less, 3 mm or less, 2.5 mm or less, 2 mm or less, 1.5 mm or less, 1 mm or less, etc.). The mapping electrodes may be electrically isolated from the treatment electrodes. In the example shown in FIG. 43A the sensing or mapping electrodes 4350, 4350' are formed of bands or cuffs of electrically conductive material (e.g., metal) that are crimped or otherwise coupled over an insulation material on the arms 4330 of the apparatus. Some examples of the insulating material or coating includes polyimide, PET, etc. Each sensing or mapping electrode may include a lead (e.g., wire) extending from the sensing or mapping electrode, through the catheter and to a coupling site (not shown) for coupling to a sensing or reading subassembly and/or for coupling to a separate mapping system or sub-system. The sensing or mapping electrodes may be electrically separate and isolated from the treatment electrodes.

In operation, the sensing and/or mapping electrodes (e.g., sensing/mapping electrodes) may be used to isolate the position(s) of the applicator relative to the tissue or relative to a map of the tissue. For example, sensing/mapping electrodes 1, 3, 5, 7 and 9 may provide an outline of the outer ring, while sensing/mapping electrodes 2, 4, 6, 8 and 10 may provide an outline of the inner ring. Combination of the sensing/mapping electrodes (e.g., 1-2, 3-4, 5-6, 7-8, 9-10 or other combinations) may be also or alternatively be used to improve the signal acquisition and/or may be used for more reliable tissue contact. In some examples, the sensing/mapping electrodes may be used for position detection without requiring tissue contact.

In general, the sensing/mapping electrodes may be used (instead of or in addition to the treatment electrodes) to monitor the progress of a treatment. For example, the sensing/mapping electrodes may be used to determine if the target tissue has changed one or more electrical properties and/or electrical activity. For example, the sensing/mapping electrodes may be used before and/or between the application of pulsed (e.g., nanosecond pulsed) energy from the treatment electrodes to determine or monitor electrical activity on or adjacent to the target tissue. Ablation of the tissue using the methods described herein, e.g., by the application of non-thermal treatment such as nanosecond pulsed electrical energy may be expected to reduce the electrical activity of the underlying target, e.g., cardiac, tissue. In general, the methods described herein may apply sub-microsecond (e.g., nanosecond) pulsing at, e.g., between 0.1 per second (Hz) to 100,000 Hz. Even at the faster (e.g., kHz) frequencies, the nanosecond pulses may provide relatively long periods in which no energy is being applied to the tissue, during which time the sensing/mapping electrodes may detect electrical activity on the tissue. In some examples the sensing/mapping electrodes may be used to determine impedance of the underlying tissue and/or a change in impedance over time.

The apparatuses described herein may also include one or more magnetic sensors 4342 (e.g., magnetic coils, rods, etc.). In this example, the magnetic sensors are attached to a distal section of the catheter body 4340 and are centrally located relative to the treatment electrodes. This may increase the precision of the location of the catheter.

FIG. 43B shows a side view of the applicator 4300. The inner ring 4320, the outer rings 4310 and the arms 4330 are shown coupled to an elongate body 4340. In this example one or more (e.g., two 11, 12) additional sensing/mapping electrodes may be positioned on the shaft of the elongate body 4340 and may be used in combination with one or more of the other sensing/mapping electrodes mentioned above.

Figure 47A:
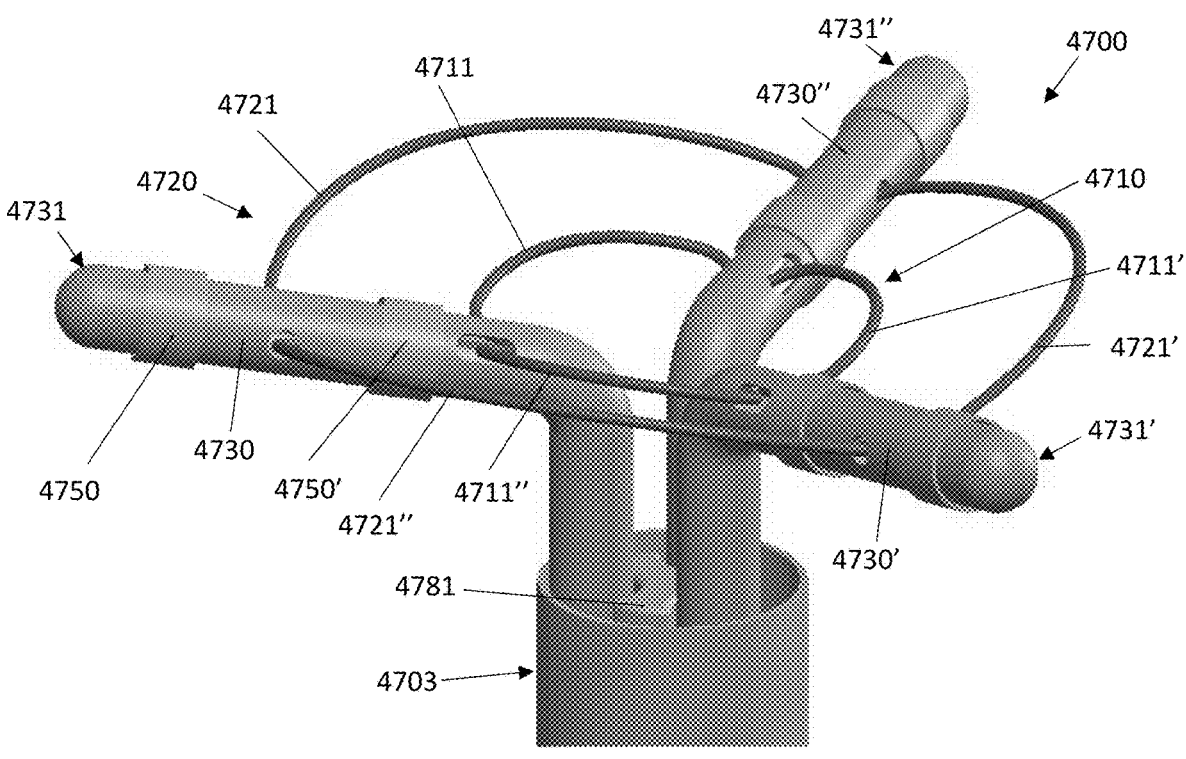
FIGS. 47A-47C illustrate examples of an apparatus for delivering pulsed electric fields.
Figure 47B:
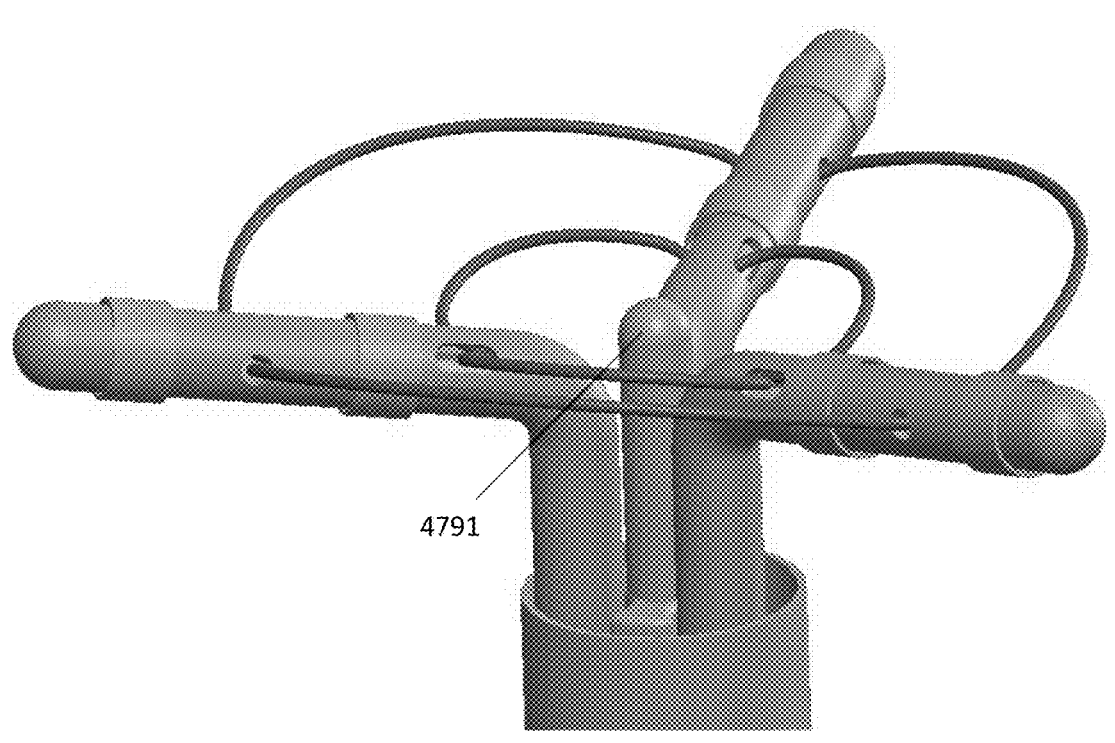
Figure 47C:
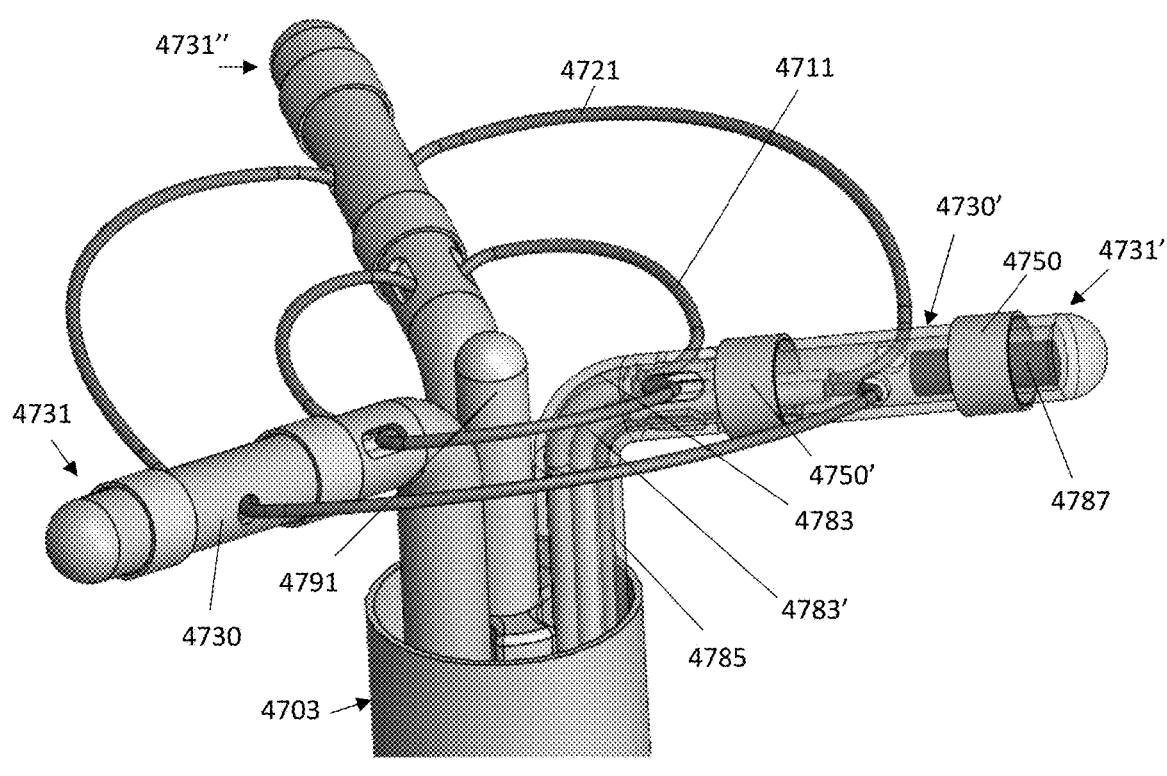

FIGS. 47A-47C show another variation of an apparatus for delivering pulsed electric fields that may include mapping ("sensing") electrodes in addition to the treatment electrodes. In general, the apparatus includes an elongate body 4703, the distal end of which is shown in FIG. 47A. The elongate body may be an elongate catheter body. In some examples the elongate body may be part of an outer delivery catheter. The applicator 4700 may be configured to be held completely or partially within the elongate body in an undeployed state (not shown) that has a low profile to allow it to be easily inserted through the body and expanded by extending out of the elongate catheter body and/or retracting the elongate catheter body. For example, the applicator may include a plurality of arms 4730, 4730', 4730" that are configured to extend from the elongate body at an angle when in the deployed state. The apparatus also includes a first plurality of electrode lengths 4711, 4711', 4711" extending between the plurality of arms and forming a first treatment electrode 4710. The first treatment electrode in some examples is also referred to as "an inner electrode" or "inner ring electrode" (when the applicator is deployed). Each of the first plurality of electrode lengths forms an arc that together form a ring that may be approximately transverse to the long axis of the elongate body in FIG. 47A-47C. The apparatus also includes a second plurality of electrode lengths 4721, 4721', 4721" extending, e.g., in an arc, between the plurality of arms and forming a second treatment electrode 4720 that is radially outward of the first treatment electrode when the applicator is expanded or deployed. In some examples the second treatment electrode is referred to as an "outer electrode" or "outer ring electrode." The apparatus also includes a plurality of mapping and/or sensing electrodes 4750, 4750' on the plurality of arms. The mapping/sensing electrodes may be positioned radially outward of the first treatment electrode (e.g., between the first and second treatment electrodes), as shown. In some examples, the second plurality of electrode lengths may form a ring that may be approximately transverse to the long axis of the elongate body and may be radially inward from the first treatment electrode when the applicator is deployed.

In FIGS. 47A-47B the arm of the applicator of the apparatus may include an extension region 4731, 4731', 4731". The arms of the applicator of the apparatus may be hollow (or solid) cylinders that may be pre-bent or curved and/or biased to bend/curve at an angle to the long axis of the elongate body 4703 when extended relative to the distal opening of the elongate body, as shown in FIGS. 47A-47C. In some examples the arms may house a portion of the electrical lengths forming the treatment electrodes. The plurality of electrode lengths forming the first treatment electrode (and the plurality of electrode lengths forming the second treatment electrode) may each be individually coupled to an electrical connector (e.g., wire, trace, etc.) or may be electrically coupled together. Each electrode of the respective plurality of electrode lengths may be formed as a wire electrode, e.g., as part of a wire electrode that is un-insulated along all or a portion if it's length.

The extension regions of the arms of the apparatus, when deployed, may extend radially outward beyond the outer (e.g., second) treatment electrode, as shown. The extension regions may provide a support or contact, as well as an additional space, for one or more sensing (e.g., mapping)

electrodes. In the example shown in FIGS. 47A-47C, the mapping and/or sensing electrodes are positioned between the first and second treatment electrode rings, on the plurality of arms, as well as on the extension regions of the arms, radially outward from the outer (when deployed) treatment electrode.

The apparatus may also include one or more central electrodes. For example, as shown in FIG. 47B, the apparatus may include a central electrode 4791 that extends distally from out of the elongate body when the applicator is deployed, so that the arms and the first and second electrodes (or, in some implementations, any additional electrodes forming electrode rings similar to the first and second electrodes) encircle the central electrode. The central electrode may be a treatment electrode. In some examples the central electrode may be a mapping/sensing electrode or both a mapping/sensing and a treatment electrode.

FIG. 47C shows an example of the apparatus having features of FIGS. 47A-47B, but with one of the arms 4730' shown as transparent to illustrate one example of the internal components including one or more electrical connectors (e.g., wires) 4783 connected to and/or forming the first electrode length 4711 of the first treatment electrode 4710, one or more electrical connectors (e.g., wires) 4783' connected to and/or forming the second electrode length 4721 of the second treatment electrode 4720, and one or more wires 4785 coupled to the mapping electrode(s) 4750, 4750'. For example, each electrode length of the respective plurality of electrode lengths may be coupled to or may be formed from an exposed, or uninsulated, portion of a wire 4783, 4783'. In general, the arms 4730, 4730' 4730" may be insulated and/or formed of a polymeric material. The arms may include one or more openings out of which the internal wires forming the treatment electrode may pass. The wires within the arms may be configured to slide at least slightly within the arms, so that as the arms convert between a delivery configuration, where they may be held straightened, e.g., within the elongate body 4703, and a deployed state, where the arms are angled relative to the elongate body, the wires may move relatively to each other longitudinally to prevent breaking and release mechanical stress.

In the deployed state the arms may extend at an angle that is, for example, between about 20 degrees and 90 degrees relative to the long axis of the elongate body at the distal end region. In FIGS. 47A-47C the arms (in this embodiment three arms are shown) extend at an angle of about 85 degrees relative to the long axis. In some examples the angle may be between 30 degrees and 90 degrees, between 40 degrees and 90 degrees, between 45 degrees and 90 degrees, etc. In this example all three arms are deployed at approximately the same angle; in some examples the arms may be configured to bend/deploy to different angles, which may 'steer' the face of the applicator in a desired direction. In FIGS. 47A-47C three arms are shown. As mentioned above, in some examples fewer (e.g., two arms) or more than three arms (e.g., four arms, five arms, six arms, etc.) may be used. Any of these apparatuses may also include one or more spacers or guides 4781 that may be within the distal end region of the elongate body and may maintain spacing between the arms, and may coordinate the movement of the arms, including insertion/withdrawal of the arms into and/or out of the distal end region of the elongate body. The guide/spacer may include a central region that is coupled to or engaged with a central electrode 4791, shown in FIGS. 47B-47C. The central electrode 4791 may be configured as a post forming an additional mapping, sensing and/or therapeutic electrode. The guide/spacer may also have one or more channels for each arm, preventing them from shifting radially within the elongate body, while still allowing longitudinal movement.

The extension region 4731, 4731', 4731" of each arm may be configured to extend beyond the treatment electrode outer radius, and may allow a larger mapping area. In general, the use of dedicated, tubular arms through which the connectors (e.g., wires) and/or additional sensors, e.g., EM sensor(s), may be positioned may be particularly beneficial and may protect the applicator, insulate the wires, and increase the overall robustness of the apparatus.

In any of these examples the apparatus may include at least one sensor (e.g., an electromagnetic sensor 4787) within the arm, including, for example, within the extension region 4731, 4731', 4731" of one or more (e.g., all) of the arms.

Figure 48:
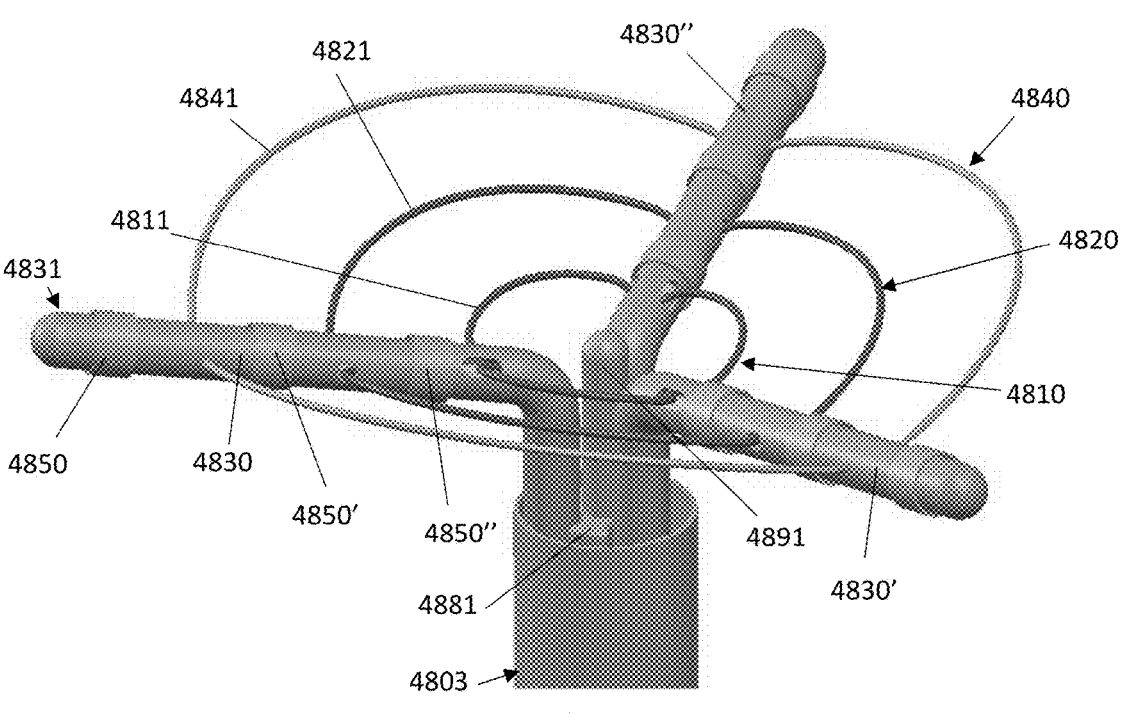
FIG. 48 is another example of an apparatus for delivering pulsed electric fields, including a plurality of mapping and/or sensing electrodes.

The applicator apparatuses described herein may also be configured to include more than two treatment electrodes, as mentioned above. For example, FIG. 48 illustrates one example of an apparatus configured as an applicator having three arms, similar to FIGS. 47A-47C, along with mapping and/or sensing electrodes coupled to each arm 4830, 4830', 4830", and three treatment electrodes 4810, 4820, 4840, forming an inner, middle and outer ring of electrodes, respectively. As described above, each treatment electrode may be formed of a plurality of electrode lengths 4811, 4821, 4841. In this configuration mapping and/or sensing electrodes 4850, 4850', 4850" are positioned radially inward on each arm between the inner 4810 and middle 4820 rings, between the middle 4820 and outer 4840 rings, and radially outward from the outer ring 4840, e.g., on the extended arm region 4831. The example shown in FIG. 48 may also include (optionally) a central electrode 4891 and/or a spacer/guide 4881.

Figure 49:
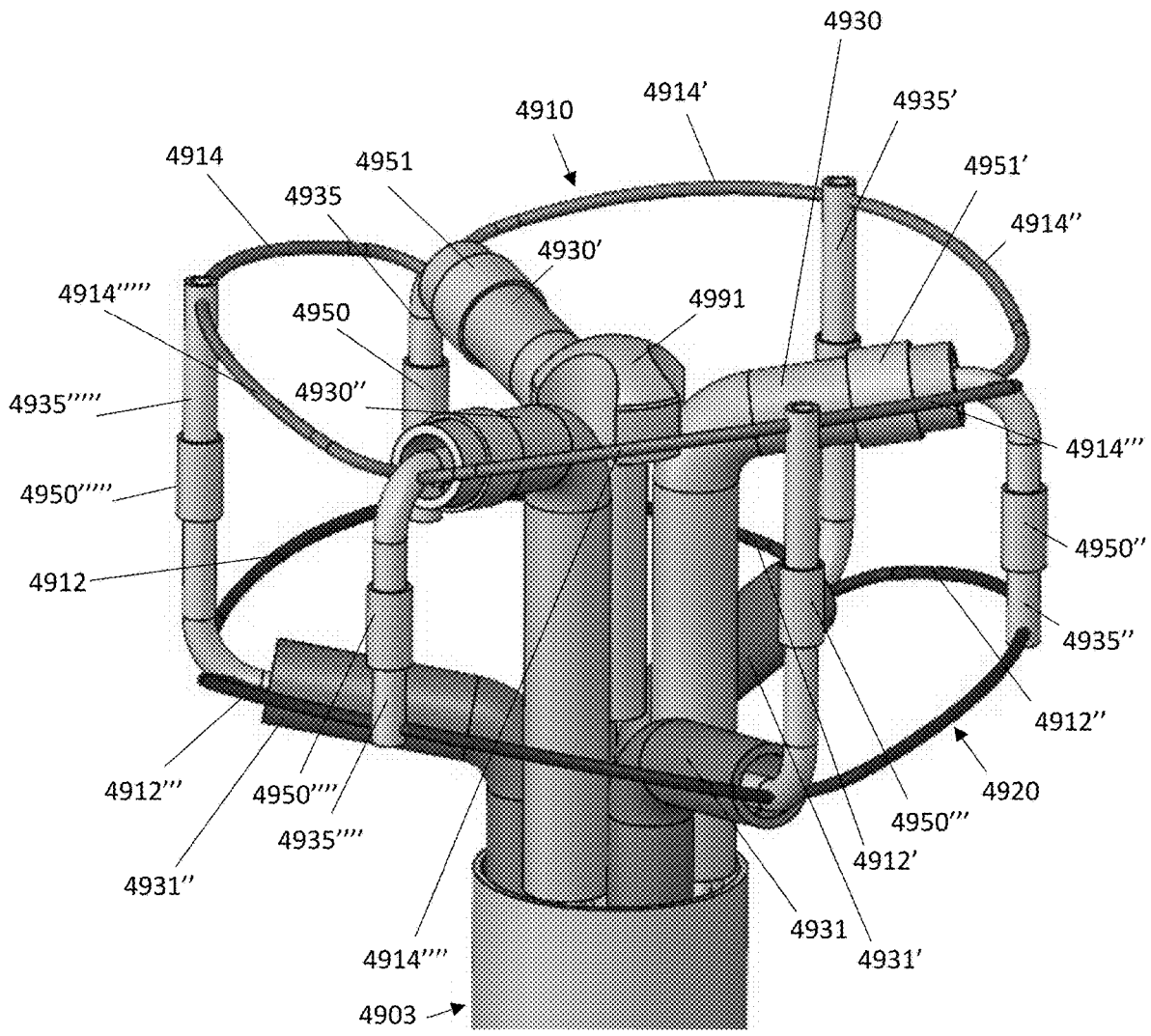
FIG. 49 is an example of an apparatus for delivering pulsed electric fields with a multi-tier configuration.

The examples shown in FIGS. 47A-47C and 48 are shown as single tier (single layer, even if funnel-shaped) ablation apparatuses including six or more mapping electrodes or sensors, for example, for detecting intracardiac electrograms (EGMs). In some examples the apparatus may instead be configured to include multiple tiers, such as a two-tier applicator as shown in FIG. 49. The two-tier structure may include multiple treatment electrodes, arranged longitudinally offset from each other, but having the same or nearly the same (e.g., not substantially different) radius as each other. A multi-tiered apparatus may include a plurality of struts (e.g., transverse struts or linking struts) that extend between the first, e.g., upper or more distal, treatment electrode and the second, lower or more proximal, treatment electrode. FIG. 49 also illustrates example locations for sets or sub-sets of sensing electrodes (e.g., mapping electrodes). The sensing electrodes may be on the various locations, including around the perimeter of the device. These apparatuses as shown in the example of FIG. 49 may enable more accurate rendering in 3D, as they include a plurality of mapping electrodes 4950, 4950', 4950", 4950''', 4950'''', 4950''''' on the lateral-facing sides of the applicator, e.g., on the struts 4935, 4935', 4935", 4935''', 4935'''', 4935''''', and may also include a plurality of sensing/mapping electrodes 4951, 4951', for example, on a first (e.g., upper) set of arms.

In some examples the struts 4935, 4935', 4935", 4935'''', 4935''''' extend from the first (e.g., upper) set of arms 4930, 4930', 4930" and/or the second (e.g., lower) set of arms 4931, 4931', 4931". The plurality of electrode lengths 4914, 4914', 4914", 4914''', 4914'''', 4914''''' forming the distal treatment electrode and the plurality of electrode lengths 4912, 4912', 4912", 4912''', 4912'''', 4912''''' forming the proximal treatment electrode may be coupled at either end of the corresponding linking struts.

For example, the apparatus for delivering pulsed electric fields shown in FIG. 49 includes an elongate body 4903 that may be the same or similar to that described above, and may be configured so that the applicator (including the electrodes) may be at least partially withdrawn into the distal end region of the elongate body for delivery or navigation to the heart or other target body region. The apparatus may also include a first plurality of arms 4930, 4930', 4930" that are configured to extend from the elongate body at an angle when deployed, and a second plurality of arms 4931, 4931', 4931" that are configured to extend from the elongate body at an angle when deployed. In some examples the upper arms may be rotationally offset from the lower arms, as shown in FIG. 49. The apparatus may also include a first plurality of electrode lengths 4914, 4914', 4914", 4914''', 4914'''', 4914''''' extending between the first plurality of arms 4930, 4930', 4930" and forming a first treatment electrode 4910, and a second plurality of electrode lengths 4912, 4912', 4912", 4912''', 4912'''', 4912''''' extending between the second plurality of arms 4931, 4931', 4931" and forming a second treatment electrode 4920 that is axially separated (e.g., axially spaced) from the first treatment electrode by the plurality of struts. The plurality of struts may extend between the first treatment electrode and the second treatment electrode, for example, parallel or substantially parallel (e.g., within +/−1°, 2°, 3°, 4°, 5°, 6°, 7°, 8°, 9°, 10°, etc.) to a distal end region of the elongate body. As mentioned, the apparatus may include a plurality of mapping and/or sensing electrodes; in some examples these mapping electrodes may be on the struts of the plurality of struts. In the example shown in FIG. 49 the apparatus also includes a central electrode 4991 that may be configured, for example, as a sensing (e.g., a mapping electrode), and a spacer (not shown) that may be integrally formed with the device and may be similar to a spacer shown in FIG. 48. Alternatively, this central electrode 4991 may be used for therapeutic or treatment applications (e.g., in combination with the first treatment electrode and the second treatment electrode).

The struts 4935 in the example of FIG. 49 may stabilize the spacing between and/or the shape of the treatment electrodes 4910, 4920.

In operation, the apparatuses described above may be used to ablate relatively large region of a tissue (e.g., heart). FIG. 50 illustrates an example of tissue ablation using an apparatus similar to those shown in the examples of FIG. 47A-47C, 48 or 49 and described above. For example, FIG. 50 shows an example of a porcine heart tissue) that has been treated by the application of energy as described herein to form ablated regions. Three exemplary ablation regions are shown 5042, 5042', 5042". The energy was applied against the surface of the tissue and was applied by bi-polar application between either a center electrode and one or more of the circumferential treatment electrodes, or between two (or more) of the circumferential treatment electrodes.

Any of these apparatuses may be configured for magnetic sensing or electrical property (e.g., impedance-based) sensing, or both. For example returning now to FIGS. 43A-43B, the apparatus shown includes both mapping electrodes 4350, 4350' and magnetic sensor(s) 4342 in addition to treatment electrodes. In some examples the applicator may couple to a third party mapping system (e.g., the Carto™ system, the Navx™ system, etc.), for example, by directly or indirectly providing input from the sensing/mapping electrodes to the mapping system. The applicators described herein may be used in conjunction with a separate mapping catheter. For example, the tissue may be mapped using a mapping catheter and system that may generate a map or model of the tissue, such as the cardiac tissue, including in particular target regions to be treated, and any of the applicators described herein may be introduced and one or more sensors, including electrodes, may be used to locate the applicator on the map or model of the tissue. The apparatus may display an image of the map or model and may concurrently show the position of the applicator on the image of the map or model to help guide the user, e.g., physician, surgeon, etc., in treating the target tissue. Alternatively, the applicators described herein may be used for both mapping and ablation. In some examples, the apparatuses described herein may include an integrated mapping system or sub-system into the apparatus.

Figure 43C:
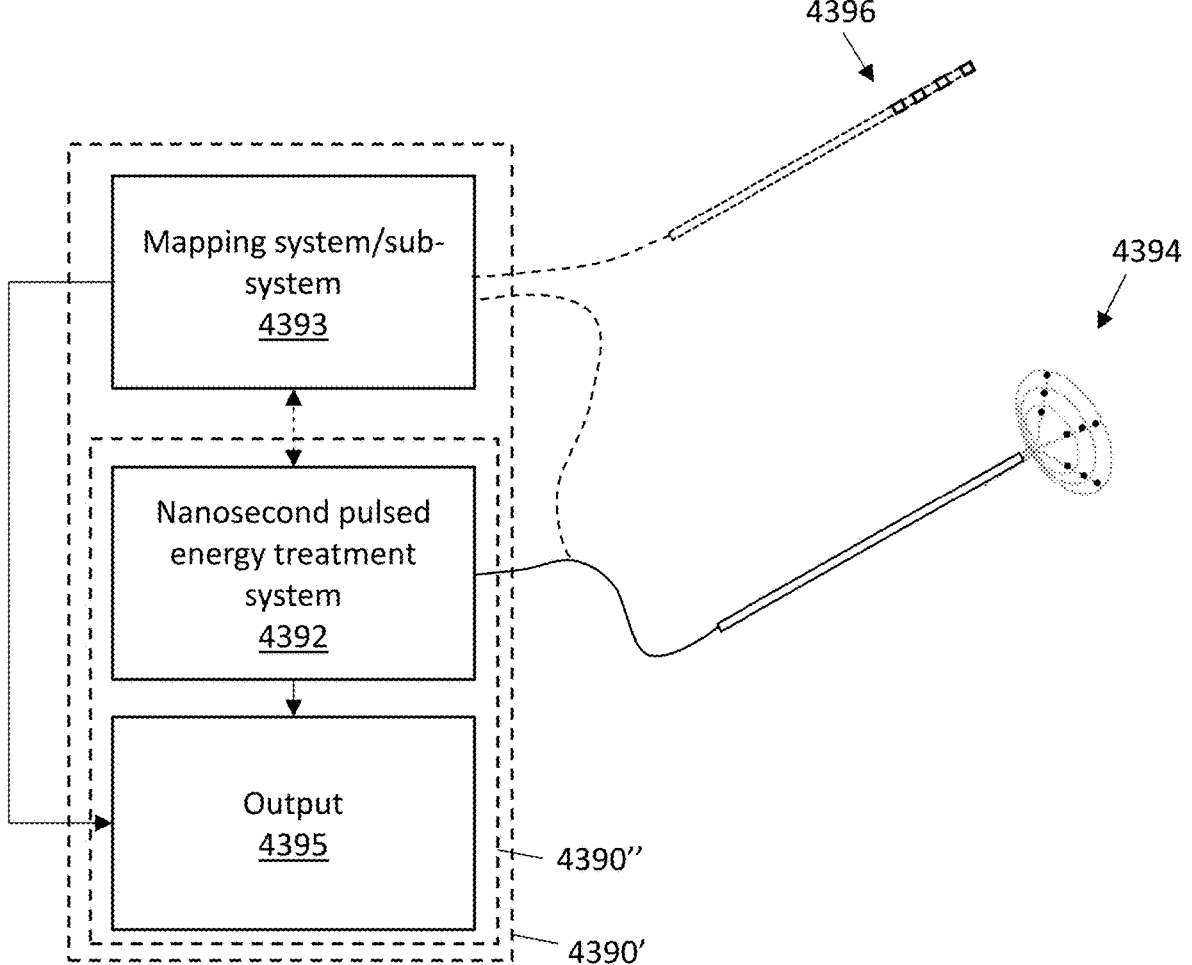
FIG. 43C schematically illustrates one example of a system including an applicator as shown in FIGS. 43A-43B.

For example, FIG. 43C schematically illustrates an example of an apparatus as described herein including both mapping and treatment. In a first embodiment of this example the apparatus includes an applicator 4394 similar to those described above, including a plurality of both treatment electrode and sensing/mapping electrodes. The applicator is coupled to a nanosecond pulsed energy treatment system 4392 which may also include a pulse generator and controller (including one or more processors) as described above (e.g., shown in FIG. 1). The system 4392 may be separate from a mapping system 4393 and/or an output 4395; the output may include one or more displays and may show the map of the tissue, including the location of the applicator based on input from the one or more sensing/mapping electrodes (or other mapping sensors) on the applicator. In some examples, as shown by the dashed lines 4390", the apparatus may include the nanosecond pulsed energy treatment system 4392 and the output 4395 and may be used in conjunction with a separate mapping system/subsystem 4393. Alternatively, in some examples the mapping system/sub-system may be included as part of the apparatus, as shown by the dashed box 4390'. In any of these apparatuses a separate mapping catheter 4396 may couple to the mapping system/subsystem 4393, as illustrated.

Wire-Based Bipolar Electrodes for Nanosecond Pulses Energy Application

Any of the methods and apparatuses described herein may be for bipolar sub-microsecond (e.g., nanosecond) pulse application using electrodes formed using thin (small profile) wires. These small-profile wires may have a maximum diameter of 0.015" (e.g., 0.38 mm) or less (e.g., 0.35 mm, 0.30 mm, 0.25 mm, 0.20 mm, 0.15 mm, 0.13 mm, 0.12 mm, 0.10 mm, etc. or less). The wires may be formed of any conductive material. The smaller profile wires are particularly appropriate for emitting the electromagnetic fields described herein. Typically such small profile wires have been avoided for use with systems that generate thermal energy, as the thinner profile wires may restrict the ablation region, and may be more prone to breakage.

For example, most energy-based therapeutic devices, such as Radio Frequency (RF) apparatuses, employ electrodes that are approximately 2-3 mm in diameter or larger. For example, RF thermal ablation relies on two types of heating: resistive and conductive. Tissue in direct contact with electrode is heated via resistive heating based on the voltage applied to the electrode and the electrode material, as well as impedance between the electrode and the tissue. Tissue that is away from the electrode may be heated as a result of the conductive heating, either directly from the electrode or by conduction of the heat from already "hot" portions of the tissue to the "colder" regions. The size of the electrode really matters in this scenario because larger electrodes cover larger area of the tissue, hence increasing the "direct" conductive heat transfer between the electrode and the tissue. In addition, if multiple electrodes are used (e.g. bipolar RF systems) the larger size of the electrodes reduces the distance between them, hence decreasing the volume of the tissue that needs to be heated by "indirect" conductive heat transfer. Even for some applications including pulsed signals (e.g., millisecond, microsecond pulsing) bulkier electrodes are believed to be advantageous because the location of the highest energy concentration is at the electrodes and the field created by the typical 2-3 kV (e.g., approximately the voltage used by most microsecond pulsed devices) is not high enough to be therapeutic. As a result, most microsecond-based apparatuses typically require the repositioning of the electrodes to create the contiguous therapeutic zone(s).

The use of such small profile wires of the present disclosure, as opposed to bulkier tubular electrodes used, e.g., with RF ablation, allows the apparatuses described herein to have a relatively smaller crossing profile. This may allow any of these apparatuses to be withdrawn into the lumens of, for example working channels of bronchoscopes/gastroscopes or delivery sheaths for cardiac applications, which may simplify and/or enable certain procedures.

The bipolar sub-microsecond (e.g., nanosecond) pulsed energy described herein may be applied at voltages that are high enough (e.g., 12-15 kV or more) to create a therapeutic field even if the electrodes are constructed from small diameter (e.g., 0.005"-0.015" or smaller) wire. Testing using such small-diameter wires have surprisingly been found to be very effective for tissue ablation and do not require repositioning to ablate tissue between them.

For example, FIGS. 44A-44D illustrate examples of different configurations of wire-based designs for apparatuses for delivering pulsed electrical energy. The small diameter of the wire electrodes of all these designs may enhance the ability of these configurations to be easily collapsible and can be compatible with the small lumens of the delivery devices. For example, such apparatuses may more easily fit within a 2.8 mm or 3.7 mm working channel of therapeutic bronchoscopes and gastroscopes, with 8.5 Fr, 9 Fr and 12 Fr inner diameters (IDs) of the cardiovascular introducer sheaths, etc. Catheters carrying such electrodes can be deflectable and/or steerable. For example FIG. 44D, described below, can be delivered through the working channel of a bronchoscope and/or gastroscope and can be brought in contact with a target tissue by deflecting the distal end of the bronchoscope or gastroscope.

The examples shown in FIGS. 44A-44D can be used as a distal part of a catheter utilized for the treatment of a tubular area of the human or animal anatomy. Such tubular areas may include, but are not limited to: esophagus, bronchi, pulmonary veins, other portions of the venous and arterial systems, etc. These apparatuses may be used to apply sub-microsecond pulsed fields in other parts of the human body. For example, these apparatuses can be a used as part of a catheter that is used during minimally invasive procedures, or a part of the device utilized during surgery.

Figure 44A:
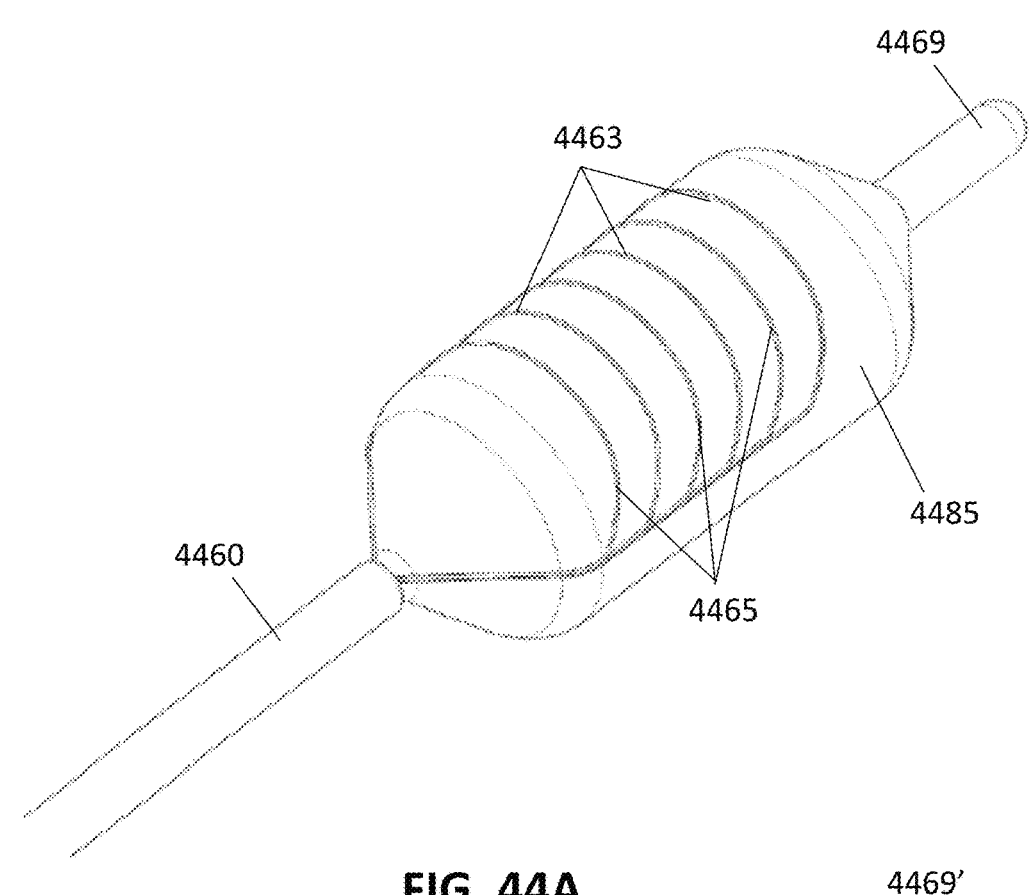
FIGS. 44A-44D show examples of apparatuses including small-diameter wire electrodes as described herein.

FIG. 44A shows a first example of an apparatus as described herein including a plurality of small-diameter wires (e.g., wires having a diameter of 0.015" or less). In FIG. 44A, the wires are arranged on an expandable member, such as a balloon 4485. Three pairs of laterally-spaced first polarity 4463 and second polarity 4465 wires are shown. The balloon is positioned on the end (e.g., end region) of an elongate body, such as a catheter elongate body 4460. The apparatus may include a distal tip region 4469 extending distally of the balloon. The balloon may be deflated to collapse the radial profile of the apparatus (not shown) and may be inflated to expand the radial profile; in FIG. 44A the apparatus is shown with the device expanded. The laterally-spaced wires (electrodes or wire electrodes) may be spaced apart, for example by between 1 mm or less (e.g., 0.5 mm, etc.) and 10 mm.

Figure 44B:
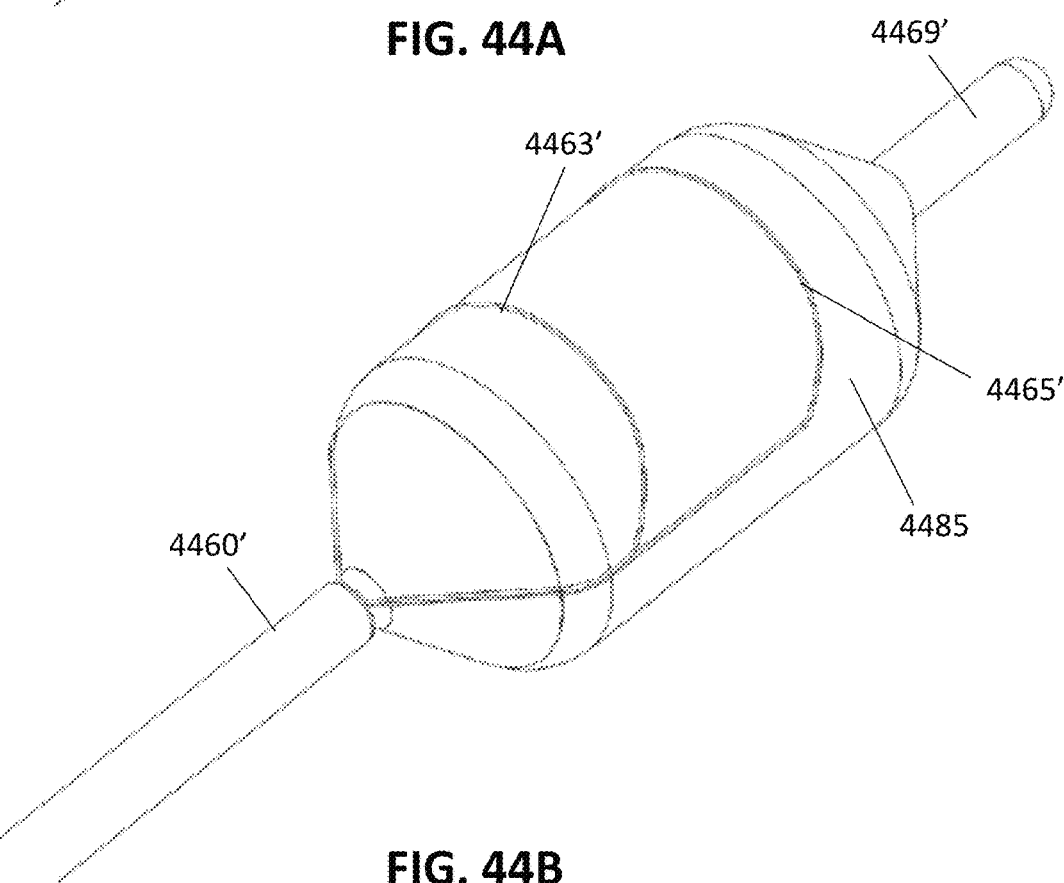

FIG. 44B shows another example of an expandable apparatus including a single pair of small-diameter wires (e.g., wires having a diameter of 0.015" or less). In this example, similar to FIG. 44A, the wire electrodes 4463', 4465' are positioned on an expandable member (e.g., balloon 4485) that is coupled, for example, to a catheter 4460', the apparatus includes a distal region 4469' extending beyond the expandable member and electrodes. In FIG. 44B the pair of wire electrode includes a first polarity wire 4463' that is laterally spaced apart from a second polarity wire 4465'. As in FIG. 44A, the electrodes extend partially (or in some examples, completely) radially around the perimeter of the expandable member, such as over between about 45 and 235 degrees (e.g., between 90 and 135 degrees, etc.) around the perimeter. Although FIGS. 44A and 44B show the wire electrodes extending transversely to the long axis of the expandable member, in some examples the electrodes may extend longitudinally along the length of the expandable member and may be located at separate radial positions, as shown in FIG. 44C.

Figure 44C:
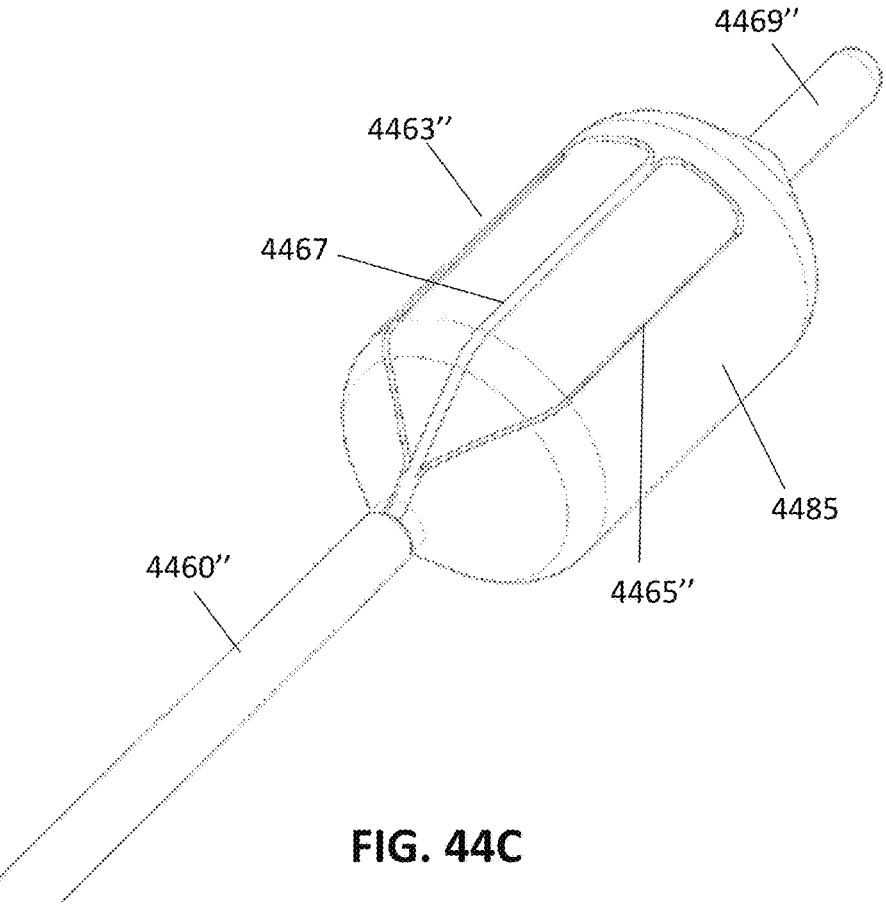

In FIG. 44C the apparatus includes an expandable member 4485 (e.g., balloon, basket, etc., shown in FIG. 44C as a balloon), onto which a plurality of wire electrodes, which may have different polarities, are arranged extending longitudinally along the length of the expandable member from different radial positions. For example, the active region of the first polarity wire electrode 4463" runs a portion or all of the length of the balloon 4485 and is radially separated from an active region of a second wire electrode 4465" by between about 40-60 degrees (in this example, between 2-5 mm). The device includes an elongate catheter body 4460" and a distal end region 4469". The active region of each electrode typically refers to the exposed region of the wire electrode; un-exposed (e.g., insulated) regions 4467 may be positioned more closely together, as shown in FIG. 44C. As in the examples shown in FIGS. 44A-44B, the expandable member of FIG. 44C may be transitioned between a collapsed configuration (no shown) and an expanded configuration (shown). The spacing between the wire electrodes may, therefore, be controlled by controlling the expansion of the expandable member.

Figure 44D:
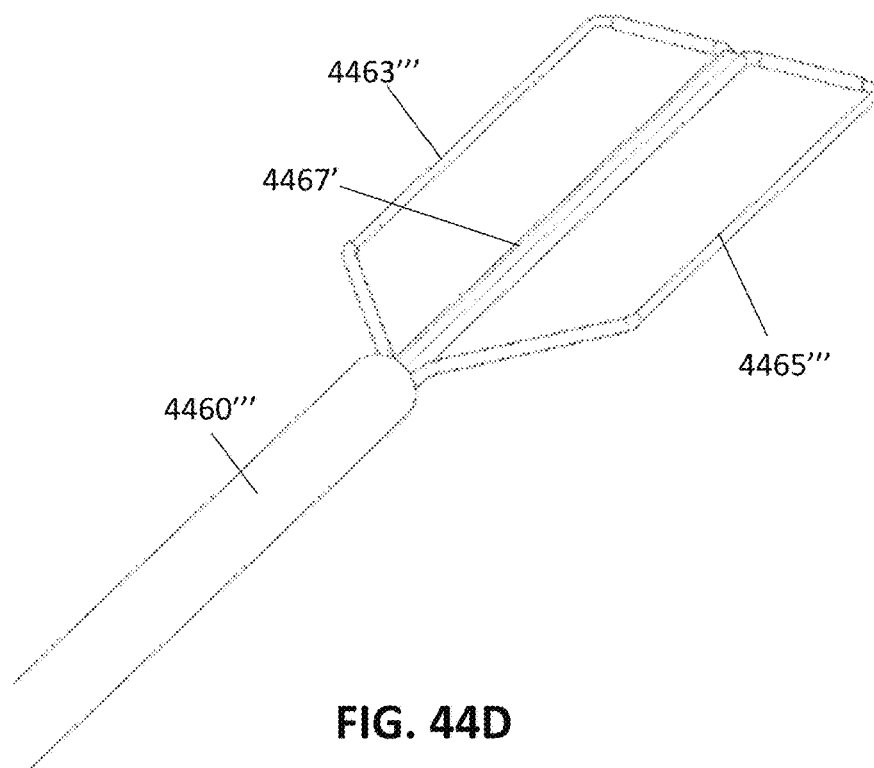

Alternatively, in some examples the apparatus may not include an expandable member, as shown in FIG. 44D. In this example the apparatus includes an elongate body 4460''' from which a pair of wire electrodes 4463—, 4465''' extend. The wire electrodes may be supported by an insulated region 4467', as shown, and may be separated from each other by a radial (and/or in some cases, longitudinal) spacing distance. The wires may be collapsed from a collapsed configuration (not shown) into an expanded configuration (shown), or vice-versa.

As described above, in any of these apparatuses the electrode assemblies may include a plurality of petals formed of loops of wire that are arranged around an expandable member, such as a balloon, expandable frame, etc. or that may themselves be expandable or part of an expandable frame. Each petal may include an active region of the electrode assembly. The wire loops forming the petals may include insulated leg regions on either side of the active region; the leg regions may extend generally longitudinally.

The legs may also be referred to herein as ribs. The active regions of each respective petal may be arranged at least partially circumferentially around the expandable member so that all of the active regions of the electrode assembly may together surround (or at least partially surround) the expandable member. Each active region may be flexible and configured to change its shape so that as the expandable member expands (and/or contracts) the active region may increase (and/or decrease) its circumferential length such that a radial circumference formed by the active regions of the electrode assembly increases and/or decreases with the expansion or contraction of the expandable member. This radial expansion may allow for treatment of a variety of differently-sized anatomical structures (e.g., lumen, walls, etc.). As mentioned, in any of these examples the active regions may each include a hinge region. In some examples the hinge region may be formed as a flexible bend (or bends) in the active region of the loops of the electrode assembly.

For example, FIGS. 45A and 45B illustrate a single loop 4500 of an electrode assembly; FIG. 45A shows the loop in an un-expanded configuration and FIG. 45B shows the same loop in an expanded configuration. In FIG. 45A the loop includes an active region 4522 that is an exposed (un-insulated) wire extending between two insulated regions 4571, 4571'. The active region 4522 is flexible, for example, it may include or is configured to provide for a flexible bend 4512, 4512'. The active region of the loop may be arranged on and/or at least partially attached to an expandable member. As the expandable member expands, the loop may transition from the narrower shape shown in FIG. 45A to the wider shape shown in FIG. 45B. The flexible bend 4512 has an initial angle (e.g., between about 90 degrees and 160 degrees) that may increase as the expandable member expands to an expanded angle that is greater than the initial angle (e.g., up to about 180 degrees). Specifically, as shown in FIGS. 45A-45B the active region changes shape to increase the effective radial circumference distance 4560, 4560' of the electrode assembly to which it forms a part.

In any of these apparatuses the electrode assemblies may include multiple petals, which may be arranged circumferentially, as shown in FIG. 45C. In addition, as described above, the electrode assemblies may be arranged adjacent to each other along the length of the expandable member. The spacing between adjacent active regions of the electrode assemblies may be approximately the same along the length of the active regions(s) in both the un-expanded and expanded configurations, e.g., as the expandable member is expanded.

In FIG. 45C, the apparatus includes four electrode assemblies 4522, 4523, 4524, 4525 formed from a plurality of small-diameter wires (e.g., wires having a diameter of 0.015" or less). In FIG. 45C, the wires are arranged on an expandable balloon 4528. Each electrode assembly forms three petals that are arranged over the balloon. In FIG. 45C, four electrode assembly, each having three active regions, corresponding to one active region per petal, are shown. The active regions of each electrode assembly include a flexible bend 4512 about midway along the active region. In this example, the electrode assemblies may be paired, so that the first 4522 and third 4524 electrode assemblies may have a first polarity and the second 4523 and fourth 4525 electrode assemblies may have a second polarity. In some examples the first and third electrode assemblies may be electrically coupled together and the second 4523 and fourth electrode assemblies 4252 may be electrically coupled together. Alternatively, the first, second, third, and fourth electrode assemblies may be separately addressable. The balloon is positioned on the end region of an elongate body (not shown in FIG. 45C), such as a catheter elongate body. The balloon may be deflated to collapse the radial profile (e.g., diameter) of the apparatus and may be inflated to expand the radial profile; in FIG. 45C the apparatus is shown with the balloon relatively collapsed. The laterally-spaced active regions of the electrode assemblies 4522, 4523, 4524, 4525 may be spaced apart, for example, by between about 1 mm or less (e.g., 0.5 mm, etc.) and 10 mm. The active regions in this example are framed on either side by insulation 4571, 4571'.

Figure 45D:
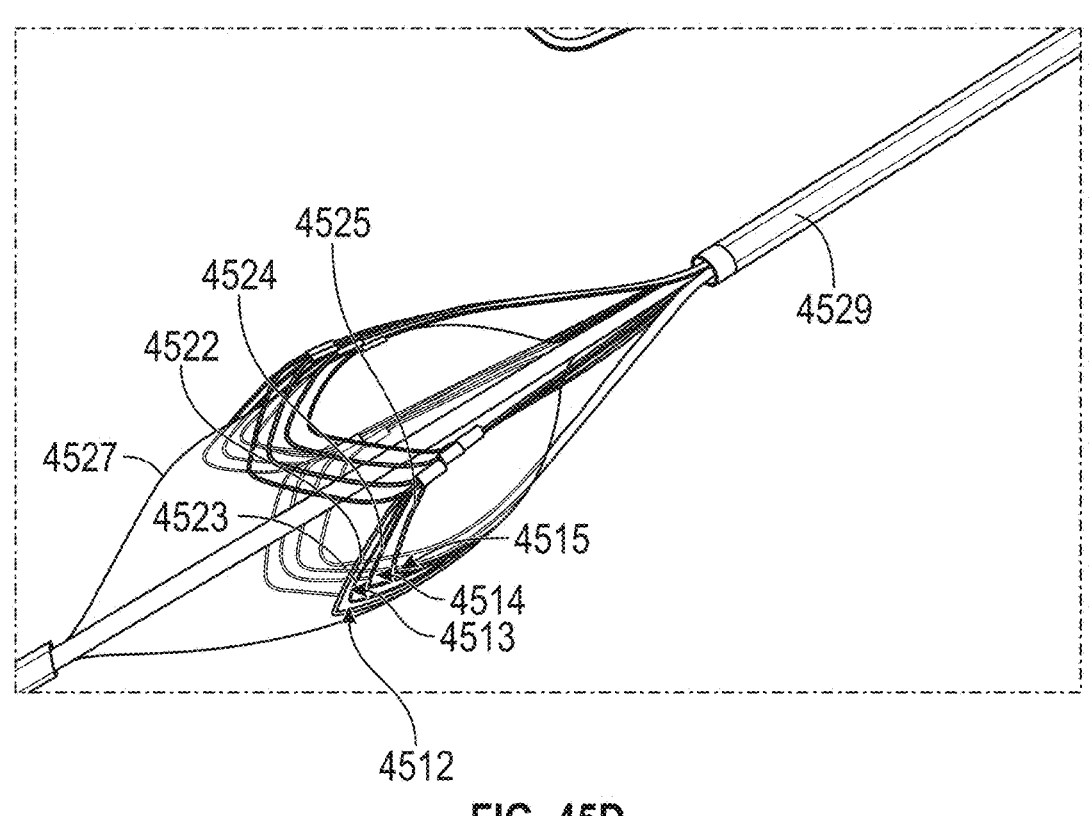
FIGS. 45D-45E illustrate the expansion of an apparatus such as that shown in FIG. 45C.
Figure 45E:
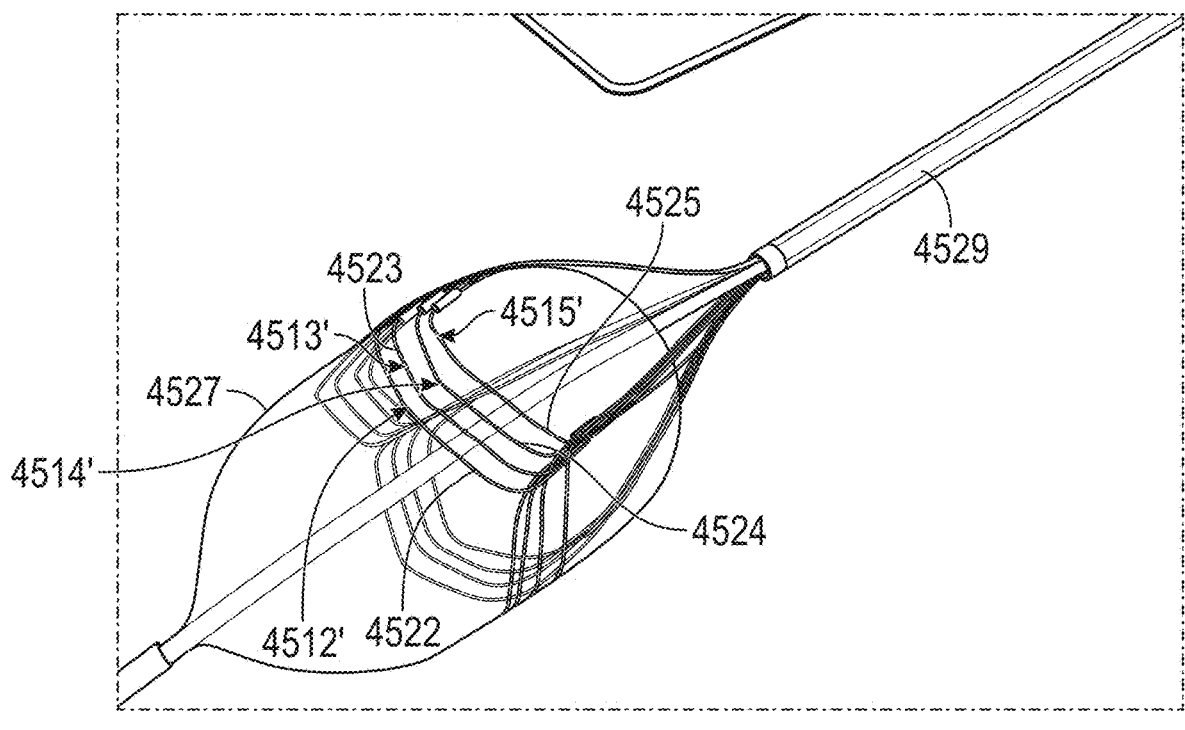

FIGS. 45D and 45C illustrate examples of an apparatus having an elongate member (e.g., shaft) 4529, four electrode assemblies 4522, 4523, 4524, 4525, each with four petals forming active regions, each active region including a flexible bend 4512, 4513, 4514, 4515 arranged over an expandable balloon 4528. The wires forming the electrode assemblies may be shape-memory alloy (e.g., Nitinol) wires, that are arranged circumferentially in loops (forming petals) around the compliant or semi-compliant balloon 4528. As shown in FIG. 45D, four identical petals are arranged around the balloon. Each loop of the Nitinol wire, in some implementations, may be shape-set so that a V-shape (flexible bend) is present as shown in FIG. 45D. The V-shaped bend has its smallest angle when wires are resting over the non-inflated or minimally inflated balloon (FIG. 45D). The angle gets larger with the inflation of the balloon, straightening the wire as shown in FIG. 45E. The V-shape allows the wire to expand as the balloon expands, and as a result, does not restrict the expansion of the balloon as may happen without the flexible bend(s) in the wire of the electrode assemblies.

FIG. 45E shows the same apparatus as FIG. 45D, with the balloon 4528 expanded. As described above, the active regions of each petal forming the electrode assemblies transition from a first bend angle 4512, 4513, 4514, 4515 shown in FIG. 45D to a more open (larger) bend angle 4512', 4513', 4514', 4515' shown in FIG. 45E.

The strength of the electric field between the active regions of the electrode assemblies (e.g., wires) can be varied by varying either the applied voltage and/or by varying the distance between wires. As shown in FIGS. 45D and 45E, in some examples the distance between the active regions is fixed and cannot be changed, i.e., is not adjustable. Further the apparatuses may be configured so that, as the shape of each active zone changes, e.g., by bending of the flexible bend during expansion/contraction of the balloon, the spacing or distance between the active regions remains constant along the lengths of the active regions.

In FIGS. 45D-45E four petals are shown. In general, any appropriate number of petals may be used. For example, to generate circumferential ablation without rotating the catheter, at least two petals may be used. In some examples, 3, 4, 5 or 6 (or more) petals may be used and may be arranged around the balloon. Although more petals may better maintain the distance between wires, more petals may also increase the crossing profile of the device, as it may require more space to fit inside the shaft 4529 of the apparatus, which may increase the minimum size of the apparatus.

Figures 46A, 46B:
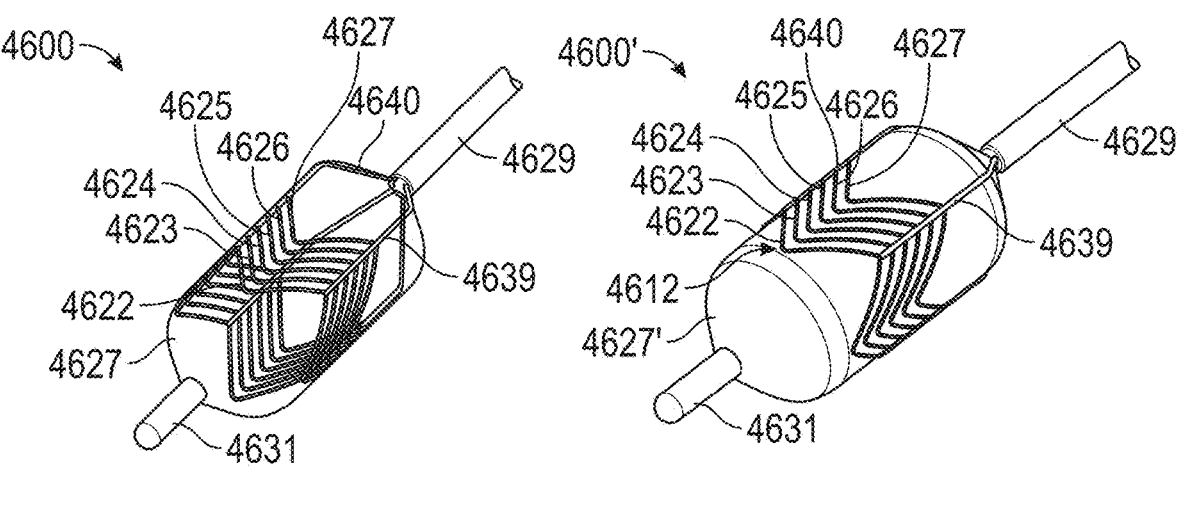
FIGS. 46A-46C show examples of apparatus similar to those shown in FIGS. 45C-45E.
Figure 46C:
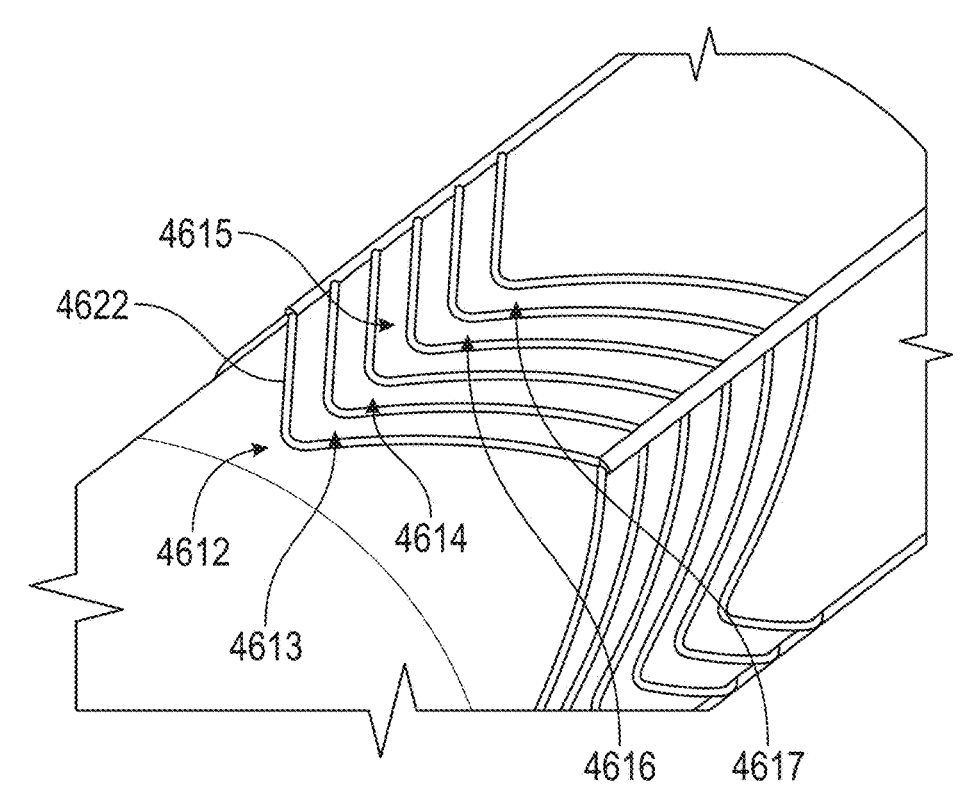

FIGS. 46A-46C illustrate other examples of apparatuses as described herein. For example, in FIG. 46A the apparatus 4600 includes an expandable balloon 4628 at the end region of an elongate member 4629. A distal tip 4631 extends distally of the balloon. In some examples, (see, e.g., FIG. 45C-45E) the elongate shaft may extend through the balloon. In this example the balloon is transparent, and six electrodes (three pairs) 4622, 4623, 4624, 4625, 4626, 4627 forming four petals are arranged on the balloon. The wires are collected into four ribs 4639, 4640. FIGS. 46B and 46C show another example of an apparatus 4600' similar to that shown in FIG. 46A, in which the balloon 4628' is opaque. In this example the six electrodes (three pairs) 4622, 4623, 4624, 4625, 4626, 4627 also form four petals that are arranged on the balloon. Each of the six active regions of each electrode assembly includes a flexible bend 4612, 4613, 4614, 4615, 4616, 4617 as described above and shown in greater detail in FIG. 46C. Any number of the electrode assemblies (e.g., wires) may be used, as appropriate. For example, if a larger area needs to be ablated, the number of electrode assemblies may be increased and/or a distance between the active regions of the electrode assemblies may be increased. For example, if a desired length of the ablation region is 10 mm and a distance between the active regions of the electrode assemblies is 1 mm, then 11 electrode assemblies (wires) may be arranged on the balloon. As it will be understood by those skilled in the art, any appropriate number of wires and distances between the wires can be implemented.

In any of these apparatuses, the electrode assemblies may be coupled to the balloon along all or a portion of the length of the electrode assembly wire(s). In some examples the wire loops of the electrode assembly/assemblie(s) are attached to the balloon at a few attachment regions, such as at the flexible bend and/or at the ribs. In some examples the wire loops are slidably attached to the balloon (e.g., via a threading attachment, etc.). In some examples discrete attachment regions couple the first, second, etc. loops and/or the ribs. In some examples the electrode assemblies are not attached to the expandable member. The electrode assemblies may be shape-set, e.g., into an expanded or unexpanded configuration.

Methods of Use of the Apparatuses of the Present Disclosure

The apparatuses described herein can include or be included as part of a catheter used during a minimally invasive procedure or a part of a device utilized during surgery. As mentioned above, the apparatuses described herein, including (but not limited) to those shown in FIGS. 22A-22C, 23A-23F, 25 and 26 may be used to treat a body lumen by applying pulsed sub-microsecond (e.g., nanosecond) energy. For example, these apparatuses may be used to treat arterial stenosis or re-stenosis. In some examples, these apparatuses may be used to treat Barret's esophagus.

In general, the methods and apparatuses described herein may be used to apply sub-sub-microsecond (e.g., nanosecond) pulsed energy. However, any of the apparatuses described herein may also be configured to apply other types of energy, e.g. RF or micro-pulsed based electrical field energy.

In some examples, the devices described herein may be inserted through, and/or used with, a catheter or other delivery device. For example, any of these apparatuses may be inserted through a working channel of an endoscope, such as a bronchoscope or gastroscope. In some examples, the apparatus may include a catheter, e.g., with an expandable active region including electrodes, that may be used with an expanding frame (e.g., struts, ribs, etc.) and/or a balloon, which may be used in bronchial system or esophagus and may be introduced through the working channel of a bronchoscope or gastroscope. The endoscope (e.g., bronchoscope or gastroscope) may be placed adjacent to treatment site, which may be visualized (imaged) via a scope or camera, such as a bronchoscopic vision (camera built in the scope). Then the apparatus may be introduced through the scope's working channel. Subsequently the apparatus (e.g., frame and/or balloon) may be expanded, so it expands and the electrodes on the surface of the frame/balloon are placed in contact with the tissue of the treatment site. Energy can then be delivered to the electrodes. The apparatus may then be collapsed (e.g., by deflating the balloon, contracting the frame, etc.) and repositioned either my moving the apparatus or the scope and the device together to the next treatment site where the active region expansion and energy application can be repeated.

For example, apparatuses of the present disclosure may be used for treating an endoluminal cancer, for example, by inserting the apparatus of the present disclosure through a body vessel (using a catheter or, where applicable, a laparoscopic device), expanding the apparatus at the treatment site (e.g., at or adjacent the cancer within the lumen) and applying energy, and in particular nanosecond pulsed electrical energy, to treat the tissue. In some examples, these apparatuses described herein may be used for treating a prostate, such as for treating prostate cancer and/or benign prostate hyperplasia. For example, describe herein are methods of treating a prostate by inserting an apparatus as described herein through a urethra (e.g., using various catheter-based designs described herein). In some examples the apparatus may be inserted trans-urethrally, while in some examples, the apparatus may be inserted percutaneously. Transurethral delivery may include insertion of the luminal catheter through the penis, through the urethra and into the prostate, where energy delivery may be applied.

Other examples of tissues that may be treated may include lungs (e.g., treating lung cancer), pancreas (e.g., pancreatic cancer), and the like. Other example tissues (body vessels) and methods of treatment are described herein.

The preceding methods and apparatuses describe for convenience of the description an example of an arterial treatment using pulsed electrical treatment. However, other treatments are contemplated.

All publications and patent applications mentioned in this specification are herein incorporated by reference in their entirety to the same extent as if each individual publication or patent application was specifically and individually indicated to be incorporated by reference. Furthermore, it should be appreciated that all combinations of the concepts discussed in the present disclosure (provided such concepts are not mutually inconsistent) are contemplated as being part of the inventive subject matter disclosed herein and may be used to achieve the benefits described herein.

As mentioned above, any of the apparatuses described herein may be implemented in robotic systems that may be used to position and/or control the electrodes during a treatment. For example, a robotic system may include a movable (robotic) arm to which elongate applicator tool is coupled. Various motors and other movement devices may be incorporated to enable fine movements of an operating tip of the elongate applicator tool in multiple directions. The robotic system and/or elongate applicator tool may further include at least one image acquisition device (and preferably two for stereo vision, or more) which may be mounted in a fixed position or coupled (directly or indirectly) to a robotic arm or other controllable motion device. In some examples, the image acquisition device(s) may be incorporated into the elongate applicator tool.

Examples of the methods of the present disclosure may be implemented using computer software, firmware, or hardware. Various programming languages and operating systems may be used to implement the present disclosure. The program that runs the method and system may include a separate program code including a set of instructions for performing a desired operation or may include a plurality of modules that perform such sub-operations of an operation or may be part of a single module of a larger program providing the operation. The modular construction facilitates adding, deleting, updating and/or amending the modules therein and/or features within the modules.

In some examples, a user may select a particular method or example of this application, and the processor will run a program or algorithm associated with the selected method. In certain examples, various types of position sensors may be used. For example, in certain examples, a non-optical encoder may be used where a voltage level or polarity may be adjusted as a function of encoder signal feedback to achieve a desired angle, speed, or force.

Certain examples may relate to a machine-readable medium (e.g., computer-readable media) or computer program products that include program instructions and/or data (including data structures) for performing various computer-implemented operations. A machine-readable medium may be used to store software and data which causes the system to perform methods of the present disclosure. The above-mentioned machine-readable medium may include any suitable medium capable of storing and transmitting information in a form accessible by processing device, for example, a computer. Some examples of the machine-readable medium include, but not limited to, magnetic disc storage such as hard disks, floppy disks, magnetic tapes. It may also include a flash memory device, optical storage, random access memory, etc. The data and program instructions may also be embodied on a carrier wave or other transport medium. Examples of program instructions include both machine code, such as produced by a compiler, and files containing higher level code that may be executed using an interpreter.

Any of the methods (including user interfaces) described herein may be implemented as software, hardware or firmware, and may be described as a non-transitory computer-readable storage medium storing a set of instructions capable of being executed by a processor (e.g., computer, tablet, smartphone, etc.), that when executed by the processor causes the processor to perform or control performing of any of the steps, including but not limited to: displaying, communicating with the user, analyzing, modifying parameters (including timing, frequency, intensity, etc.), determining, alerting, or the like. In some exemplary examples, hardware may be used in combination with software instructions to implement the present disclosure.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one example, the features and elements so described or shown can apply to other examples. It will also be appreciated by those of skill in the art that references to a structure or feature that is disposed "adjacent" another feature may have portions that overlap or underlie the adjacent feature.

Terminology used herein is for the purpose of describing particular examples only and is not intended to be limiting of the invention(s) of the present disclosure. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive if it is expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative examples are described above, any of a number of changes may be made to various examples without departing from the scope of the invention as described by the claims. For example, the order in which various described method steps are performed may often be changed in alternative examples, and in other alternative examples one or more method steps may be skipped altogether. Optional features of various device and system examples may be included in some examples and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other examples and variations may be utilized and derived there from, such that structural and logical substitutions and changes may be made without departing from the scope of this disclosure. Such examples of the inventive subject matter may be referred to herein individually or collectively by the term "invention" merely for convenience and without intending to voluntarily limit the scope of this application to any single invention or inventive concept, if more than one is, in fact, disclosed. Thus, although specific examples have been illustrated and described herein, any arrangement calculated to achieve the same purpose may be substituted for the specific examples shown. This disclosure is intended to cover any and all adaptations or variations of various examples. Combinations of the above examples or some features of the provided examples, and other examples not specifically described herein, will be apparent to those of skill in the art upon reviewing the above description.

What is claimed is:

1. An apparatus for delivering pulsed electric fields, the apparatus comprising:
   an elongate body;
   a plurality of arms configured to extend from the elongate body at an angle in a deployed state;

a first electrode extending between and connected to the plurality of arms and forming a first treatment electrode;
   a second electrode extending between and connected to the plurality of arms and forming a second treatment electrode that is radially outward of the first treatment electrode in the deployed state; and
   one or more mapping and/or sensing electrodes on the plurality of arms.

2. The apparatus of claim 1, wherein the one or more mapping and/or sensing electrodes comprises mapping and/or sensing electrodes on an extension region of each arm of the plurality of arms that is radially outward from the second treatment electrode in the deployed state.

3. The apparatus of claim 2, wherein the one or more mapping and/or sensing electrodes comprises one or more mapping and/or sensing electrodes on an intermediate region of each arm of the plurality of arms that is between the first treatment electrode and the second treatment electrode.

4. The apparatus of claim 1, wherein the arms of the plurality of arms are configured to extend from the elongate body in the deployed state at an angle of between 20 and 90 degrees relative to the elongate body.

5. The apparatus of claim 1, wherein the arms of the plurality of arms are configured to transition from a delivery state, wherein each arm of the plurality of arms at least partially within the elongate body or within a delivery sheath, into a deployed state wherein each arm of the plurality of arms extends at an angle from the elongate body.

6. The apparatus of claim 1, further comprising a spacer in a distal end region of the elongate body to maintain a spacing of each arm of the plurality of arms within the distal end region of the elongate body.

7. The apparatus of claim 1, wherein the first electrode comprises a first plurality of lengths of wire forming arcs extending between the plurality of arms; further wherein the second electrode comprises a second plurality of lengths of wire forming arcs extending between the plurality of arms.

8. The apparatus of claim 1, wherein the first electrode comprises a first loop forming the first treatment electrode and the second electrode comprises a second loop forming the second treatment electrode.

9. The apparatus of claim 1, further comprising a central electrode configured to extend distally from a distal end of the elongate body.

10. The apparatus of claim 9, wherein the central electrode comprises 1) a mapping and/or sensing electrode, and/or 2) a central treatment electrode configured to operate at a different polarity than at least one of the first or second treatment electrodes.

11. The apparatus of claim 1, further comprising an electromagnetic sensor coupled to one or more arms of the plurality of arms.

12. The apparatus of claim 1, further comprising a third electrode extending between and connected to the plurality of arms and forming a third treatment electrode that is radially outward of the first treatment electrode and the second treatment electrode in the deployed state.

13. The apparatus of claim 1, wherein the first electrode and the second electrode are each formed of a wire having a diameter of less than 0.2 mm.

14. The apparatus of claim 1, wherein the first treatment electrode comprises an anode and the second treatment electrode comprises a cathode, wherein the apparatus is configured to deliver a pulse energy between the first treatment electrode and the second treatment electrode.

15. The apparatus of claim 1, wherein the first and the second treatment electrodes are configured to deliver microsecond, nanosecond or picosecond electric pulses.

16. The apparatus of claim 1, wherein the first treatment electrode and the second treatment electrode have a different size circumference.

17. The apparatus of claim 1, wherein at least some arms of the plurality of arms comprise hollow insulated members within or through which at least a portion of the first treatment electrode or the second treatment electrode and/or electrical connectors extend.

18. The apparatus of claim 1, wherein at least one electrode is configured as both a treatment electrode and as a mapping/sensing electrode.

19. An apparatus for delivering pulsed electric fields, the apparatus comprising:

an elongate body;

a first plurality of arms configured to extend from the elongate body at an angle in a deployed state;

a second plurality of arms configured to extend from the elongate body at an angle in the deployed state;

a first electrode extending between and connected to the first plurality of arms and forming a first treatment electrode;

a second electrode extending between and connected to the second plurality of arms and forming a second treatment electrode that is separated from the first treatment electrode along a longitudinal axis of the elongate body; and one or more mapping and/or sensing electrodes.

20. The apparatus of claim 19, further comprising a plurality of struts extending between the first treatment electrode and the second treatment electrode substantially parallel to a distal end region of the elongate body, wherein the second treatment electrode is axially separated from the first treatment electrode by the plurality of struts.

21. The apparatus of claim 20, wherein at least one of the one or more mapping and/or sensing electrodes is on the struts of the plurality of struts.

22. The apparatus of claim 20, wherein the struts of the plurality of struts are coupled to at least one of the first plurality of arms and/or the second plurality of arms.

23. The apparatus of claim 20, wherein the substantially parallel to the distal end region of the elongate body comprises up to plus/minus 10 degrees from the longitudinal axis of the distal end region of the elongate body.

24. The apparatus of claim 19, wherein the one or more mapping and/or sensing electrodes comprises a plurality of mapping and/or sensing electrodes and at least some of the plurality of mapping and/or sensing electrodes are on the first plurality of arms.

25. The apparatus of claim 19, wherein the first plurality of arms is rotationally offset from the second plurality of arms.

26. The apparatus of claim 19, wherein the arms of the first plurality of arms and/or the second plurality of arms are configured to extend from the elongate body in the deployed state at an angle of between 20 and 90 degrees relative to the elongate body.

27. The apparatus of claim 19, wherein the arms of the first and second plurality of arms are configured to transition from a delivery state wherein each arm of the first and second plurality of arms at least partially within a delivery sheath or within the elongate body into a deployed state wherein each arm of the first and second plurality of arms extends at an angle from the elongate body.

28. The apparatus of claim 19, further comprising a central electrode configured to extend distally from a distal end of the elongate body, wherein the central electrode comprises a mapping and/or sensing electrode.

29. The apparatus of claim 19, further comprising a central electrode configured to extend distally from a distal end of the elongate body, wherein the central electrode comprises a treatment electrode and wherein the apparatus further configured to apply bipolar energy between either: 1) the center electrode and the first treatment electrode, 2) the center electrode and the second treatment electrode, or 3) the first treatment electrode and the second treatment electrode.

30. The apparatus of claim 19, wherein the one or more mapping and/or sensing electrodes is also configured for use as a treatment electrode.

* * * * *